(12) United States Patent
Saha

(10) Patent No.: US 8,062,886 B2
(45) Date of Patent: *Nov. 22, 2011

(54) PLASMID SYSTEM FOR MULTIGENE EXPRESSION

(75) Inventor: Deba P. Saha, Nutley, NJ (US)

(73) Assignee: Schering Corporation, Kenilworth, NJ (US)

(*) Notice: Subject to any disclaimer, the term of this patent is extended or adjusted under 35 U.S.C. 154(b) by 860 days.

This patent is subject to a terminal disclaimer.

(21) Appl. No.: 11/986,041

(22) Filed: Nov. 19, 2007

(65) Prior Publication Data

US 2008/0311623 A1    Dec. 18, 2008

Related U.S. Application Data

(63) Continuation of application No. 10/986,498, filed on Nov. 10, 2004, now Pat. No. 7,326,567.

(60) Provisional application No. 60/519,230, filed on Nov. 12, 2003.

(51) Int. Cl.
  *C12N 15/63* (2006.01)
  *C07K 16/00* (2006.01)
  *C07H 21/04* (2006.01)

(52) U.S. Cl. ............... 435/320.1; 530/387.1; 536/23.53

(58) Field of Classification Search .................. None
See application file for complete search history.

(56) References Cited

U.S. PATENT DOCUMENTS

| | | | |
|---|---|---|---|
| 4,543,439 A | 9/1985 | Frackelton, Jr. et al. | |
| 5,198,340 A | 3/1993 | Mukku | |
| 5,262,308 A | 11/1993 | Baserga | |
| 5,942,412 A | 8/1999 | Prager et al. | |
| 5,958,872 A | 9/1999 | O'Connor et al. | |
| 5,977,307 A | 11/1999 | Friden et al. | |
| 6,022,711 A | 2/2000 | Cunningham et al. | |
| 6,084,085 A | 7/2000 | Baserga et al. | |
| 6,294,330 B1 | 9/2001 | Michnick et al. | |
| 6,300,129 B1 | 10/2001 | Lonberg et al. | |
| 6,316,462 B1 | 11/2001 | Bishop et al. | |
| 6,333,031 B1 | 12/2001 | Olsson et al. | |
| 6,346,390 B1 | 2/2002 | Olsson et al. | |
| 6,372,250 B1 | 4/2002 | Pardridge | |
| 6,537,988 B2 | 3/2003 | Lee | |
| 6,645,775 B1 | 11/2003 | Clark et al. | |
| 7,217,796 B2 | 5/2007 | Wang et al. | |
| 2002/0022023 A1 | 2/2002 | Ullrich et al. | |
| 2002/0025313 A1 | 2/2002 | Micklus et al. | |
| 2002/0107187 A1 | 8/2002 | Kingston et al. | |
| 2002/0132275 A1 | 9/2002 | Fidler et al. | |
| 2002/0155095 A1 | 10/2002 | Nagabhushan et al. | |
| 2002/0164333 A1 | 11/2002 | Nemerow et al. | |
| 2002/0169116 A1 | 11/2002 | Kingston et al. | |
| 2002/0187925 A1 | 12/2002 | Kingston et al. | |
| 2002/0197262 A1 | 12/2002 | Hasan et al. | |
| 2003/0021780 A1 | 1/2003 | Smith et al. | |
| 2003/0031658 A1 | 2/2003 | Brodt et al. | |
| 2003/0045676 A1 | 3/2003 | Kingston et al. | |
| 2003/0087342 A1 | 5/2003 | Mermod et al. | |
| 2003/0088061 A1 | 5/2003 | Staunton | |
| 2003/0092631 A1 | 5/2003 | Deshayes et al. | |
| 2003/0138430 A1 | 7/2003 | Stimmel et al. | |
| 2003/0165502 A1 | 9/2003 | Fujita-Yamaguchi | |
| 2003/0195147 A1 | 10/2003 | Pillutla et al. | |
| 2003/0235582 A1 | 12/2003 | Singh et al. | |
| 2003/0236190 A1 | 12/2003 | Pillutla et al. | |
| 2004/0009154 A1 | 1/2004 | Khan et al. | |
| 2004/0009906 A1 | 1/2004 | Kakkis et al. | |
| 2004/0018191 A1 | 1/2004 | Wang et al. | |
| 2004/0023887 A1 | 2/2004 | Pillutla et al. | |
| 2004/0047835 A1 | 3/2004 | Bianco | |
| 2004/0057950 A1 | 3/2004 | Waksal et al. | |
| 2004/0086511 A1 | 5/2004 | Zack et al. | |
| 2004/0102360 A1 | 5/2004 | Barnett et al. | |
| 2004/0116330 A1 | 6/2004 | Naito et al. | |
| 2004/0142381 A1 | 7/2004 | Hubbard et al. | |
| 2004/0228859 A1 | 11/2004 | Graus et al. | |
| 2004/0265307 A1 | 12/2004 | Singh et al. | |
| 2005/0008642 A1 | 1/2005 | Graus et al. | |
| 2005/0048050 A1 | 3/2005 | Fujita-Yamaguchi | |
| 2005/0069539 A1 | 3/2005 | Cohen et al. | |
| 2005/0084906 A1 | 4/2005 | Goetsch et al. | |
| 2005/0186203 A1 | 8/2005 | Singh et al. | |
| 2005/0244408 A1 | 11/2005 | Cohen et al. | |
| 2005/0249728 A1 | 11/2005 | Singh et al. | |
| 2005/0249730 A1 | 11/2005 | Goetsch et al. | |
| 2005/0272637 A1 | 12/2005 | Clinton et al. | |
| 2005/0272755 A1 | 12/2005 | Denis et al. | |
| 2005/0281812 A1 | 12/2005 | Cohen et al. | |
| 2006/0018910 A1 | 1/2006 | Gualberto et al. | |
| 2007/0071675 A1 | 3/2007 | Wu et al. | |

FOREIGN PATENT DOCUMENTS

| | | |
|---|---|---|
| FR | 2 834 900 | 7/2003 |
| FR | 2 834 990 | 7/2003 |
| FR | 2 834 991 | 7/2003 |
| WO | WO 91/04014 | 4/1991 |
| WO | WO 91/13160 | 9/1991 |
| WO | WO 91/14438 | 10/1991 |
| WO | WO 97/44352 | 11/1997 |
| WO | WO98/17801 | 4/1998 |

(Continued)

OTHER PUBLICATIONS

Stefania Benini et al., Inhibition of Insulin-like Growth Factor I Receptor Increases the Antitumor Activity of Doxorubicin and Vincristine Against Ewing's Sarcoma Cells, Clinical Cancer Research, vol. 7, 1790-1797, Jun. 2001.

V.M. Macaulay, Insulin-like Growth Factors and Cancer, Br. J. Cancer, 65, 311-320, 1992.

Mariana Resnicoff et al., The Role of the Insulin-like Growth Factor I Receptor in Transformation and Apoptosis, Kimmel Cancer Institute, Thomas Jefferson University pp. 76-81.

(Continued)

*Primary Examiner* — Michele K Joike

(57) ABSTRACT

The present invention provides a plasmid system which facilitates the construction of a single amplifiable plasmid that, having the potential to accommodate many independent expression cassettes, has the ability to express multi-subunit complex proteins such as antibodies and receptors.

10 Claims, 16 Drawing Sheets

FOREIGN PATENT DOCUMENTS

| | | |
|---|---|---|
| WO | WO 98/22092 | 5/1998 |
| WO | WO 98/45427 | 10/1998 |
| WO | WO 99/25378 | 5/1999 |
| WO | WO 99/28347 | 6/1999 |
| WO | WO 99/42127 | 8/1999 |
| WO | WO 99/60023 | 11/1999 |
| WO | WO 00/22130 | 4/2000 |
| WO | WO 00/50067 | 8/2000 |
| WO | WO 00/69454 | 11/2000 |
| WO | WO 01/07084 A1 | 2/2001 |
| WO | WO 01/30964 A2 | 5/2001 |
| WO | WO 01/36632 A2 | 5/2001 |
| WO | WO 01/70268 A1 | 9/2001 |
| WO | WO 01/70930 A2 | 9/2001 |
| WO | WO 01/72771 A2 | 10/2001 |
| WO | WO 01/75064 A2 | 10/2001 |
| WO | WO 01/88121 | 11/2001 |
| WO | WO 02/04522 A2 | 1/2002 |
| WO | WO 02/07783 A2 | 1/2002 |
| WO | WO 02/14525 | 2/2002 |
| WO | WO 02/27017 A2 | 4/2002 |
| WO | WO 02/31500 A2 | 4/2002 |
| WO | WO 02/43758 A2 | 6/2002 |
| WO | WO 02/053596 A2 | 7/2002 |
| WO | WO 02/054066 A2 | 7/2002 |
| WO | WO 02/072780 A2 | 9/2002 |
| WO | WO 2004/087756 A2 | 10/2002 |
| WO | WO 02/088752 A2 | 11/2002 |
| WO | WO 02/092599 A1 | 11/2002 |
| WO | WO 02/102854 A2 | 12/2002 |
| WO | WO 02/102972 A2 | 12/2002 |
| WO | WO 02/102973 A2 | 12/2002 |
| WO | WO 03/000928 A2 | 1/2003 |
| WO | WO 03/014696 A2 | 2/2003 |
| WO | WO 03/027246 A2 | 4/2003 |
| WO | WO 03/039538 A1 | 5/2003 |
| WO | WO 03/059951 A2 | 7/2003 |
| WO | WO 03/088910 A2 | 10/2003 |
| WO | WO 03/100008 A2 | 12/2003 |
| WO | WO 03/100059 A2 | 12/2003 |
| WO | WO 03/106621 A2 | 12/2003 |
| WO | WO 2004/030625 A2 | 4/2004 |
| WO | WO 2004/030627 A2 | 4/2004 |
| WO | WO 2004/056865 A2 | 7/2004 |
| WO | WO 2004/071529 A2 | 8/2004 |
| WO | WO 2004/083248 A1 | 9/2004 |
| WO | WO 2004/096224 A2 | 11/2004 |
| WO | WO 2004/096224 A3 | 11/2004 |
| WO | WO 2005/005635 A2 | 1/2005 |
| WO | WO 2005/016967 A2 | 2/2005 |
| WO | WO 2005/016970 A2 | 2/2005 |
| WO | WO2005/052005 | 6/2005 |
| WO | WO 2005/061541 A1 | 7/2005 |
| WO | WO 2005/117980 A1 | 12/2005 |
| WO | WO 2006/013472 A2 | 2/2006 |
| WO | WO 2006/020258 A2 | 2/2006 |
| WO | WO2007/093008 | 8/2007 |

OTHER PUBLICATIONS

Xiangdang Liu et al., Inhibition of Insulin-like Growth Factor I Receptor Expression in Neuroblastoma Cells Induces the Regression of Established Tumors in Mice, Cancer Research 58, 5432-5438, Dec. 1, 1998.
Jamie L. Resnik et al., Elevated Insulin-like Growth Factor I Receptor Autophosphorylation and Kinase Activity in Human Breast Cancer, Cancer Research 58, 1159-1164, Mar. 15, 1998.
Fredrika Pekonen et al., Receptors for Epidermal Growth Factor and Insulin-like Growth Factor I and Their Relation to Steroid Receptors in Human Breast Cancer, Cancer Research 48, 1343-1347, Mar. 1, 1988.
Quynh T. Rohlik et al., An Antibody to the Receptor for Insulin-like Growth Factor I Inhibits the Growth of MCF-7 Cells in Tissue Culture, Biochemical and Biophysical Research Communications, vol. 149, No. 1, 276-281, 1987.
Carlos L. Arteaga et al., Blockade of the Type I Somatomedin Receptor Inhibits Growth of Human Breast Cancer Cells in Athymic Mice, J. Clin. Invest., vol. 84, 1418-1423, Nov. 1989.
Ted Gansler et al., Rapid Communication Antibody to Type I Insulin-like Growth Factor Receptor Inhibits Growth of Wilms' Tumor in Culture and in Athymic Mice, American Journal of Pathology, vol. 135, No. 6, 961-966, Dec. 1989.
Krzysztof Reiss et al., Inhibition of Tumor Growth by a Dominant Negative Mutant of the Insulin-like Growth Factor I Receptor with a Bystander Effect, Clinical Cancer Research, vol. 4, 2647-2655, Nov. 1998.
Carlos L. Arteaga et al., Growth Inhibition of Human Breast Cancer Cells in Vitro with an Antibody Against the Type I Somatomedin Receptor, Cancer Research, 49, 6237-6241, Nov. 15, 1989.
Sandra E. Dunn et al., A Dominant Negative Mutant of the Insulin-like Growth Factor-I Receptor Inhibits the Adhesion, Invasion, and Metastasis of Breast Cancer, Cancer Research, 58, 3353-3361, Aug. 1, 1998.
Peter Burfeind, Antisense RNA to the Type I Insulin-like Growth Factor Receptor Suppresses Tumor Growth and Prevents Invasion by Rate Prostate Cancer Cells in Vivo, Proc. Natl. Acad. Sci. USA, vol. 93 7263-7268, Jul. 1996.
Diane Prager et al., Dominant Negative Inhibition of Tumorigenesis in Vivo by Human Insulin-like Growth Factor I Receptor Mutant, Proc. Natl. Acad. Sci. USA, vol. 91, 2181-2185, Mar. 1994.
Deepali Sachdev, A Chimeric Humanized Single-Chain Antibody Against the Type I Insulin-like Growth Factor (IGF) Receptor Renders Breast Cancer Cells Refractory to the Mitogenic Effects of IGF-1, Cancer Research 63, 627-635, 2003.
Hakam et al., "Expression of insulin-like growth factor-1 receptor in human colorectal cancer", Human Pathology (1999) 30(10): 1128-1133.
Sepp-Lorenzino,"Structure and function of the insulin-like growth factor I receptor", Breast Cancer Research and Treatment (1998) 47: 235-253.
R&D Systems catalogue pages-monoclonal Anti-human IGF-IR Antibody MAB391.
Xiong et al., "Growth-stimulatory monoclonal antibodies against human insulin-like growth factor I receptor" Proc. Nat. Acad. Sci. 89: 5356-5360 (1992).
Li et al., "Two new monoclonal antibodies against the α subunit of the human insulin-like growth factor-I receptor" Biochem. Biophys. Res. Comm. 196(1):92-98 (1993).
Kull et al., "Monoclonal antibodies to receptors for insulin and somatomedin-C" J. Biol. Chem. 258(10):6561-6566 (1983).
Butler et al., "Insulin-like growth factor-I receptor signal transduction: at the interface between physiology and cell biology" Comp. Biochem. Physiol. Part (B) 121(1):19-26 (1998).
Chan et al., "Plasma insulin-like growth factor-I and prostate cancer risk: a prospective study" Science. 279(5350):563-566 (1998).
Xie et al., "Expression of insulin-like growth factor-1 receptor in synovial sarcoma: association with an aggressive phenotype" Cancer Res. 59(15):3588-3591 (1999).
Steller et al., "Overexpression of the insulin-like growth factor-1 receptor and autocrine stimulation in human cervical cancer cells" Cancer Res. 56(8):1761-1765 (1996).
Pandini et al., "Insulin and insulin-like growth factor-I (IGF-I) receptor overexpression in breast cancers leads to insulin/IGF-I hybrid receptor overexpression: evidence for a second mechanism of IGF-I signaling" Clin. Cancer Res. 5(7):1935-1944 (1999).
Webster et al., "Repression of the insulin receptor promoter by the tumor suppressor gene product p53: a possible mechanism for receptor overexpression in breast cancer" Cancer Res. 56(12):2781-2788 (1996).
Ben-Schlomo et al., "Acromegaly" Endocrin. Metab. Clin. N. America 30(3):565-583 (2001).
Li et al., "Single-chain antibodies against human insulin-like growth factor I receptor: expression, purification, and effect on tumor growth", Cancer Immunol. Immunother. 49: 243-252 (2000).
Burtrum et al., "A fully human monoclonal antibody to the insulin-like growth factor I receptor blocks ligand-dependent signaling and inhibits human tumor growth in vivo." Cancer Res. Dec. 15, 2003;63(24):8912-21.

Business Wire, "Imclone systems incorporated reports advancements in several pipeline programs" (Jul. 14, 2003).
Zhu, "Monoclonal Antibodies in Cancer-Fourth International Congress (Part II), Colorado Springs, CO, USA" Investigational Drug Database Meeting Report (Sep. 3-6, 2004).
Williams, "American Association for Cancer Research-94th Annual Meeting (Part III)-Overnight Report, Washington, D.C., USA" Investigational Drug Database Meeting Report (Jul. 11-14, 2003).
Imclone Systems, Inc. Form 10-K (filed Mar. 15, 2004).
Holt et al., Domain antibodies: proteins for therapy, Trends in Biotechnology 21(11): 484-490 (2003).
Maloney et al., An Anti-Insulin-like Growth Factor I Receptor Antibody That Is a Potent Inhibitor of Cancer Cell Proliferation, Cancer Research 63, 5073-5083 (2003).
Lu et al., Simultaneous Blockade of Both the Epidermal Growth Factor Receptor and the Insulin-like Growth factor receptor signaling pathways in cancer cells with a XXX human recombinant XXX antibody, J. Bio. Chem.279(4): 2856-65 (2004).
Tang et al., Use of a peptide mimotope to guide the humanization of MRK-16, an anti-P-glycoprotein monoclonal antibody. J Biol Chem. Sep. 24, 1999;274(39):27371-8.
Boylan et al., The anti-proliferative effect of suramin towards tamoxifen-sensitive and resistant human breast cancer cell lines in relation to expression of receptors for epidermal growth factor and insulin-like growth factor-I: growth stimulation in the presence of tamoxifen. Ann Oncol. Feb. 1998;9(2):205-11.
Happerfield et al., The localization of the insulin-like growth factor receptor 1 (IGFR-1) in benign and malignant breast tissue. J Pathol. Dec. 1997;183(4):412-7.
Clarke et al., Type I insulin-like growth factor receptor gene expression in normal human breast tissue treated with oestrogen and progesterone. Br J Cancer. 1997;75(2):251-7.
Van Den Berg et al., Expression of receptors for epidermal growth factor and insulin-like growth factor I by ZR-75-1 human breast cancer cell variants is inversely related: the effect of steroid hormones on insulin-like growth factor I receptor expression. Br J Cancer. Feb. 1996;73(4):477-81.
Lebon et al., Purification of insulin-like growth factor I receptor from human placental membranes. J Biol Chem. Jun. 15, 1986;261(17):7685-9.
Warren et al., Induction of vascular endothelial growth factor by insulin-like growth factor 1 in colorectal carcinoma. J Biol Chem. Nov. 15, 1996;271(46):29483-8.
Auclair et al., Antiinsulin receptor autoantibodies induce insulin receptors to constitutively associate with insulin receptor substrate-1 and -2 and cause severe cell resistance to both insulin and insulin-like growth factor I. J Clin Endocrinol Metab. Sep. 1999;84(9):3197-3206.
Gori et al., Effects of androgens on the insulin-like growth factor system in an androgen-responsive human osteoblastic cell line. Endocrinology. Dec. 1999;140(12):5579-86.
Kasprzyk et al., Therapy of an animal model of human gastric cancer using a combination of anti-erbB-2 monoclonal antibodies. Cancer Res. May 15, 1992;52(10):2771-6.
Drebin et al., Monoclonal antibodies reactive with distinct domains of the neu oncogene-encoded p185 molecule exert synergistic antitumor effects in vivo. Oncogene. Mar. 1988;2(3):273-7.
Shin et al., Proapoptotic activity of cell-permeable anti-Akt single-chain antibodies. Cancer Res. Apr. 1, 2005;65(7):2815-24.
Lu et al., A fully human recombinant IgG-like bispecific antibody to both the epidermal growth factor receptor and the insulin-like growth factor receptor for enhanced antitumor activity. J Biol Chem. May 20, 2005;280(20):19665-72.
Cohen et al., Combination therapy enhances the inhibition of tumor growth with the fully human anti-type 1 insulin-like growth factor receptor monoclonal antibody CP-751,871. Clin Cancer Res. Mar. 1, 2005;11(5):2063-73.
Wu et al., In vivo effects of the human type I insulin-like growth factor receptor antibody A12 on androgen-dependent and androgen-independent xenograft human prostate tumors. Clin Cancer Res. Apr. 15, 2005;11(8):3065-74.
Goetsch et al., A recombinant humanized anti-insulin-like growth factor receptor type I antibody (h7C10) enhances the antitumor activity of vinorelbine and anti-epidermal growth factor receptor therapy against human cancer xenografts. Int J Cancer. Jan. 10, 2005;113(2):316-28.
Granerus et al., Effects of insulin-like growth factor-binding protein 2 and an IGF-type I receptor-blocking antibody on apoptosis in human teratocarcinoma cells in vitro. Cell Biol Int. 2001;25(8):825-8.
Kaliman et al., Antipeptide antibody to the insulin-like growth factor-I receptor sequence 1232-1246 inhibits the receptor kinase activity. J Biol Chem. May 25, 1992;267(15):10645-51.
Rodeck et al., Interactions between growth factor receptors and corresponding monoclonal antibodies in human tumors. J Cell Biochem. Dec. 1987;35(4):315-20.
Iwakiri et al., Autocrine growth of Epstein-Barr virus-positive gastric carcinoma cells mediated by an Epstein-Barr virus-encoded small RNA. Cancer Res. Nov. 1, 2003;63(21):7062-7.
Kiess et al., Human neuroblastoma cells use either insulin-like growth factor-I or insulin-like growth factor-II in an autocrine pathway via the IGF-I receptor: variability of IGF, IGF binding protein (IGFBP) and IGF receptor gene expression and IGF and IGFBP secretion in human neuroblastoma cells in relation to cellular proliferation. Regul Pept. Sep. 26, 1997;72(1):19-29.
Pritchard et al., Synovial fibroblasts from patients with rheumatoid arthritis, like fibroblasts from Graves' disease, express high levels of IL-16 when treated with Igs against insulin-like growth factor-1 receptor. J Immunol. Sep. 1, 2004;173(5):3564-9.
Jackson-Booth et al., Inhibition of the biologic response to insulin-like growth factor I in MCF-7 breast cancer cells by a new monoclonal antibody to the insulin-like growth factor-I receptor. The importance of receptor down-regulation. Horm Metab Res. Nov.-Dec. 2003;35(11-12):850-6.
Carboni et al., Tumor development by transgenic expression of a constitutively active insulin-like growth factor I receptor. Cancer Res. May 1, 2005;65(9):3781-7.
Remacle-Bonnet et al., Insulin-like growth factor-I protects colon cancer cells from death factor-induced apoptosis by potentiating tumor necrosis factor alpha-induced mitogen-activated protein kinase and nuclear factor kappaB signaling pathways. Cancer Res. Apr. 1, 2000;60(7):2007-17.
Lahm et al., Blockade of the insulin-like growth-factor-I receptor inhibits growth of human colorectal cancer cells: evidence of a functional IGF-II-mediated autocrine loop. Int J Cancer. Aug. 1, 1994;58(3):452-9.
Steele-Perkins et al., Monoclonal antibody alpha IR-3 inhibits the ability of insulin-like growth factor II to stimulate a signal from the type I receptor without inhibiting its binding. Biochem Biophys Res Commun. Sep. 28, 1990;171(3):1244-51.
Scotlandi et al., Prognostic and therapeutic relevance of HER2 expression in osteosarcoma and Ewing's sarcoma. Eur J Cancer. Jun. 2005;41(9):1349-61.
Agus et al., Response of prostate cancer to anti-Her-2/neu antibody in androgen-dependent and -independent human xenograft models. Cancer Res. Oct. 1, 1999;59(19):4761-4.
Pietras et al., Monoclonal antibody to HER-2/neureceptor modulates repair of radiation-induced DNA damage and enhances radiosensitivity of human breast cancer cells overexpressing this oncogene. Cancer Res. Mar. 15, 1999;59(6):1347-55.
Goldenberg, Trastuzumab, a recombinant DNA-derived humanized monoclonal antibody, a novel agent for the treatment of metastatic breast cancer. Clin Ther. Feb. 1999;21(2):309-18. Review.
Seely et al., Retroviral expression of a kinase-defective IGF-I receptor suppresses growth and causes apoptosis of CHO and U87 cells in-vivo. BMC Cancer. May 31, 2002;2:15.
Soos et al., A panel of monoclonal antibodies for the type I insulin-like growth factor receptor. Epitope mapping, effects on ligand binding, and biological activity. J Biol Chem. Jun. 25, 1992;267(18):12955-63.
Kalebic et al., In vivo treatment with antibody against IGF-1 receptor suppresses growth of human rhabdomyosarcoma and down-regulates p34cdc2. Cancer Res. Nov. 1, 1994;54(21):5531-4.
Baserga, The insulin-like growth factor I receptor: a key to tumor growth? Cancer Res. Jan. 15, 1995;55(2):249-52.

Rubini et al., Characterization of an antibody that can detect an activated IGF-I receptor in human cancers. Exp Cell Res. Aug. 25, 1999;251(1):22-32.

Lin et al., Structure-function relationships in glucagon: properties of highly purified des-His-1-, monoiodo-, and (des-Asn- 28, Thr -29)(homoserine lactone -27)-glucagon, Biochemistry. Apr. 22, 1975;14(8):1559-63.

Acland et al., Subcellular fate of the int-2 oncoprotein is determined by choice of initiation codon, Nature. Feb. 15, 1990;343(6259):662-5.

Cordera et al., Inhibition of insulin and epidermal growth factor (EGF) receptor autophosphorylation by a human polyclonal IgG, Biochem Biophys Res Commun. Nov. 15, 1985;132(3):991-1000.

Freund et al., Functional insulin and insulin-like growth factor-1 receptors are preferentially expressed in multiple myeloma cell lines as compared to B-lymphoblastoid cell lines, Cancer Res. Jun. 15, 1994;54(12):3179-85.

Rudikoff et al., Single amino acid substitution altering antigen-binding specificity, Proc Natl Acad Sci U S A. Mar. 1982;79(6):1979-83.

Burgess et al., Possible dissociation of the heparin-binding and mitogenic activities of heparin-binding (acidic fibroblast) growth factor-1 from its receptor-binding activities by site-directed mutagenesis of a single lysine residue, J Cell Biol. Nov. 1990;111:2129-38.

Lazar et al., Transforming growth factor alpha: mutation of aspartic acid 47 and leucine 48 results in different biological activities, Mol Cell Biol. Mar. 1988;8(3):1247-52.

Schwartz et al., A superactive insulin: [B10-aspartic acid]insulin(human), Proc Natl Acad Sci U S A. Sep. 1987;84(18):6408-11.

Jackson et al., Insulin receptor substrate-1 is the predominant signaling molecule activated by insulin-like growth factor-I, insulin, and interleukin-4 in estrogen receptor-positive human breast cancer cells. J Biol Chem. Apr. 17, 1998;273(16):9994-10003.

Desnoyers et al., Novel non-isotopic method for the localization of receptors in tissue sections. J Histochem Cytochem. Dec. 2001;49(12):1509-18.

Ricort et al. Insulin-like growth factor (IGF) binding protein-3 inhibits type 1 IGF receptor activation independently of its IGF binding affinity, Endocrinology. Jan. 2001;142(1):108-13.

Oberholzer et al., Increased survival in sepsis by in vivo adenovirus-induced expression of IL-10 in dendritic cells. J Immunol. Apr. 1, 2002;168(7):3412-8.

Wahle, The end of the message: 3'-end processing leading to polyadenylated messenger RNA. Bioessays. Feb. 1992;14(2):113-8.

Ju et al., Nucleotide sequence analysis of the long terminal repeat (LTR) of avian retroviruses: structural similarities with transposable elements. Cell. Nov. 1980;22(Pt 2):379-86.

Kaufman, Selection and coamplification of heterologous genes in mammalian cells. Methods Enzymol. 1990;185:537-66.

Takebe et al., SR alpha promoter: an efficient and versatile mammalian cDNA expression system composed of the simian virus 40 early promoter and the R-U5 segment of human T-cell leukemia virus type 1 long terminal repeat. Mol Cell Biol. Jan. 1988;8(1):466-72.

Nordenhaug et al., Versatile vectors for transient and stable expression of recombinant antibody molecules in mammalian cells, J. Immunol. Methods. May 12, 1997;204(1):77-87.

Zhang et al., An adenoviral vector expressing functional heterogeneous proteins herpes simplex viral thymidine kinase and human interleukin-2 has enhanced in vivo antitumor activity against medullary thyroid carcinoma, Endocr. Relat. Cancer Dec. 2001;8(4):315-25.

Flamez et al., Production in *Escherichia coli* of a functional murine and murine::human chimeric F(ab')2 fragment and mature antibody directed against human placental alkaline phosphatase, J. Biotechnol. Sep. 29, 1995;42(2):133-43.

Bebbington CR: "Expression of antibody genes in nonlymphoid mammalian cells" Methods: A companion to methods in Enzymology, Academic Press Inc., New York, NY, US, vol. 2, No. 2, Apr. 1991, pp. 136-145.

Page MJ et al.: "High level expression of the humanized monoclonal antibody campath-1h in Chinese hamster ovary cells" Bio/technology, Nature publishing Co., New York, NY, US, vol. 9, No. 1, Jan. 1991, pp. 64-68.

International search report for international application No. PCT/US2004/37721.

Hailey et al., Neutralizing anti-insulin-like growth factor receptor 1 antibodies inhibit receptor function and induce receptor degradation in tumor cells. Mol. Cancer Therap. 1:1349-1353 (2002).

Bagatell et al., Hsp90 inhibitors deplete key anti-apoptotic proteins in pediatric solid tumor cells and demonstrate synergistic anticancer activity with cisplatin. Int J Cancer. Jan. 10, 2005;113(2):179-88.

Baserga, Targeting the IGF-1 receptor: from rags to riches. Eur. J. Cancer. Sep. 2004;40(14):2013-5.

García-Echeverría et al., In vivo antitumor activity of NVP-AEW541-A novel, potent, and selective inhibitor of the IGF-IR kinase. Cancer Cell. Mar. 2004;5(3):231-9.

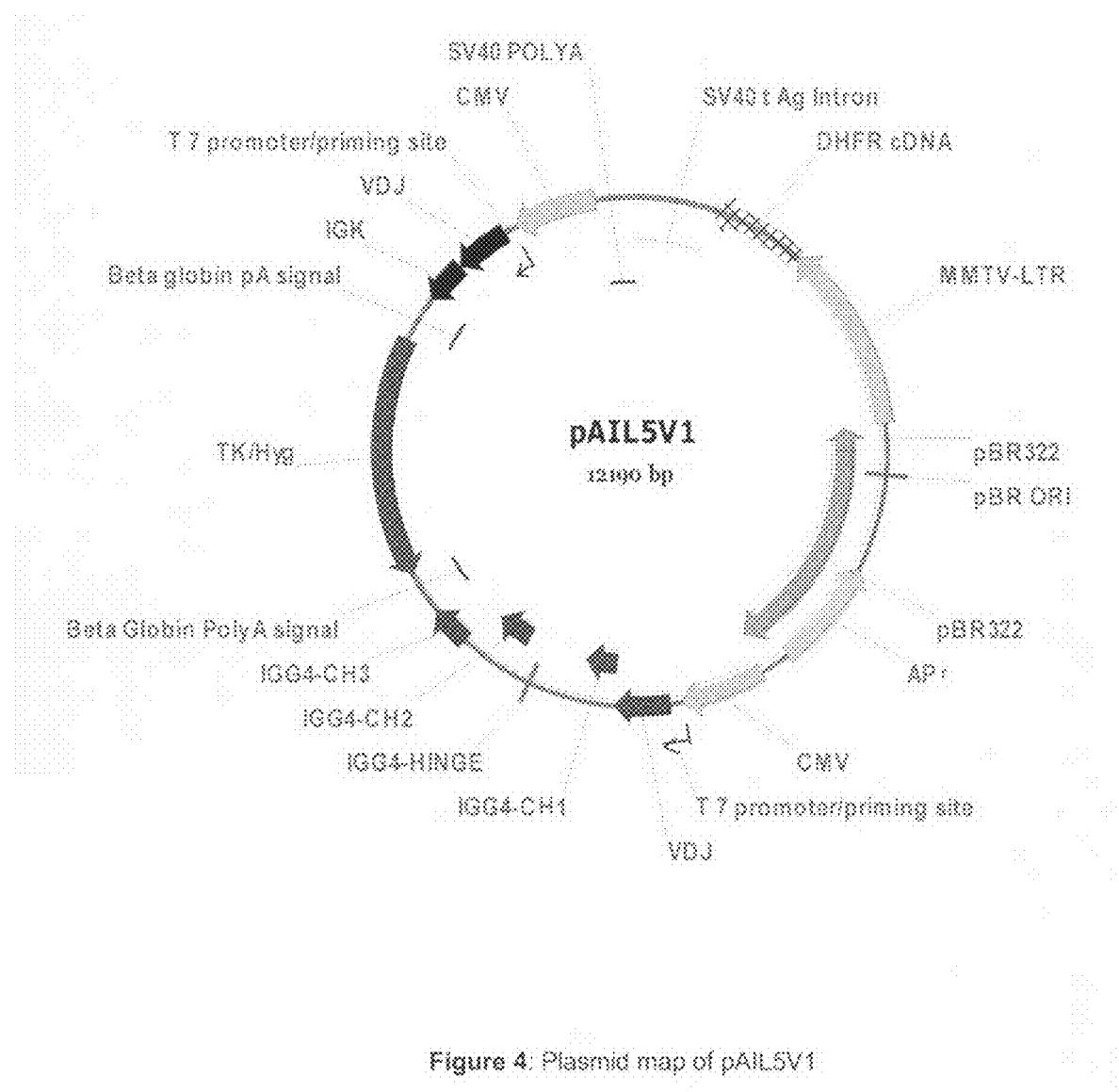
Figure 4: Plasmid map of pAIL5V1

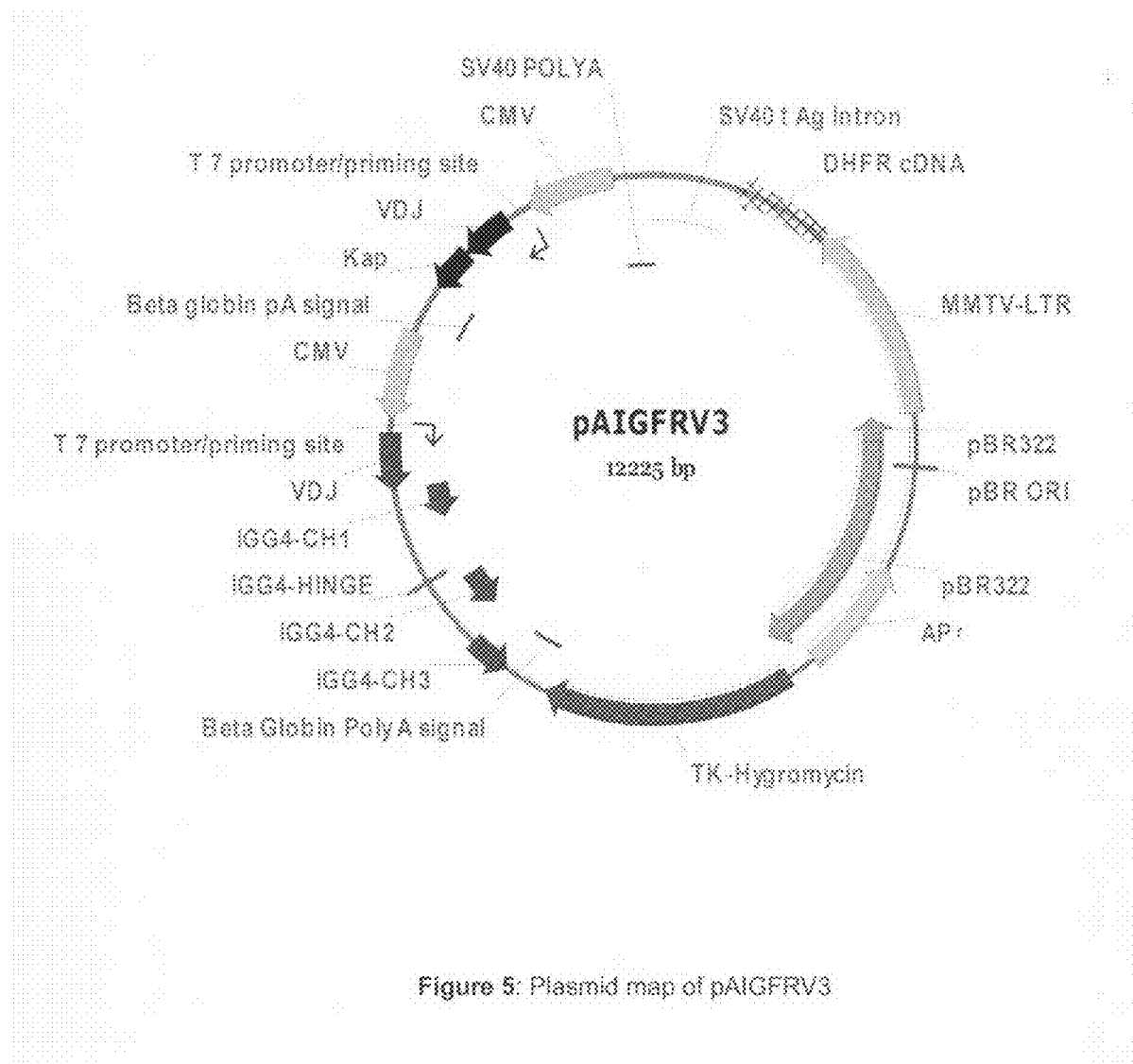
Figure 5: Plasmid map of pAIGFRV3

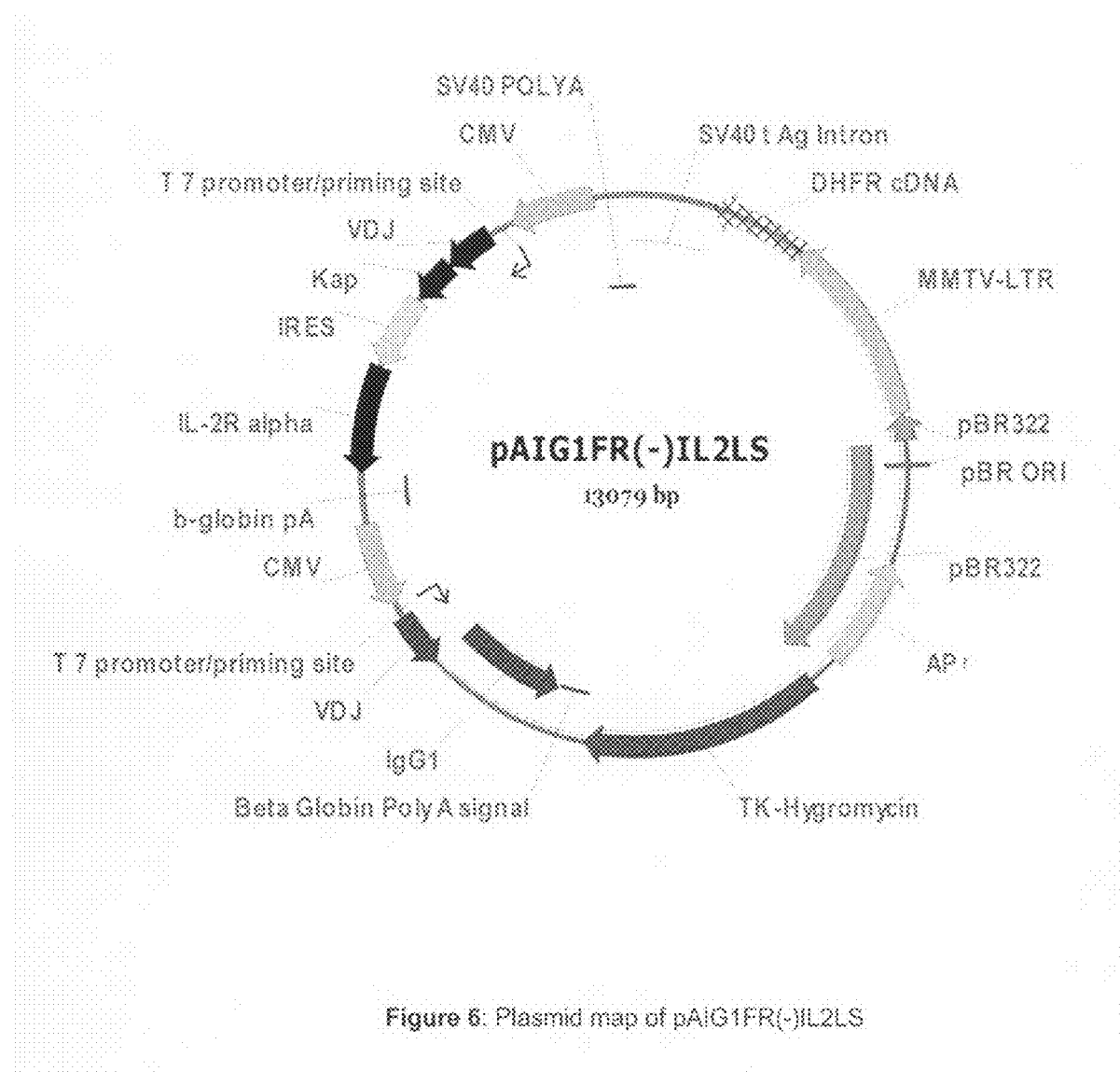
Figure 6: Plasmid map of pAIG1FR(-)IL2LS

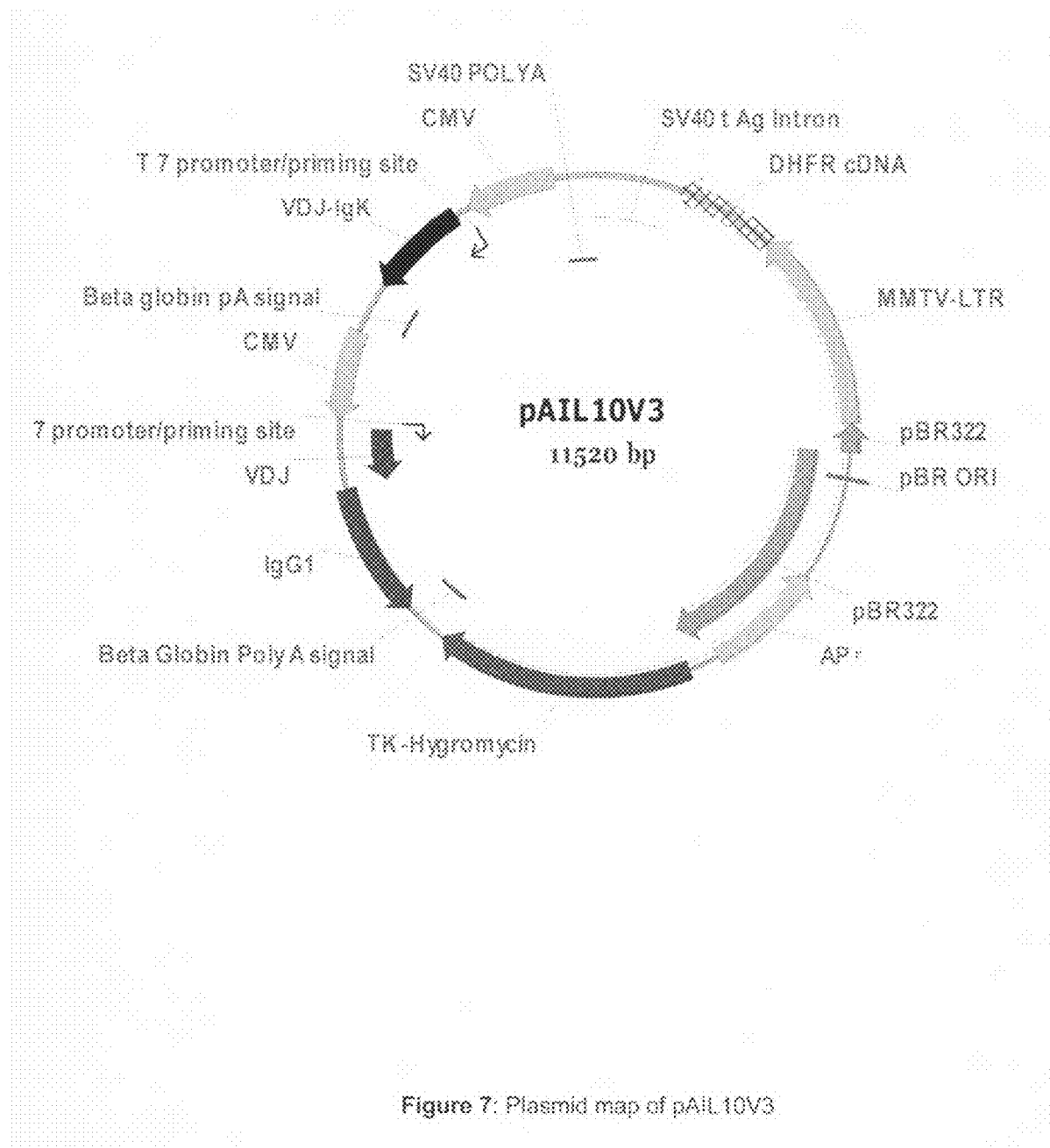
Figure 7: Plasmid map of pAIL10V3

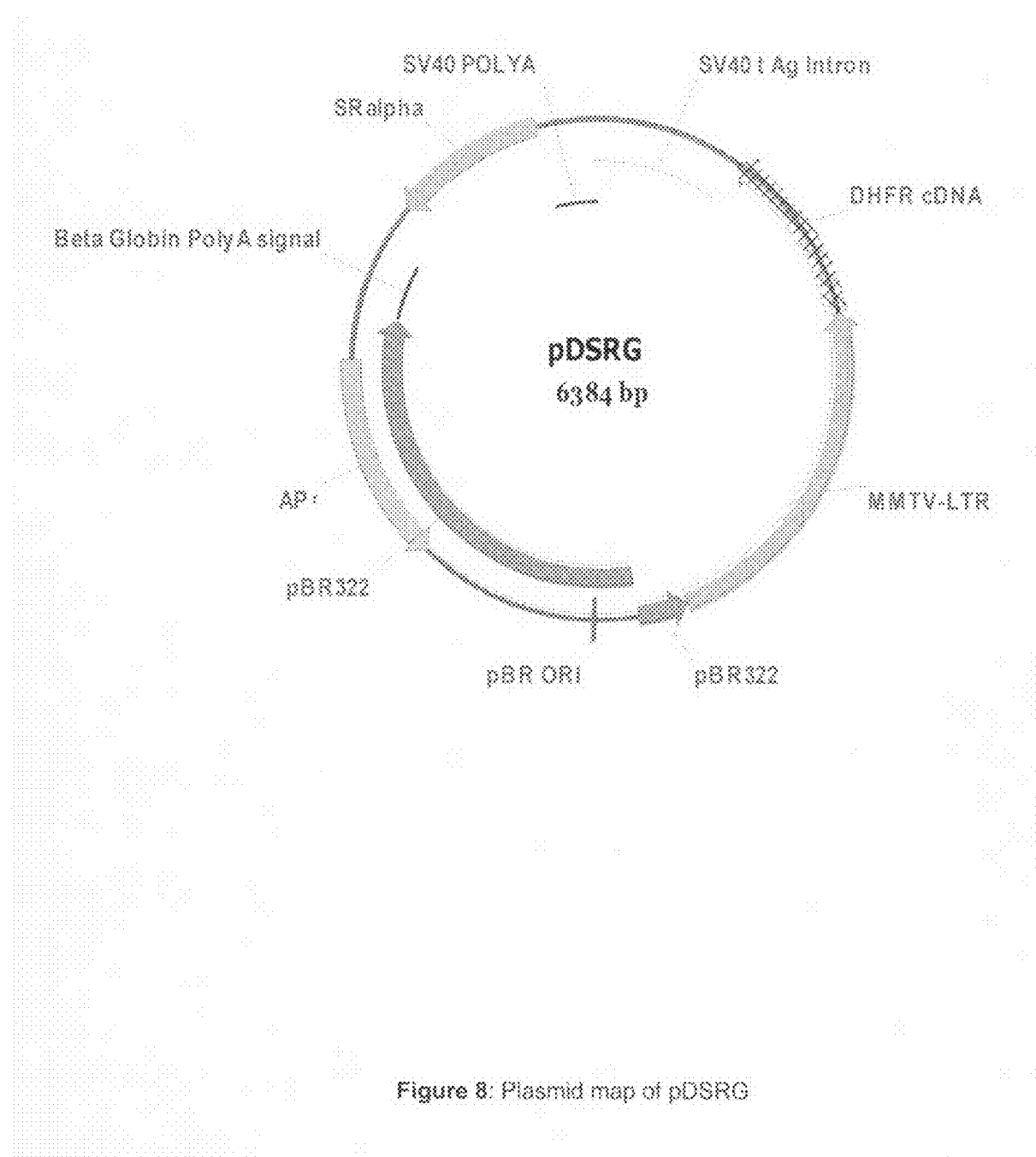
Figure 8: Plasmid map of pDSRG

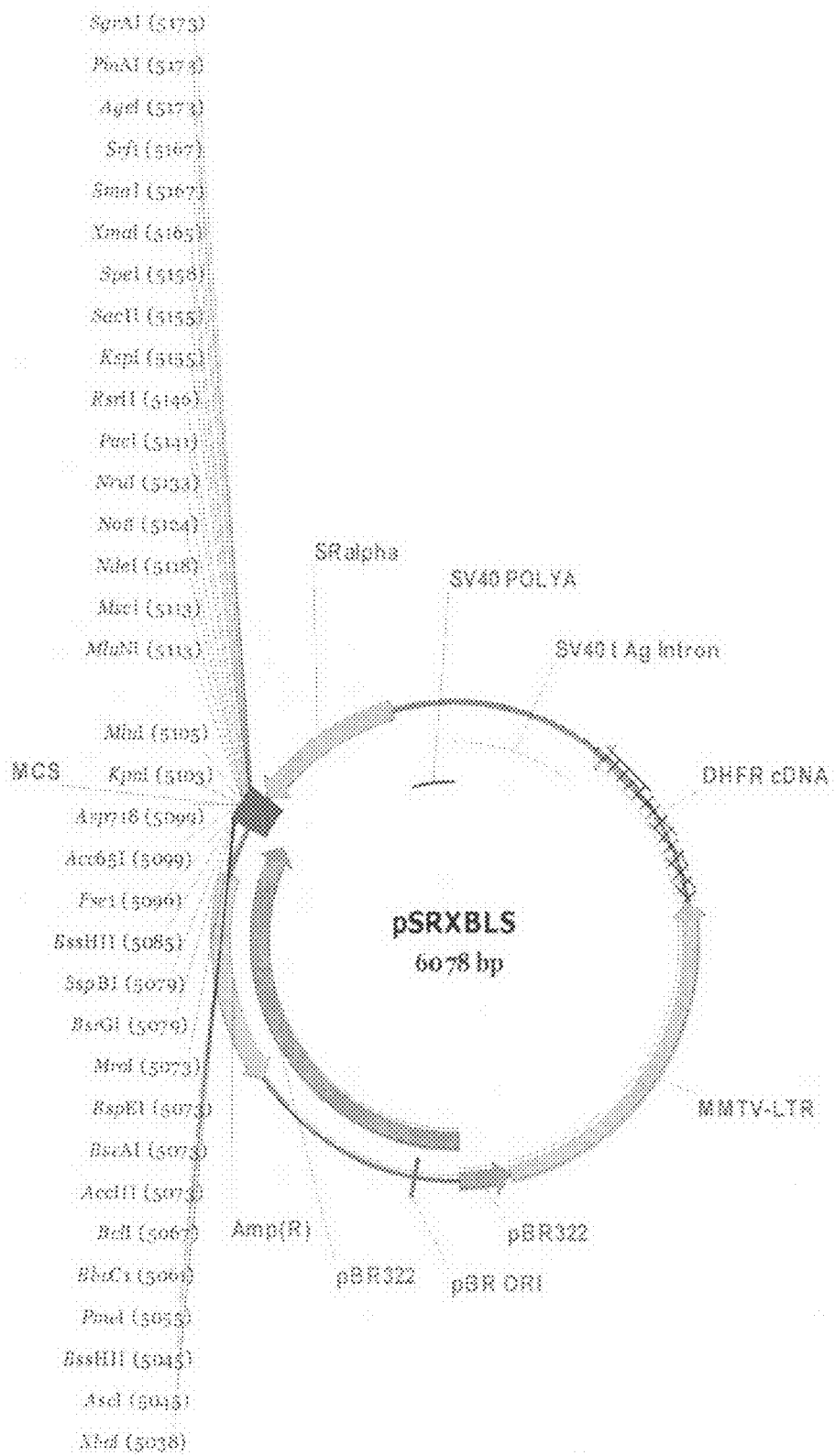
Figure 9: Plasmid map of pSRXBLS

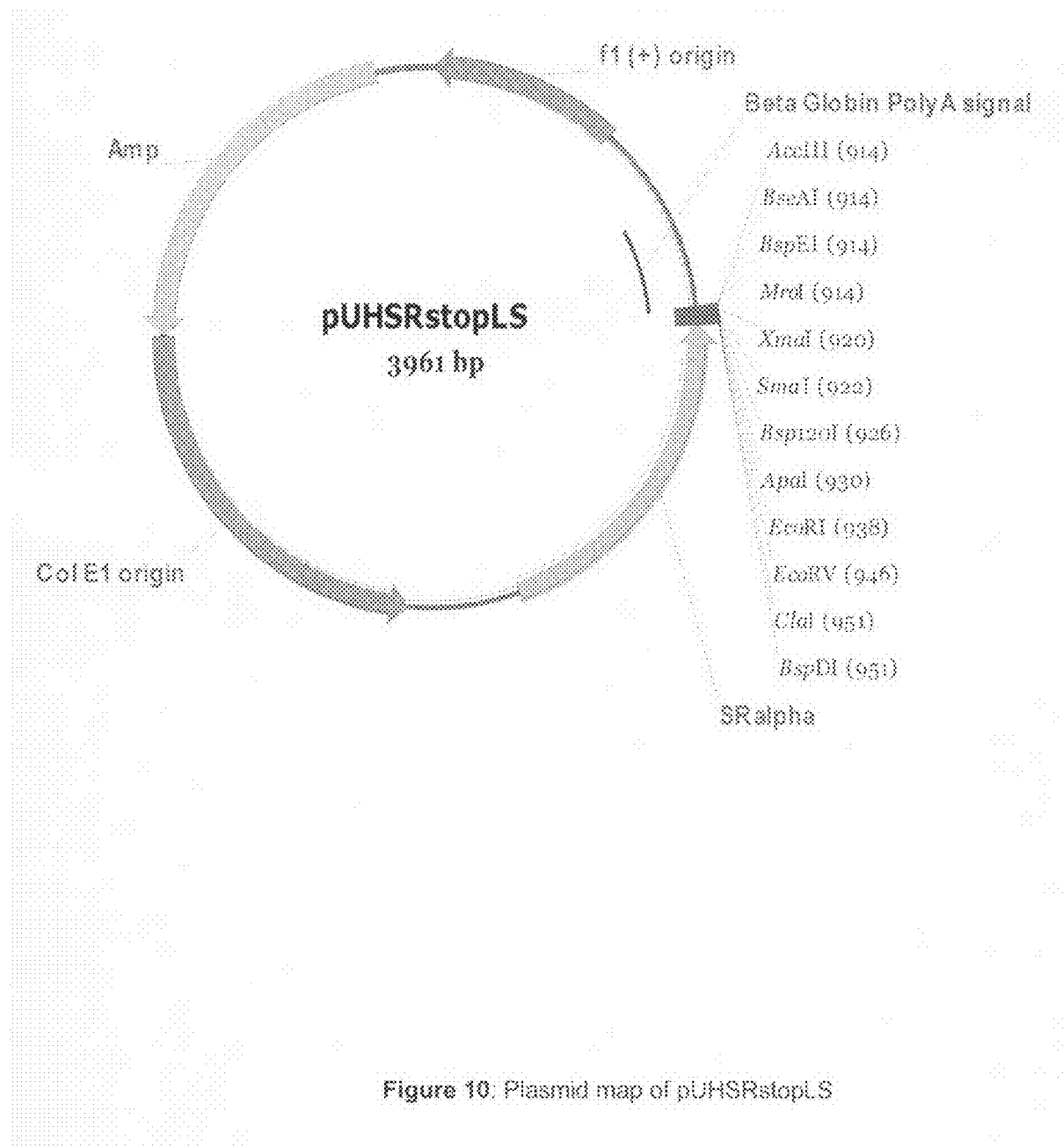
Figure 10: Plasmid map of pUHSRstopLS

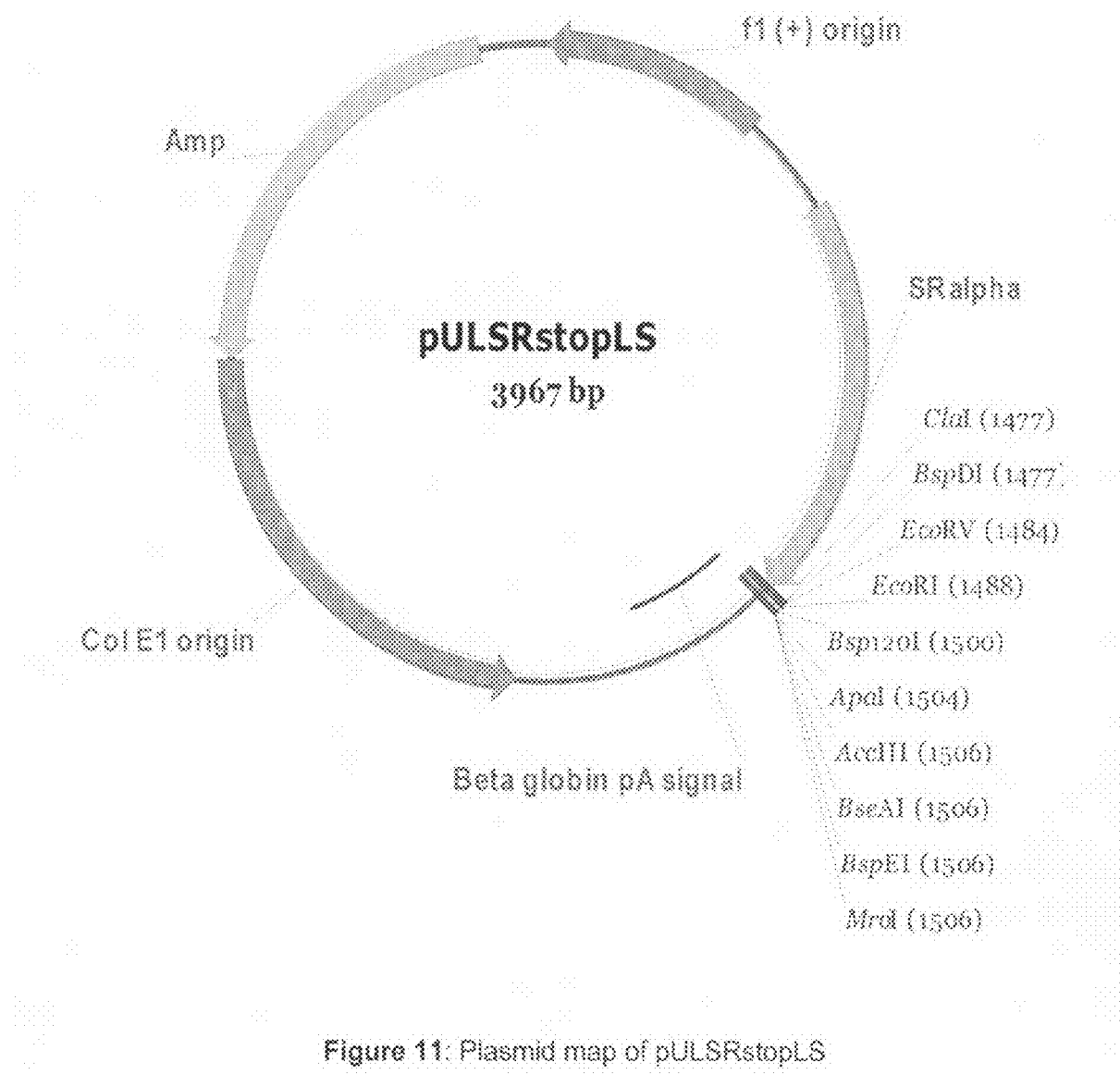
Figure 11: Plasmid map of pULSRstopLS

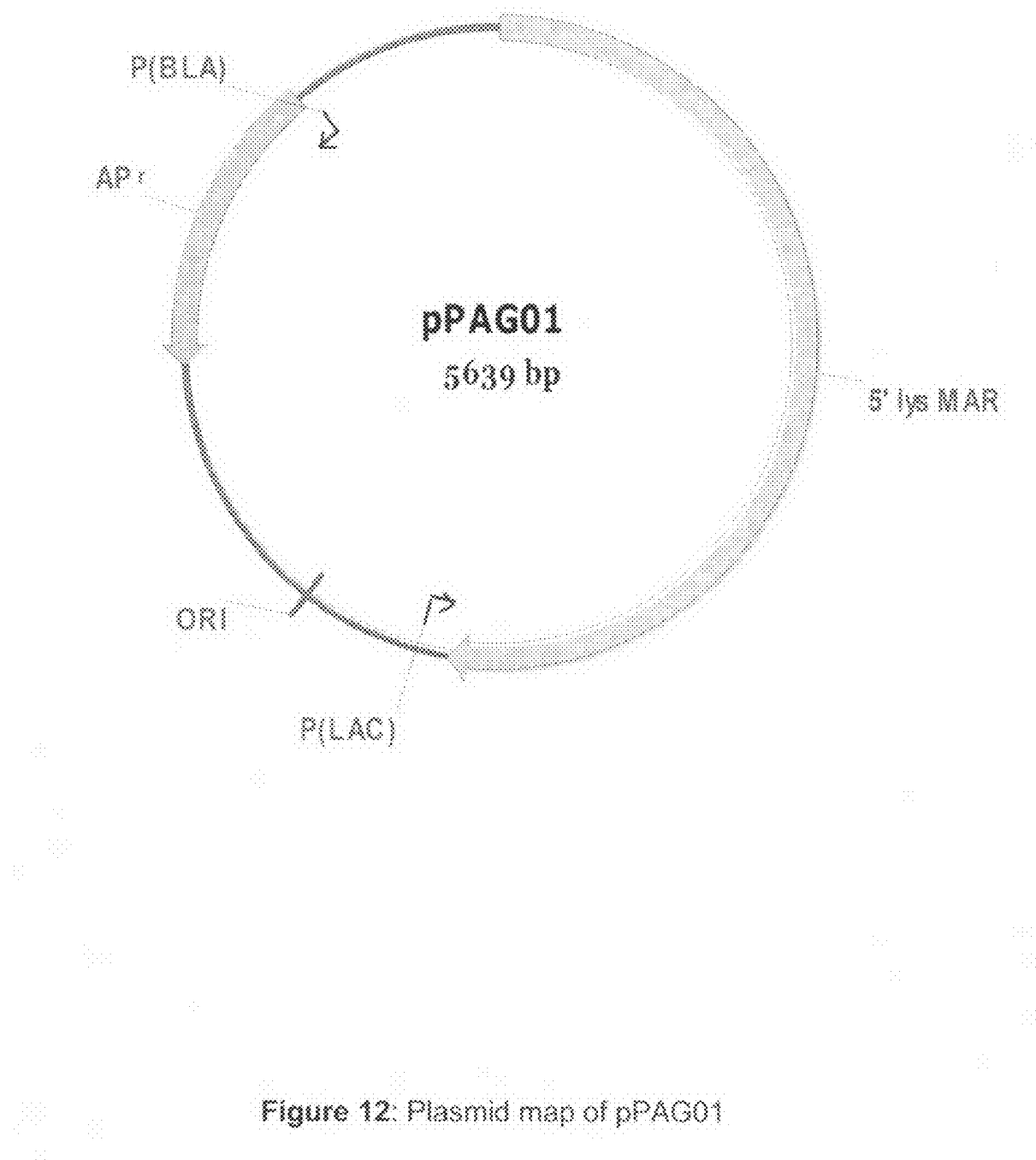
Figure 12: Plasmid map of pPAG01

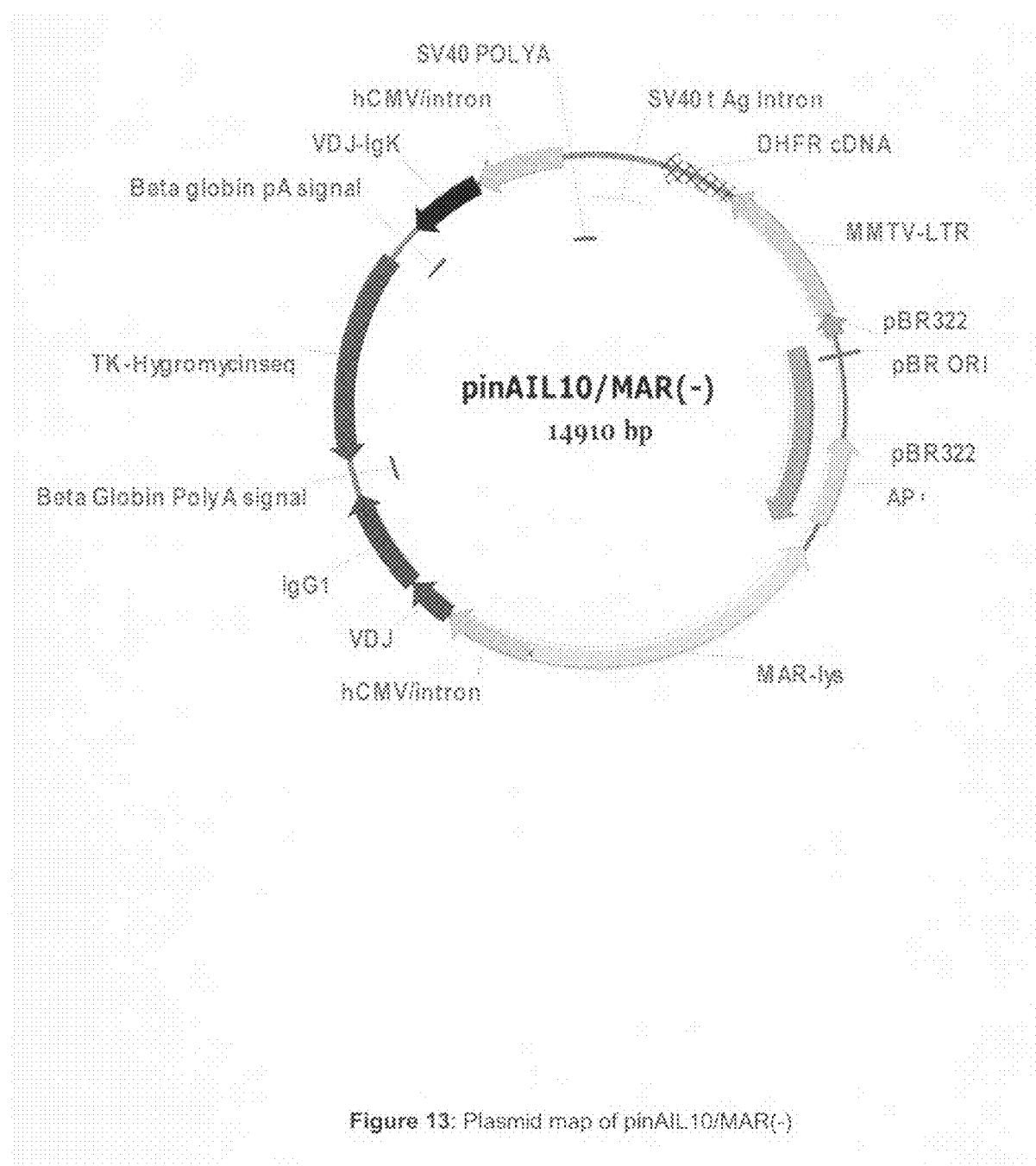
Figure 13: Plasmid map of pinAIL10/MAR(-)

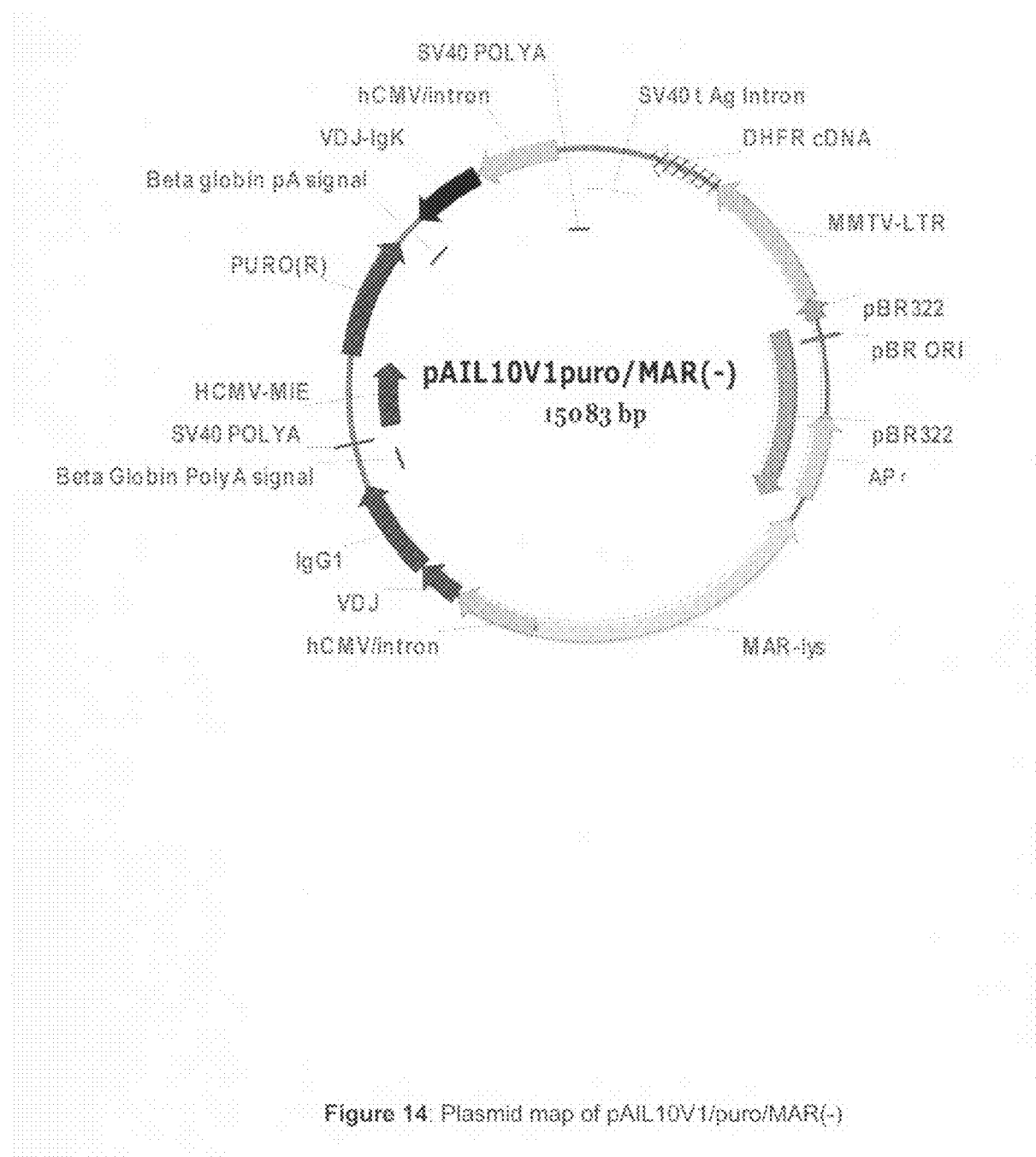
Figure 14. Plasmid map of pAIL10V1/puro/MAR(-)

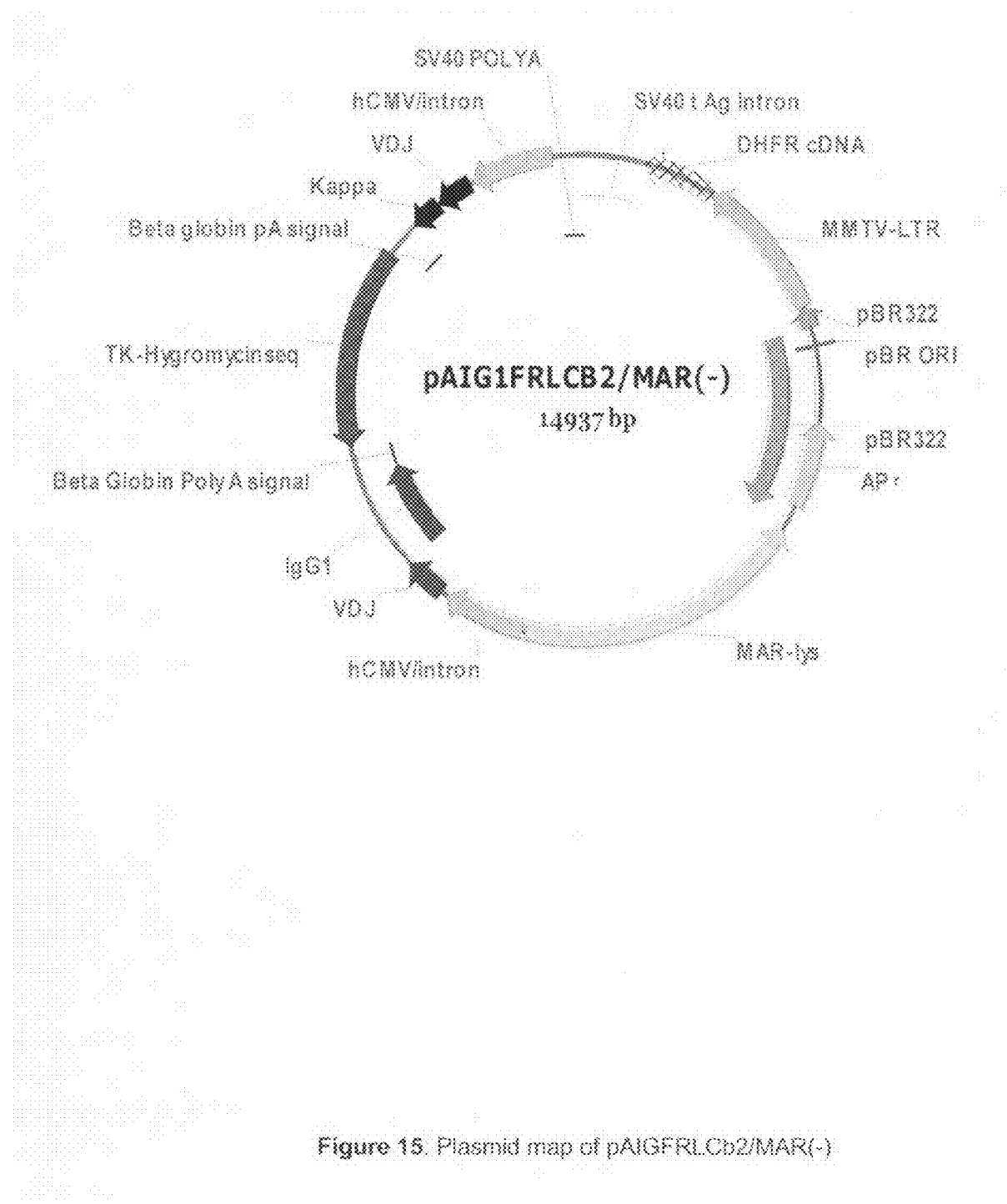
Figure 15. Plasmid map of pAIGFRLCb2/MAR(-)

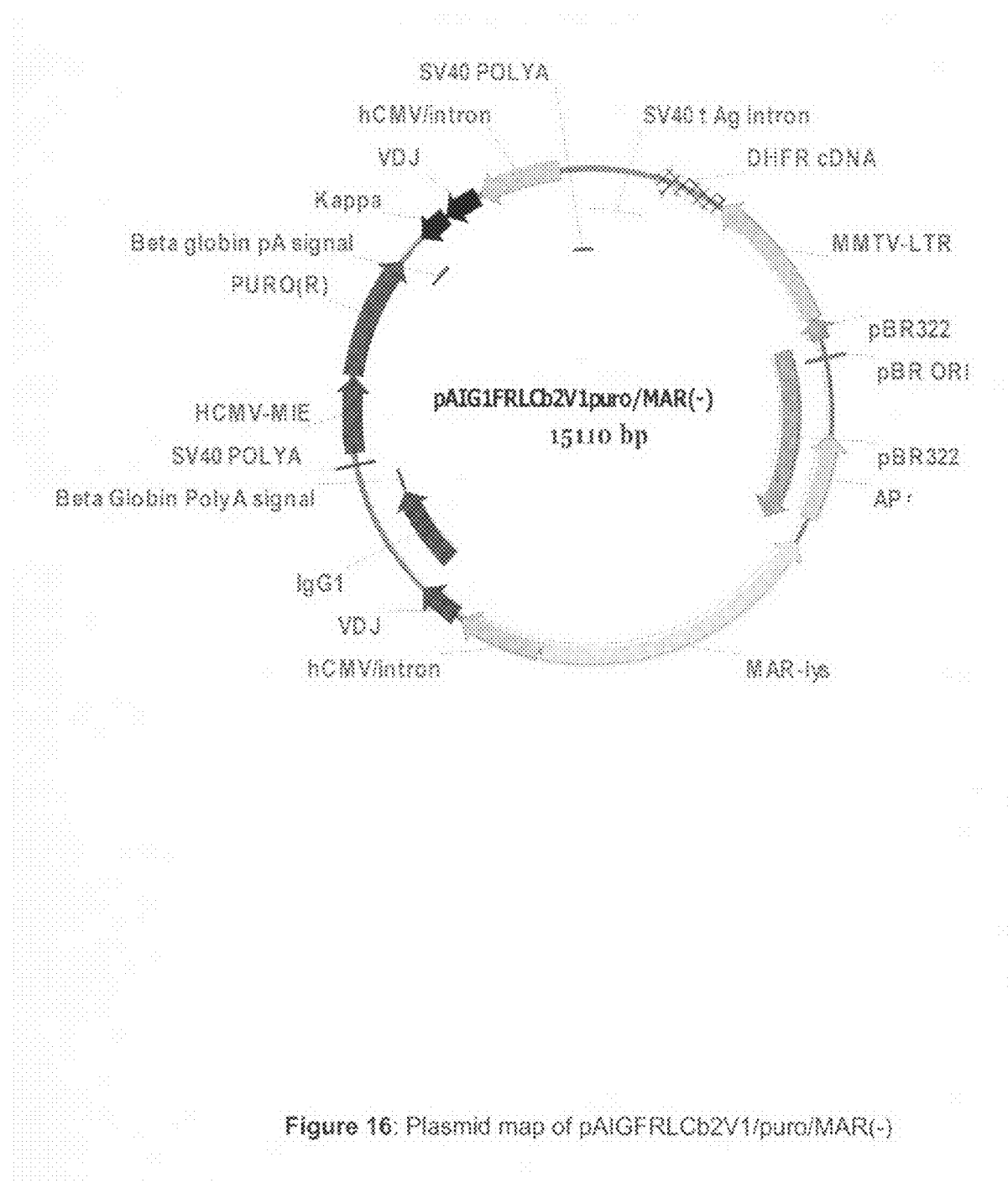
Figure 16: Plasmid map of pAIGFRLCb2V1/puro/MAR(-)

PLASMID SYSTEM FOR MULTIGENE EXPRESSION

This application is a continuation of U.S. patent application Ser. No. 10/986,498, filed Nov. 10, 2004; which claims the benefit of U.S. Provisional Patent Application No. 60/519,230, filed Nov. 12, 2003; each of which is herein incorporated by reference in its entirety.

FIELD OF THE INVENTION

A plasmid system which facilitates construction of a single amplifiable expression plasmid for multi-subunit proteins.

BACKGROUND OF THE INVENTION

Development of any mammalian cell based protein therapeutic requires an efficient expression system. Ideally, if a multi-subunit protein (e.g., an antibody) must be produced, each polypeptide should be expressed from a single plasmid. Construction of expression vectors containing multiple genes, using commercially available expression plasmids, is problematic. Typically, the multiple cloning sites (MCS), of currently available expression plasmids, are inadequate for insertion of multiple expression cassettes. The multiple cloning sites of currently available expression plasmids contain relatively few restriction sites. Ideally, an expression plasmid for expression of multiple polypeptides would contain a large multiple cloning site containing many common and rare restriction sites.

The present invention provides, inter alia, an ideal generic plasmid expression system which can help maintain uniformity in vector construction, decrease variability in downstream processing, facilitate running multiple protein therapeutic projects simultaneously, and reduce cycle time significantly. The present invention includes such a generic plasmid platform for mammalian expression and its use for the production of various polypeptides. The platform is flexible enough to be used for expression of simple proteins, such as interferon, as well as large, complex, multi-subunit proteins, such as antibodies.

SUMMARY OF THE INVENTION

The present invention provides a plasmid system comprising in separate containers:
(a) a first universal transfer vector comprising the following, first multiple cloning site: Bss HII, Pme I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam H1, Dsa I, Eag I, Ecl XI, Not I, Sac II, Xma III, Xba I, Sac I, Mlu I, Bcl I, Bsr GI, Bss HII; (b) a second universal transfer vector comprising the following, second multiple cloning site: Bss HII, Sgr AI, Xma I, Rsr II, Spe I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Bsp EI, Bam H1, Dsa I, Eag I, Ecl XI, Not I, Sac II, Xma III, Xba I, Sac I, Nde I, Msc I, Nru I, Pac I, Bss HII; and (c) an amplifiable vector comprising the following, third multiple cloning site: Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv C1, Pme I, Bss HII, Asc I, Xba I. In an embodiment of the invention, the plasmid system comprises: a first universal transfer vector comprising the plasmid map of FIG. 2, a second universal transfer vector comprising the plasmid map of FIG. 1 and an amplifiable vector comprising the plasmid map of FIG. 3. In another embodiment, the multiple cloning site of the first universal transfer vector comprises the nucleotide sequence set forth in SEQ ID NO: 11; the multiple cloning site of the second universal transfer vector comprises the nucleotide sequence set forth in SEQ ID NO: 12; and the multiple cloning site of the amplifiable vector comprises the nucleotide sequence set forth in SEQ ID NO: 10. In an embodiment of the invention, any of the universal transfer vectors or the amplifiable vector comprises a matrix attachment region (MAR; e.g., chicken lysozyme MAR).

In another embodiment of the invention, the plasmid system comprises only the first and second universal transfer vectors (supra).

In an embodiment of the invention, at least one of the plasmids comprises a promoter (e.g., SRα promoter, MMTV LTR, human cytomegalovirus (hCMV) immediate early promoter and murine cytomegalovirus (mCMV) immediate early promoter) located upstream of or within the multiple cloning site. Preferably, in this embodiment, the first universal transfer vector comprises the plasmid map of FIG. 10; the second universal transfer vector comprises the plasmid map of FIG. 11; and the amplifiable vector comprises the plasmid map of FIG. 9. In this embodiment, the first universal transfer vector can comprise the nucleotide sequence set forth in SEQ ID NO: 5; the second universal transfer vector comprise the nucleotide sequence set forth in SEQ ID NO: 4; and the amplifiable vector comprises the nucleotide sequence set forth in SEQ ID NO: 13.

Another embodiment of the present invention includes the plasmid system wherein at least one of the universal transfer vectors comprises a terminator/polyA addition site located in the multiple cloning site wherein the location of the terminator/polyA addition site is such that a gene located in the multiple cloning site would be operably linked to the terminator/polyA addition site.

The amplifiable vector in the plasmid system of the invention may comprise a selectable marker for amplification, such as the DHFR gene.

In an embodiment of the invention, the plasmid system of the present invention comprises in separate containers: (a) a first universal transfer vector comprising the nucleotide sequence set forth in SEQ ID NO: 2; (b) a second universal transfer vector comprising the nucleotide sequence set forth in SEQ ID NO: 1; and (c) an amplifiable vector comprising the nucleotide sequence set forth in SEQ ID NO: 3.

An embodiment of the invention includes a plasmid system wherein the first or second universal transfer vector comprises a first set of one or more expression cassettes, the other universal transfer vector comprise a second set of one or more expression cassettes and the amplifiable vector comprises said first set and second set of expression cassettes; wherein the expression cassettes encode an immunoglobulin heavy chain and an immunogloblin light chain (e.g., anti-IGFR1, anti-IL10 or anti-IL5 immunoglobulin chains); for example wherein (a) the first set of one or more expression cassettes comprises an anti-IL5 immunoglobulin heavy chain gene expression cassette and the second set of one or more expression cassettes comprises an anti-IL5 immunoglobulin light chain gene expression cassette; (b) the first set or one or more expression cassette comprises an anti-IGFR1 immunoglobulin heavy chain gene expression cassette and the second set of one or more expression cassette comprises an anti-IGFR1 immunoglobulin light chain gene expression cassette; (c) the first set of one or more expression cassettes comprises an expression cassette comprising a bicistronic gene expression cassette which bicistronic gene comprises an anti-IGFR1 immunoglobulin light chain gene and an IL2 receptor α gene wherein said genes are linked by an internal ribosome entry sequence (IRES) and the second set of one or more expression cassettes is an anti-IGFR1 immunoglobulin heavy chain gene expression cassette and a hygromycin resistance gene (Hygb) expression cassette; or (d) the first set of one or more expression cassettes comprises an anti-IL10 immunoglobulin heavy chain gene expression cassette and the second set of one or more expression cassettes comprises an anti-IL10 immunoglobulin light chain gene expression cassette and a hygromycin resistance gene expression cassette. In an embodiment of the invention, the amplifiable vector comprises a plasmid map as set forth in a figure selected from FIGS. 4-7. For example, the amplifiable vector can comprise a nucleotide sequence selected from SEQ ID NOs: 6-9.

In an embodiment of the present invention, the plasmid system includes the amplifiable vectors pinAIL10/MAR(−); pAIL10V1/puro/MAR(−); pAIGFRLCb2/MAR(−) or pAIGFRLCb2V1/puro/MAR(−). In an embodiment of the invention, the plasmids pinAIL10/MAR(−); pAIL10V1/puro/MAR(−); pAIGFRLCb2/MAR(−) and pAIGFRLCb2V1/puro/MAR(−) are characterized by FIGS. 13-16, respectively. In another embodiment of the invention, the plasmids pinAIL10/MAR(−); pAIL10V1/puro/MAR(−); pAIGFRLCb2/MAR(−) and pAIGFRLCb2V1/puro/MAR(−) comprise a nucleotide sequence selected from SEQ ID NOs: 24-27.

The present invention also provides a method for expressing a protein comprising two or more types of polypeptide comprising the steps of (a) introducing a set of one or more expression cassettes into a first universal transfer vector; (b) introducing one or more different expression cassettes into a second universal transfer vector; (c) moving the cassettes from the transfer vectors into an amplifiable vector; (d) causing expression of said cassettes; and (e) optionally, isolating/purifying the polypeptide; wherein said vectors are provided in a kit of the present invention. In one embodiment of the invention, the first universal transfer vector comprises the plasmid map of FIG. 2 or FIG. 10, or the nucleotide sequence set forth in SEQ ID NO: 2 or SEQ ID NO: 5. In another embodiment, the second universal transfer vector comprises the plasmid map of FIG. 1 or FIG. 11 or the nucleotide sequence set forth in SEQ ID NO: 1 or SEQ ID NO: 4. In another embodiment of the invention, the amplifiable vector comprises the plasmid map of FIG. 3 or FIG. 9 or the nucleotide sequence set forth in SEQ ID NO: 3 or SEQ ID NO: 13.

In an embodiment of the method, an anti-IGFR heavy chain or anti-IL10 heavy is expressed in an amplifiable vector, comprising a MAR and either the hygromycin resistance gene or the puromycin resistance gene, which selected from pinAIL10/MAR(−); pAIL10V1/puro/MAR(−); pAIGFRLCb2/MAR(−) and pAIGFRLCb2V1/puro/MAR(−). In an embodiment of the invention, the plasmids pinAIL10/MAR(−); pAIL10V1/puro/MAR(−); pAIGFRLCb2/MAR(−) and pAIGFRLCb2V1/puro/MAR(−) are characterized by FIGS. 13-16, respectively. In another embodiment of the invention, the plasmids pinAIL10/MAR(−); pAIL10V1/puro/MAR(−); pAIGFRLCb2/MAR(−) and pAIGFRLCb2V1/puro/MAR(−) comprise a nucleotide sequence selected from SEQ ID NOs: 24-27.

In an embodiment of the method for expressing a protein comprising two or more types of polypeptide, the expression cassettes encode an immunoglobulin heavy or light chain (e.g., anti-IGFR1, anti-IL5 or anti-IL10 immunoglobulin chain); for example: (i) one expression cassette encodes an anti-IL5 immunoglobulin heavy chain and the other expression cassette encodes an anti-IL5 immunoglobulin light chain; (ii) one expression cassette encodes an anti-IGFR1 immunoglobulin heavy chain (e.g., SEQ ID NO: 17 or 21 or any polynucleotide encoding a polypeptide comprising the amino acid sequence of SEQ ID NO: 18 or 22) and the other expression cassette encodes an anti-IGFR1 immunoglobulin light chain (e.g., SEQ ID NO: 15 or 19 or any polynucleotide encoding a polypeptide comprising the amino acid sequence of SEQ ID NO: 16 or 20); (iii) one expression cassette comprises a bicistronic gene encoding an anti-IGFR1 immunoglobulin light chain and an IL2 receptor α-subunit which are linked by an internal ribosome entry sequence (IRES) and the other expression cassette encodes an anti-IGFR1 immunoglobulin heavy chain and HYG-B; or (iv) one expression cassettes encodes an anti-IL10 immunoglobulin heavy chain and the other expression cassette encodes an anti-IL10 immunoglobulin light chain and HYG-B.

In an embodiment of the invention, the amplifiable vector comprises a plasmid map in a figure selected from FIGS. 4-7. The amplifiable vector may comprise a nucleotide sequence selected from SEQ ID NOs: 6-9.

The scope of the present invention also encompasses any product produced by any of the methods of the invention for producing a polypeptide (e.g., any immunoglobulin chain, such as that of an anti-IGFR1, anti-IL5 or anti-IL10 antibody).

In an embodiment of the method for expressing a protein comprising two or more types of polypeptide, expression is caused in a cell (e.g., a eukaryotic cell such as a CHO cell).

The present invention also comprises a method for producing an anti-IGFR1 antibody comprising the steps of (a) introducing an expression cassette comprising a polynucleotide encoding a polypeptide comprising an amino acid sequence selected from SEQ ID NOs: 18 and 22 or an expression cassette comprising a polynucleotide encoding a polypeptide comprising an amino acid sequence selected from SEQ ID NOs: 16 and 20 into a first universal transfer vector comprising the following, first multiple cloning site: Bss HII, Pme I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam H1, Dsa I, Eag I, Ecl XI, Not I, Sac II, Xma III, Xba I, Sac I, Mlu I, Bcl I, Bsr GI, Bss HII (e.g., pUHLS or PUHSRstopLS); (b) introducing the other expression cassette, not introduced into said first vector, into a second universal transfer vector comprising the following, second multiple cloning site: Bss HII, Sgr AI, Xma I, Rsr II, Spe I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Bsp EI, Bam H1, Dsa I, Eag I, Ecl XI, Not I, Sac II, Xma III, Xba I, Sac I, Nde I, Msc I, Nru I, Pac I, Bss HII (e.g., pULLS or PULSRstopLS); (c) optionally, moving the cassettes from the transfer vectors into an amplifiable vector comprising the following, third multiple cloning site: Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv C1, Pme I, Bss HII, Asc I, Xba I (e.g., pXBLS or pSRXBLS); (d) causing expression of said cassettes; and (e) optionally isolating/purifying the antibody. The polynucleotide encoding a polypeptide comprising an amino acid sequence selected from SEQ ID NOs: 18 and 22 can comprise a nucleotide sequence selected from SEQ ID NOs: 17 and 21. The polynucleotide encoding a polypeptide comprising an amino acid sequence selected from SEQ ID NOs: 16 and 20 can comprise a nucleotide sequence selected from SEQ ID NOs: 15 and 19. In one embodiment of the invention, the expression cassettes are operably linked to a human cytomegalovirus (hCMV) promoter. The scope of the present invention includes embodiments wherein the expression cassettes mentioned above are linked to an immunoglobulin constant region such as that of any one of κ or γ1 or γ2 or γ3 or γ4.

The present invention also provides a kit comprising the plasmid system of the invention and one or more components selected from: (i) sterile, distilled water; (ii) calcium phosphate transformation reagents CaCl$_2$ and 2×HEPES buffered saline; (iii) DEAE-dextran transformation reagents chloroquine in Phosphate buffered saline and phosphate buffered saline; (iv) DOTAP/cholesterol extruded liposomes; (v) transformation competent *E. coli*; (vi) Dulbecco/Vogt modified Eagle's minimal essential medium (DMEM); (vii) Fetal calf serum; (viii) luria broth media; and (ix) paper instructions for usage of the plasmid system.

One embodiment of the present invention includes a single stranded or double stranded polynucleotide (e.g., an oligonucleotide primer) comprising a nucleotide sequence of SEQ ID NO: 10, 11 or 12.

The present invention also includes a plasmid comprising a nucleotide sequence selected from the group consisting of SEQ ID NOs: 6-9.

BRIEF DESCRIPTION OF THE FIGURES

The scope of the present invention includes any plasmid or plasmid system containing a plasmid that comprises a plasmid map substantially identical to any of the following plasmid maps:

FIG. 4. Plasmid map of pAIL5V1.
The anti-IL-5 antibody heavy (VDJ-IgG4) and light (VDJ-IgK) chain expression cassettes, driven by the CMV promoter, are inserted into the multiple cloning site of pXBLS along with the hygromycin B expression cassette driven by the TK promoter (TK/Hyg).
SV40 t Ag Intron: Start: 12177 End: 600
SV40 POLYA signal: Start: 11930 End: 12178
CMV Promoter: Start: 11238 End: 11892
T 7 promoter/priming site: Start: 11219 End: 11238
VDJ (Anti-IL-5 light chain): Start: 10718 End: 11148
IGκ (Anti-IL-5 light chain): Start: 10382 End: 10717
Beta Globin Poly A signal: Start: 10126 End: 10374
TK/Hyg: Start: 8161 End: 10033
Beta Globin Poly A signal: Start: 7877 End: 8115
IGG4-CH3 (Anti-IL-5 antibody heavy chain): Start: 7517 End: 7834
IGG4-CH2 (Anti-IL-5 antibody heavy chain): Start: 7087 End: 7419
IGG4-HINGE (Anti-IL-5 antibody heavy chain): Start: 6933 End: 6968
IGG4-CH1 (Anti-IL-5 antibody heavy chain): Start: 6247 End: 6540
VDJ (Anti-IL-5 antibody heavy chain): Start: 5813 End: 6247
T 7 promoter/priming site: Start: 5723 End: 5742
CMV Promoter: Start: 5069 End: 5723
AP$^r$ (Ampicillin resistance): Start: 3965 End: 4828
PBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347

FIG. 5. Plasmid map of pAIGFRV3.
The anti-IGFR1 antibody heavy (VDJ-IgG4) and light (VDJ-IgK) chain expression cassettes, driven by the CMV promoter, are inserted into the multiple cloning site of pXBLS along with the hygromycin B expression cassette driven by the TK promoter (TK-Hygromycin). The DHFR cDNA, along with its promoter (MMTV-LTR) for plasmid amplification and the hygromycin B coding sequence, along with its TK promoter for selection in mammalian cells, are shown.
AP(R): Start: 3965 End: 4828
IgG1 non genomic region: Start: 7234 End: 8214
VDJ of IGFR1 of 11D8 hybridoma: Start: 8214 End: 8641
DHFR cDNA: Start: 601 End: 1347
SV40 t Ag Intron: Start: 11603 End: 600
Kappa chain of hu-antiIGFR gene: Start: 9761 End: 10096
VDJ Domain of hu-anti IGFR gene for light chain: Start: 10097 End: 10477
pBR322 sequence: Start: 2811 End: 3019
pBR322 sequence: Start: 3020 End: 5033
TK-Hygromycin: Start: 5053 End: 6925
Beta Globin Poly A signal: Start: 6971 End: 7209
Beta globin pA signal: Start: 9505 End: 9753
SV40 POLYA: Start: 11356 End: 11604
MMTV-LTR: Start: 1348 End: 2810
CMV promoter: Start: 10664 End: 11318
T 7 promoter/priming site: Start: 8723 End: 8742
CMV promoter: Start: 8742 End: 9396
T 7 promoter/priming site: Start: 10645 End: 10664
pBR ORI: Start: 3207 End: 3207

FIG. 6. Plasmid map of pAIG1FR(–)IL2LS.
This plasmid drives expression of the anti-IGFR1 antibody and the membrane domain of the IL2 receptor. Three independent expression cassettes containing four genes including heavy and light chain anti-IGFR1, truncated IL2 receptor and hygromycin B are incorporated into the multiple cloning site of pXBLS.
SV40 t Ag Intron: Start: 13066 End: 600
SV40 POLYA: Start: 12819 End: 13067
CMV: Start: 12115 End: 12769
T7 promoter/priming site: Start: 12096 End: 12115
VDJ (Anti-IGFR1 light chain): Start: 11548 End: 11928
Kappa (Kap; Anti-IGFR1 light chain): Start: 11212 End: 11547
IRES: Start: 10621 End: 11195
IL-2R alpha: Start: 9787 End: 10615
Beta Globin Poly A signal (β-globin pA) Start: 9505 End: 9753
CMV: Start: 8742 End: 9396
T7 promoter/priming site: Start: 8723 End: 8742
VDJ (Anti-IGFR1 heavy chain of 11D8 hybridoma): Start: 8214 End: 8641
IgG1 (Anti-IGFR1 heavy chain of 11D8 hybridoma): Start: 7234 End: 8214
Beta Globin Poly A signal (b-globin pA): Start: 6971 End: 7209
TK-Hygromycin: Start: 5053 End: 6925

Figure 1:
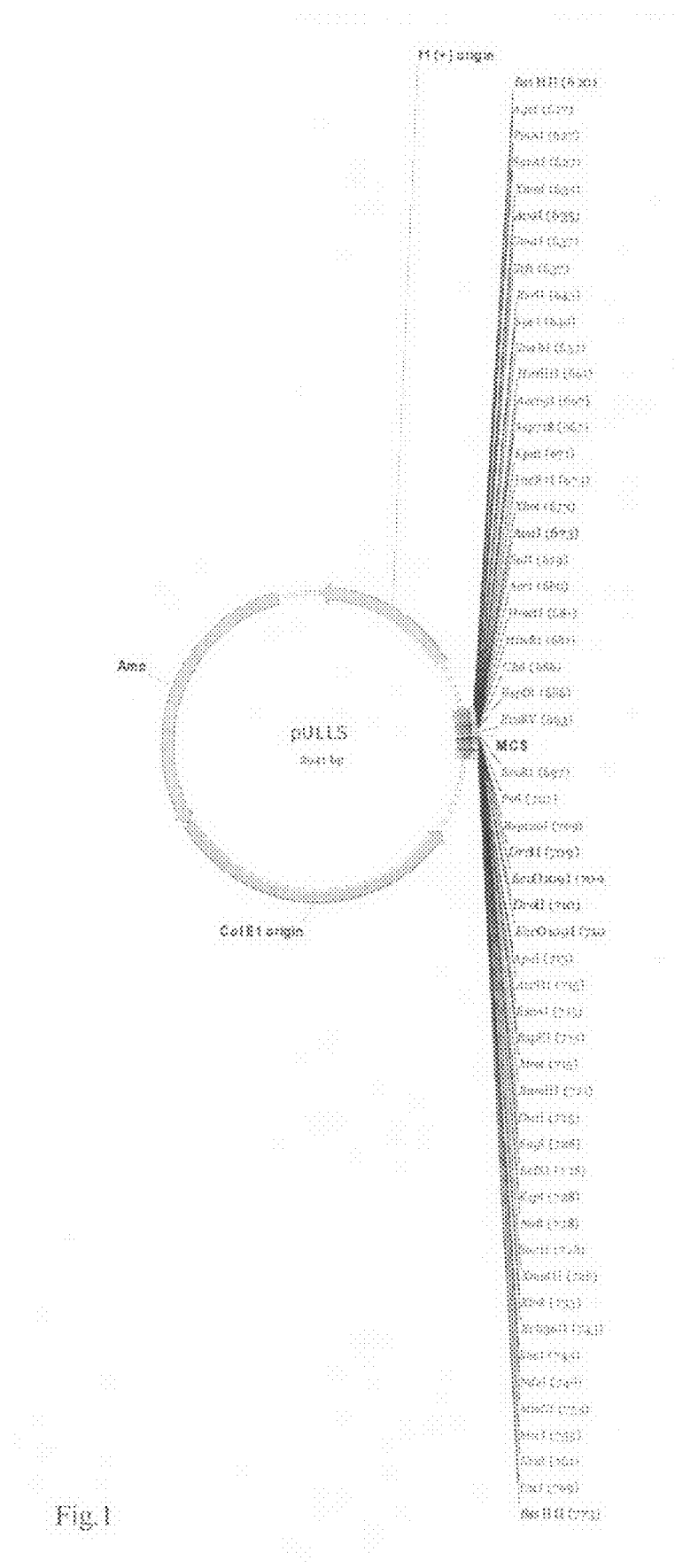
FIG. 1. Plasmid map of universal transfer vector pULLS.
Amp: Start: 1955 End: 2812
Col E1 origin: Start: 1012 End: 1952
Multiple Cloning Site (MCS): Start: 620 End: 772
f1 (+) origin: Start: 3 End: 459

Ap$^r$: Start: 3965 End: 4828
pBR ORI: Start: 3207 End: 3207
pBR322 sequences: Start: 3020 End: 5033
pBR322 sequences: Start: 2811 End: 3019
MMTV-LTR: Start: 1348 End: 2810
DHFR cDNA: Start: 601 End: 1347

FIG. 7. Plasmid map of pAIL10V3.

The plasmid drives expression of anti-IL10. The anti-IL10 antibody heavy (VDJ-IgG4) and light (VDJ-IgK) chain expression cassettes, driven by the CMV promoter, are inserted into the multiple cloning site of pXBLS along with the hygromycin B expression cassette driven by the TK promoter (TK-Hygromycin). The dhfr cDNA, along with its promoter (MMTV-LTR) for plasmid amplification and the hygromycin B coding sequence, along with its TK promoter for selection in mammalian cells, are shown.

SV40 t Ag Intron: Start: 11507 End: 600
SV40 POLYA signal: Start: 11260 End: 11508
CMV: Start: 10568 End: 11222
T7 promoter/priming site: Start: 10549 End: 10568
VDJ-IgK (anti-IL10 rat antibody 12G8 light chain): Start: 9739 End: 10468
Beta globin Poly A signal: Start: 9478 End: 9726
CMV promoter: Start: 8715 End: 9369
T7 promoter/priming site: Start: 8696 End: 8715
VDJ (anti-IL10 rat antibody 12G8 heavy chain): Start: 8214 End: 8644
IgG1 non genomic region (anti-IL10 rat antibody 12G8 heavy chain): Start: 7234 End: 8214
Beta Globin Poly A signal: Start: 6971 End: 7209
TK promoter driving Hygromycin gene (TK-Hygromycin): Start: 5053 End: 6925
AP$^r$: Start: 3965 End: 4828
pBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347

FIG. 8. Plasmid map of pDSRG.

This plasmid is deposited at the American Type Culture Collection (10801 University Boulevard; Manassas, Va. 20110-2209), under catalogue number 68233. The plasmid includes the SRα promoter, a strong SV40-based promoter and the dihydrofolate reductase (DHFR) cDNA for plasmid amplification in the presence of methotrexate in dhfr(−) Chinese hamster ovary (CHO) cells.

SV40 t Ag Intron: Start: 6371 End: 600
SV40 POLYA signal: Start: 6124 End: 6372
SRα promoter: Start: 5486 End: 6123
Beta Globin Poly A signal: Start: 5038 End: 5298
AP$^r$: Start: 3965 End: 4828
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347

FIG. 9. Plasmid map of pSRXBLS.

pSRXBLS is the direct descendent of pDSRG replacing its own multiple cloning site with a large multiple cloning site. pSRXBLS is the progenitor plasmid of pXBLS.

SV40 t Ag Intron: Start: 6065 End: 600
SV40 POLYA signal: Start: 5818 End: 6066
SRα promoter: Start: 5180 End: 5817
MCS: Start: 5038 End: 5179
Amp(R): Start: 3965 End: 4828
pBR ORI: Start: 3207 End: 3207
pBR322 sequences: Start: 3020 End: 5033 pBR322 sequences: Start: 2811 End: 3019
MMTV-LTR promoter: Start: 1348 End: 2810
DHFR cDNA: Start: 601 End: 1347.

FIG. 10. Plasmid map of pUHSRstopLS.

pUHSRstopLS is the descendent plasmid to pUHLS carrying the SRα promoter and 249 bp of chicken β-globin terminator. This plasmid alone can be used to express any gene of interest. Also, it can be used as a transfer vector to transfer a complete expression cassette of part of a complex protein to pXBLS where all the expression cassettes can be assembled on a single plasmid.

Amp: Start: 2975 End: 3832
Col E1 origin: Start: 2032 End: 2972
SRα promoter with Intron: Start: 955 End: 1764
Beta Globin Poly A signal: Start: 673 End: 911
f1 (+) origin: Start: 3 End: 459

FIG. 11. Plasmid map of pULSRstopLS.

pULSRstopLS is the descendent plasmid to pULLS carrying the SRα promoter and a 249 bp of chicken β-globin terminator. This plasmid alone can be used to express any gene of interest. Also, it can be used as a transfer vector to transfer a complete expression cassette of part of a complex protein to pXBLS where all the expression cassettes can be assembled on a single plasmid.

Amp: Start: 2981 End: 3838
Col E1 origin: Start: 2038 End: 2978
Beta globin poly A signal: Start: 1512 End: 1760
SRα promoter: Start: 665 End: 1474
f1 (+) origin: Start: 3 End: 459

FIG. 12. Plasmid map of pPAG01.

This plasmid contains Selexis's (Geneva, Switzerland) ~3 kb chicken lysozyme MAR, flanked by Xba1 and BamH1 site.

AP(R) (bla gene-Ap(r) determinant): Start: 4165 End: 5022
Selexis Inc. 5' lys MAR: Start: 1 End: 2960
P(LAC): Start: 3043 End: 3043
P(BLA) (bla gene promoter): Start: 5057 End: 5057
Replication Origin ORI (RNaseH cleavage point): Start: 3403 End: 3403

FIG. 13. Plasmid map of pinAIL10/MAR(−).

The figure describes the map of plasmid, pinAIL10/MAR (−), that has the chicken lysozyme MAR element juxtaposed to the heavy chain expression cassette of the anti-IL10 gene containing the hygromycin resistance marker.

AP(R): Start: 3965 End: 4828
MAR-lys (MAR-lys is Matrix Attachment Region): Start: 5087 End: 8045
VDJ (VDJ region of anti-IL10 (12G8)): Start: 8928 End: 9369
IgG1 (IgG1 non genomic region): Start: 9374 End: 10354
DHFR cDNA: Start: 601 End: 1347
SV40 t Ag Intron: Start: 14897 End: 600
VDJ-IgK (VDJ-IgK for 12G8 light chain (anti-IL10)): Start: 13026 End: 13755
pBR322: Start: 2811 End: 3019
pBR322: Start: 3020 End: 5033
TK-Hygromycin: Start: 10663 End: 12672
Beta Globin PolyA signal: Start: 10379 End: 10617
Beta globin pA signal: Start: 12765 End: 13013
SV40 POLYA: Start: 14650 End: 14898
MMTV-LTR: Start: 1348 End: 2810
hCMV/intron (Human CMV promoter with hybrid intron): Start: 8077 End: 8918
hCMV/intron (Human CMV promoter and hybrid intron): Start: 13771 End: 14612
pBR ORI: Start: 3207 End: 3207

FIG. 14. Plasmid map of pAIL10V1/puro/MAR(−).

The figure describes the map of plasmid, pAIL10/puro/MAR(-), that has chicken lysozyme MAR element juxtaposed to the heavy chain expression cassette of the anti-IL10 gene containing the puromycin instead of the hygromycin resistance marker.
AP: Start: 3965 End: 4828
MAR-lys (MAR-lys is Matrix Attachment Region): Start: 5087 End: 8045
VDJ: Start (VDJ region of anti-IL10 (12G8)): 8928 End: 9369
IgG1 (IgG1 non genomic region): Start: 9374 End: 10354
PURO: Start: 11674 End: 12905
DHFR cDNA: Start: 601 End: 1347
SV40 t Ag Intron: Start: 15070 End: 600
VDJ-IgK (VDJ-IgK for 12G8 light chain (anti-IL10)): Start: 13199 End: 13928
(Complementary)
pBR322: Start: 2811 End: 3019
pBR322: Start: 3020 End: 5033
Beta Globin Poly A signal: Start: 10379 End: 10617
SV40 POLYA: Start: 10784 End: 10789
Beta globin pA signal: Start: 12938 End: 13186
SV40 POLYA: Start: 14823 End: 15071
MMTV-LTR: Start: 1348 End: 2810
hCMV/intron (Human CMV promoter with hybrid intron): Start: 8077 End: 8918
HCMV-MIE: Start: 10902 End: 11660
hCMV/intron (Human CMV promoter and hybrid intron): Start: 13944 End: 14785
(Complementary)
pBR ORI: Start: 3207 End: 3207

FIG. 15. Plasmid map of pAIGFRLCb2/MAR(-).

The figure describes the map of plasmid, that has chicken lysozyme MAR element juxtaposed to the heavy chain expression cassette of the anti-IGFR1 gene containing the hygromycin resistance marker.
AP(R): Start: 3965 End: 4828
MAR-lys (MAR-lys is Matrix Attachment Region): Start: 5087 End: 8045
VDJ (VDJ of IGFR1 of 11D8 hybridoma): Start: 8974 End: 9401
IgG1 (IgG1 non genomic region): Start: 9401 End: 10381
DHFR cDNA: Start: 601 End: 1347
SV40 t Ag Intron: Start: 14924 End: 600
Kappa (Kappa Chain): Start: 13063 End: 13386
VDJ (VDJ of IGFR1 (LCb, human germline sequence)): Start: 13387 End: 13764
pBR322: Start: 2811 End: 3019
pBR322: Start: 3020 End: 5033
TK-Hygromycin: Start: 10690 End: 12699
Beta Globin Poly A signal: Start: 10406 End: 10644
Beta globin pA signal: Start: 12792 End: 13040
SV40 POLYA: Start: 14677 End: 14925
MMTV-LTR: Start: 1348 End: 2810
hCMV/intron (Human CMV promoter with hybrid intron): Start: 8077 End: 8918
hCMV/intron (Human CMV promoter and hybrid intron): Start: 13786 End: 14627
pBR ORI: Start: 3207 End: 3207

FIG. 16. Plasmid map of pAIGFRLCb2V1/puro/MAR(-).

The figure describes the map of plasmid, that has chicken lysozyme MAR element juxtaposed to the heavy chain expression cassette of the anti-IGFR1 gene containing the puromycin instead of the hygromycin resistance marker.
AP(R): Start: 3965 End: 4828
MAR-lys (MAR-lys is Matrix Attachment Region): Start: 5087 End: 8045
VDJ (VDJ of IGFR1 of 11D8 hybridoma): Start: 8974 End: 9401
IgG1 (IgG1 non genomic region): Start: 9401 End: 10381
PURO(R): Start: 11701 End: 12932
DHFR cDNA: Start: 601 End: 1347
SV40 t Ag Intron: Start: 15097 End: 600
Kappa (Kappa Chain): Start: 13236 End: 13559
VDJ (VDJ of IGFR1 (LCb, human germline sequence)): Start: 13560 End: 13937
pBR322: Start: 2811 End: 3019
pBR322: Start: 3020 End: 5033
Beta Globin Poly A signal: Start: 10406 End: 10644
SV40 POLYA: Start: 10811 End: 10816
Beta globin pA signal: Start: 12965 End: 13213
SV40 POLYA: Start: 14850 End: 15098
MMTV-LTR: Start: 1348 End: 2810
hCMV/intron (Human CMV promoter with hybrid intron): Start: 8077 End: 8918
HCMV-MIE: Start: 10929 End: 11687
hCMV/intron (Human CMV promoter and hybrid intron): Start: 13959 End: 14800
pBR ORI: Start: 3207 End: 3207

DETAILED DESCRIPTION

The present invention provides a plasmid system useful for recombinant protein expression in any cell, for example in a mammalian cell, a bacterial cell, a yeast cell or an insect cell. The plasmid system is amenable to any cell based expression of a broad range of recombinant proteins, ranging from simple proteins, such as interferon, to complex proteins, such as antibodies. The system offers many common and rare restriction sites to accommodate a variety of expression cassettes. It also provides flexibility in the choice of various elements of an expression cassette, such as a promoter, enhancer, and terminator, as well as an antibiotic resistance marker. The plasmids can also be used as simple transfer vectors. The system offers potential for both transient as well as stable expression. The pXBLS vector carries the dihydrofolate reductase (DHFR) coding region for selection and amplification of the plasmid in DHFR deficient mammalian cells, e.g. CHO DXB-11 and CHO DG44. Thus, the system can be used for isolating stable clones, harnessing gene amplification and selection. The plasmid system includes two universal transfer plasmids, pUHLS and pULLS, which are useful for carrying out expression of the parts of a complex protein such as an antibody. Thus, the system offers options of co-transfection with universal vectors and single transfection with pXBLS. The ability of the plasmid system to cause such segregated expression of various parts is advantageous since it is sometimes necessary to take a deeper insight into the expression of individual units of a multi-subunit protein in order to analyze the overall expression of the complex protein. The system can also be used to address the effect of directional variability, resulting from the orientation of the multiple genes in the plasmid for the expression of multi-subunit proteins. Thus, a strategy in placing multiple expression cassettes can be arrived at for optimal expression of a complex protein.

The plasmid system of the invention has been demonstrated to direct high levels of expression of multiple polypeptides including anti-IL5 antibody, anti-IGFR1 antibody, IL2 receptor membrane domain, and anti-IL10 antibody. Other proteins may also be expressed in the plasmid system of the invention including interferon, fibrinogen, ion channels, bacterial porins (e.g., ompF), and the nicotinic acetylcholine receptor (nAChR).

In one embodiment of the invention, the plasmid system comprises the light and heavy chain of the fully human, monoclonal anti-IGFR1 antibody 15H12/19D12 which may also be referred to as 15H12 or as 19D12.

The parts to the plasmid system can be provided separately or, conveniently, together as part of a kit.

The present invention includes any of the polynucleotide comprising or consisting of a nucleotide sequence set forth, below, in Table 1, individually or as part of a plasmid system or kit. Polynucleotides of the invention can be in any form, including circular, linear, double-stranded or single-stranded.

TABLE 1

Polynucleotides of the invention.

| Polynucleotide | Sequence Identifier |
| --- | --- |
| pULLS | SEQ ID NO: 1 |
| pUHLS | SEQ ID NO: 2 |
| pXBLS | SEQ ID NO: 3 |
| pULSRstopLS | SEQ ID NO: 4 |
| pUHSRstopLS | SEQ ID NO: 5 |
| pAIL5V1 | SEQ ID NO: 6 |
| pAIGFRV3 | SEQ ID NO: 7 |
| pAIG1FR(-)IL2LS | SEQ ID NO: 8 |
| pAIL 10V3 | SEQ ID NO: 9 |
| pXBLS multiple cloning site | SEQ ID NO: 10 |
| pUHLS multiple cloning site | SEQ ID NO: 11 |
| pULLS multiple cloning site | SEQ ID NO: 12 |
| pSRXBLS | SEQ ID NO: 13 |
| pDSRG | SEQ ID NO: 14 |
| Nucleotide sequence encoding the 15H12 and 19D12 light chain variable region-including signal peptide (15H12/19D12 LC) | SEQ ID NO: 15 |
| Amino acid sequence of the 15H12 and 19D12 light chain variable region-including signal peptide | SEQ ID NO: 16 |
| Nucleotide sequence encoding the 15H12 and 19D12 heavy chain variable region including signal peptide (15H12/19D12 HC) | SEQ ID NO: 17 |
| Amino acid sequence of the 15H12 and 19D12 heavy chain variable region including signal peptide | SEQ ID NO: 18 |
| Nucleotide sequence encoding the 15H12/19D12 light chain F (LCF) | SEQ ID NO: 19 |
| Amino acid sequence of the 15H12/19D12 light chain F | SEQ ID NO: 20 |
| Nucleotide sequence encoding the 15H12/19D12 heavy chain A (HCA) | SEQ ID NO: 21 |
| Amino acid sequence of the 15H12/19D12 heavy chain A | SEQ ID NO: 22 |
| Nucleotide sequence of the chicken lysozyme MAR element | SEQ ID NO: 23 |
| pinAIL 10/MAR(-) | SEQ ID NO: 24 |
| pAIL 10V1/puro/MAR(-) | SEQ ID NO: 25 |
| pAIGFRLCb2/MAR(-) | SEQ ID NO: 26 |
| PAIGFRLCb2/puro/MAR(-) | SEQ ID NO: 27 |

Molecular Biology

In accordance with the present invention there may be employed conventional molecular biology, microbiology, and recombinant DNA techniques within the skill of the art. Such techniques are explained in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" includes the polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA or peptide, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

As used herein, the term "oligonucleotide" refers to a nucleic acid, generally of no more than about 300 nucleotides (e.g., 30, 40, 50, 60, 70, 80, 90, 150, 175, 200, 250, 300), that may be hybridizable to a genomic DNA molecule, a cDNA molecule, or an mRNA molecule encoding a gene, mRNA, cDNA, or other nucleic acid of interest. Oligonucleotides are usually single-stranded, but may be double-stranded. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

A "protein sequence", "peptide sequence" or "polypeptide sequence" or "amino acid sequence" refers to a series of two or more amino acids in a protein, peptide or polypeptide.

"Protein", "peptide" or "polypeptide" includes a contiguous string of two or more amino acids.

The term "isolated polynucleotide" or "isolated polypeptide" includes a polynucleotide (e.g., RNA or DNA molecule, or a mixed polymer) or a polypeptide, respectively, which is partially or fully separated from other components that are normally found in cells or in recombinant DNA expression systems or any other contaminant. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

"PCR amplification" of DNA as used herein includes the use of polymerase chain reaction (PCR) to increase the concentration of a particular DNA sequence within a mixture of DNA sequences. For a description of PCR see Saiki, et al., Science (1988) 239:487. Genes can be amplified, for example, in a cell. Cells harboring a plasmid containing an amplifiable, selectable marker, but lacking an endogenous marker gene, such as DHFR, can be selected with increasing amounts of a selecting agent, such as methotrexate (e.g., if the DHFR gene is on the plasmid). Typically, this procedure will cause the copy number of the plasmid containing the amplifiable, selectable marker in the cell to increase.

The term "host cell" includes any cell of any organism that is selected, modified, transfected, transformed, grown, or used or manipulated in any way, for the production of a substance by the cell, for example the expression or replication, by the cell, of a gene, a DNA or RNA or a protein. For example, a host cell may be a bacteria such as *E. coli* or an eukaryotic cell such as a CHO cell.

A "cassette" or an "expression cassette" refers to a DNA coding sequence or segment of DNA that codes for an expression product (e.g., peptide or RNA) that can be inserted into a vector at defined restriction sites. The DNA coding sequence can be operably linked to a promoter and/or to a terminator and/or polyA signal.

The sequence of a nucleic acid may be determined by any method known in the art (e.g., chemical sequencing or enzymatic sequencing). "Chemical sequencing" of DNA includes methods such as that of Maxam and Gilbert (Proc. Natl. Acad. Sci. USA (1977) 74:560), in which DNA is randomly cleaved using individual base-specific reactions. "Enzymatic sequencing" of DNA includes methods such as that of Sanger (Sanger, et al., Proc. Natl. Acad. Sci. USA (1977) 74:5463).

The present invention includes nucleic acids of the invention flanked by natural regulatory (expression control) sequences, which may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

"Internal ribosome entry sites" "IRES" are commonly known in the art. Internal ribosome entry sites have been identified in a several genes including eIF4G (Johannes et al., RNA 4: 1500-1513 (1998)), DAP5 (Henis-Korenblit et al., Molecular and Cellular Biology 20: 496-506 (2000)), c-Myc (Stoneley et al., Molecular and Cellular Biology 20: 1162-1169 (2000)), NF-κ-b repressing factor (Oumard et al., Molecular and Cellular Biology 20: 2755-2759 (2000)), VEGF (Huez et al., Molecular and Cellular Biology 18: 6178-6190 (1998)), FGF-2 (Creancier et al., Journal of Cell Biology 150: 275-281 (2000)), PDGF-B (Bernstein et al., Journal of Biological Chemistry 272: 9356-9362 (1997)), X-linked inhibitor of apoptosis (XIAP) (Holcik et al., Oncogene 19: 4174-4177 (2000)), Apaf-1 (Coldwell et al., Oncogene 19: 899-905 (2000)) and BiP (Macejak et al., Nature 353: 90-94 (1991)).

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention.

A coding sequence is "under the control of", "functionally associated with", "operably linked to" or "operably associated with" transcriptional and translational control sequences in a cell when the sequences direct or regulate expression of the sequence. For example, a promoter operably linked to a gene will direct RNA polymerase mediated transcription of the coding sequence into RNA, preferably mRNA, which then may be RNA spliced (if it contains introns) and, optionally, translated into a protein encoded by the coding sequence. A terminator/polyA signal operably linked to a gene terminates transcription of the gene into RNA and directs addition of a poly A signal onto the RNA.

The terms "express" and "expression" mean allowing or causing the information in a gene, RNA or DNA sequence to become manifest; for example, producing a protein by activating the cellular functions involved in transcription and translation of a corresponding gene. "Express" and "expression" include transcription of DNA to RNA and RNA to protein. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species. Examples of transformation methods which are very well known in the art include liposome delivery, electroporation, $CaPO_4$ transformation, DEAE-Dextran transformation, microinjection and viral infection.

The present invention includes vectors which comprise polynucleotides of the invention. The term "vector" may refer to a vehicle (e.g., a plasmid) by which a DNA or RNA sequence can be introduced into a host cell, so as to transform the host and, optionally, promote expression and/or replication of the introduced sequence.

The polynucleotides of the invention may be expressed in an expression system. The term "expression system" means a host cell and compatible vector which, under suitable conditions, can express a protein or nucleic acid which is carried by the vector and introduced to the host cell. Common expression systems include *E. coli* host cells and plasmid vectors, insect host cells and baculovirus vectors, and mammalian host cells and vectors such as plasmids, cosmids, BACs, YACs and viruses such as adenovirus and adenovirus associated virus (AAV).

Plasmids

In one embodiment, the present invention comprises a kit comprising a first universal transfer vector comprising a multiple cloning site, a replication origin, and a selectable marker; a second universal transfer vector comprising a multiple cloning site, a replication origin, and a selectable marker and an amplifiable vector comprising a multiple cloning site, a promoter, a replication origin or a chromosomal integration site, a poly-adenylation site and an amplifiable selectable marker. Generally, the multiple cloning sites comprise about 20, 25 or 30 restriction sites.

Plasmids of the present invention may include any of several amplifiable markers known in the art. Use of amplifiable markers is discussed in Maniatis, *Molecular Biology: A Laboratory Manual*, Cold Spring Harbor Laboratory, NY (1989)). Useful selectable markers for gene amplification in drug-resistant mammalian cells include DHFR (MTX (methotrexate) resistance) (Alt et al., J. Biol. Chem. 253:1357 (1978); Wigler et al., Proc. Natl. Acad. Sci. USA 77:3567 (1980)); metallothionein (cadmium resistance) (Beach et al., Proc Natl. Acad. Sci. USA 78:210 (1981)); CAD (N-(phosphonoacetyl)-1-aspartate (PALA) resistance) (Wahl et al., J. Biol. Chem. 254: 8679 (1979)); adenylate deaminase (coformycin resistance) (Debatisse et al., Mol. Cell. Biol. 6:1776 (1986)); IMP 5'-dehydrogenase (mycophenolic acid resistance) (Huberman et al., Proc. Natl. Acad. Sci. USA 78:3151 (1981)) and other markers known in the art (as reviewed, for example, in Kaufman et al., Meth. Enzymology 185:537-566 (1988)).

In one embodiment, the metallothionein II A gene under the control of a metallothionein promoter is an amplifiable marker in cell lines such as CHO-K1. Amplification can be induced by addition of $Cd^{2+}$ or $Zn^{2+}$ to the cell culture.

Plasmids of the invention may include other eukaryotic, non-amplifiable selectable markers known in the art. In an embodiment of the invention, the drug-resistance marker is the hygromycin B gene which confers resistance to hygromycin. Other markers include the G418 resistance gene. The plasmids of the invention may also include a prokaryotic antibiotic resistance marker such as the ampicillin resistance gene or the kanamycin resistance gene.

Plasmids of the invention may also include a matrix attachment region (MAR). Generally, MARs are DNA sequences capable of specific binding to nuclear proteins that are part of a fibrillar nuclear matrix analogous to the cytoskeleton. In one embodiment, the MAR is the chicken lysozyme MAR.

Promoters which may be used to control gene expression include, but are not limited to, SRα promoter (Takebe et al., Molec. and Cell. Bio. 8:466-472 (1988)), the human CMV immediate early promoter (Boshart et al., Cell 41:521-530 (1985); Foecking et al., Gene 45:101-105 (1986)), the mouse CMV immediate early promoter, the SV40 early promoter region (Benoist, et al., Nature 290:304-310 (1981)), the *Orgyia pseudotsugata* immediate early promoter, the herpes thymidine kinase promoter (Wagner, et al., Proc. Natl. Acad. Sci. USA 78:1441-1445 (1981)), the regulatory sequences of the metallothionein gene (Brinster, et al., Nature 296:39-42 (1982)); prokaryotic expression vectors such as the β-lactamase promoter (Villa-Komaroff, et al., Proc. Natl. Acad. Sci. USA 75:3727-3731 (1978)), or the tac promoter (DeBoer, et al., Proc. Natl. Acad. Sci. USA 80:21-25 (1983)); and promoter elements from yeast or other fungi such as the GAL1, GAL4 or GAL10 promoter, the ADH (alcohol dehydrogenase) promoter, PGK (phosphoglycerol kinase) promoter or the alkaline phosphatase promoter.

Viral long terminal repeat promoters such as the mouse mammary tumor virus long terminal repeat (MMTV-LTR) (Fasel et al., EMBO J. 1(1):3-7 (1982)), the moloney murine sarcoma virus long terminal repeat (Reddy et al., Proc. Natl. Acad. Sci. USA 77(9): 5234-5238 (1980)), the moloney murine leukemia virus long terminal repeat (Van Beveren et al., Proc. Natl. Acad. Sci. USA 77(6): 3307-3311 (1980)), the HIV LTR (Genbank Accession No. AB100245), the bovine foamy virus LTR (Genbank Accession No. NC_001831), RSV 5'-LTR (Genbank Accession No. K00087), the HIV-2 LTR (Genbank Accession No. NC_001722), an avian retroviral LTR (Ju et al., Cell 22: 379-386 (1980)) and the human herpesvirus LTR (Genbank Accession No. NC_001806) may be included in the plasmids of the present invention.

Other acceptable promoters include the human CMV promoter, the human CMV5 promoter, the murine CMV promoter, the EF1α promoter, the SV40 promoter, a hybrid CMV promoter for liver specific expression (e.g., made by conjugating CMV immediate early promoter with the transcriptional promoter elements of either human α1-antitrypsin (HAT) or albumin (HAL) promoter), or promoters for hepatoma specific expression (e.g., wherein the transcriptional promoter elements of either human albumin (HAL; about 1000 bp) or human α1-antitrypsin (HAT, about 2000 bp) are combined with a 145 bp long enhancer element of human α1-microglobulin and bikunin precursor gene (AMBP); HAL-AMBP and HAT-AMBP).

In addition, bacterial promoters, such as the T7 RNA Polymerase promoter or the tac promoter, may be used to control expression.

A promoter (e.g., SRα promoter) may be linked to the cassette and then moved into a transfer vector (e.g., pULLS or pUHLS). In another embodiment, the transfer vector can contain a promoter upstream of the multiple cloning site (e.g., pULSRstopLS or pUHSRstopLS). When a gene, not linked to a promoter, is inserted into the multiple cloning site, it will be operably linked to the upstream promoter.

In yet another embodiment of the invention, a gene in a transfer vector, not linked to a promoter, can be moved into the amplifiable vector comprising a promoter (e.g., SRα promoter) upstream of the multiple cloning site (e.g., pSRX-BLS). When the unlinked gene is placed in the multiple cloning site, it will become operably linked to the promoter.

Plasmids of the invention may also include a polyadenylation signal/terminator for termination of the transcription of a gene in the plasmid and for the addition of a polyA tail to the transcript. For example, the chicken β-globin terminator/polyA signal may be included in a plasmid of the invention. Other acceptable poly A signals include the SV40 Poly A signal and the bovine growth hormone poly A signal.

In one embodiment of the invention, the amplifiable vector comprises a multiple cloning site including the following restriction sites: Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv C1, Pme I, Bss HII, Asc I, Xba I; for example, wherein the amplifiable vector multiple cloning site is that of pXBLS:

```
                                                    (SEQ ID NO: 10)
                 AscI                    BclI        BsrGI
                 ~~~~~~~~                ~~~~~       ~~~~~
                         PmeI
                         ~~~~~~~~~
     XbaI    BssHII              BbvC1        BspEI
     ~~~~~   ~~~~~                ~~~~~~~      ~~~~~~~
   1 AAATCTAGAG GCGCGCCGTT TAAACCCTCA GCTGATCATC CGGATGTACA
     TTTAGATCTC CGCGCGGCAA ATTTGGGAGT CGACTAGTAG GCCTACATGT
```

```
             FseI           MluI           NdeI           NruI
     BssHII        KpnI           MscI           NotI
 51  GCGCGCGGCC GGCCGGTACC ACGCGTTGGC CACATATGCG GGCCGCTCGC
     CGCGCGCCGG CCGGCCATGG TGCGCAACCG GTGTATACCG CCGGCGAGCG
         PacI           SacII         Srf1             XhoI
     NruI          RsrII          SpeI   XmaI    SgrAI
101  GATTAATTAA CGGACCGCCG CGGACTAGTG CCCGGGCCAC CGGTGCTCGA
     CTAATTAATT GCCTGGCGGC GCCTGATCAC GGGCCCGGTG GCCACGAGCT
     XhoI
151  GAAAA
     CTTTT.
```

In an embodiment of the invention, a universal transfer vector comprises a multiple cloning site including the following restriction sites: Bss HII, Pme I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam HII, Dsa I, Eag I, Ecl XI, Not I, Sac II, Xma III, Xba I, Sac I, Mlu I, Bcl I, Bsr GI, Bss HII; for example, wherein the transfer vector multiple cloning site is that of pUHLS:

AI, Xma I, Rsr II, Spe I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Bsp EI, Bam H1, Dsa I, Eag I, Ecl XI, Not I, Sac II, Xma III, Xba I, Sac I, Nde I, Msc I, Nru I, Pac I, Bss HII; for example, wherein the transfer vector multiple cloning site is that of pULLS:

```
                                                    (SEQ ID NO: 11)
         AscI                          HindIII    PaeR7I
                   PmeI      SnaBI         KpnI
     XmaI                                              XhoI
         BssHII         BbvC1           Asp718
  1  GGGGGCGCGC CGTTTAAACC CTCAGCTACG TAAAGCTTGG TACCCTCGAG
     CCCCCGCGCG GCAAATTTGG GAGTCGATGC ATTTCGAACC ATGGGAGCTC
         ClaI                                        BspEI
     HincII       EcoRV         PstI
       SalI                                XmaI
     AccI           EcoRV        ApaI            BamHI
 51  GTCGACATCG ATGATATCGA ATTCCTGCAG GGGCCCCCCG GGTCCGGAGG
     CAGCTGTAGC TACTATAGCT TAAGGACGTC CCCGGGGGGC CCAGGCCTCC
         NotI           MluI         BsrGI
                SacI
     BamHI     XbaI             BclI            FseI
101  ATCCGCGGCC GCTCTAGAGA GCTCACGCGT TGATCATGTA CAGGCCGGCC
     TAGGCGCCGG CGAGATCTCT CGAGTGCGCA ACTAGTACAT GTCCGGCCGG
            XmaI
       BssHII
151  AGCGCGCCCC
     TCGCGCGGGG.
```

A universal transfer vector may comprise a multiple cloning site including the following restriction sites: Bss HII, Sgr

```
                                                    (SEQ ID NO: 12)
                         SgrAI               SnaBI
          XmaI              Srf1      SpeI
             BssHII       XmaI   RsrII         HindIII
  1  GGGGGCGCGC CACCGGTGGC CCGGGCCGGT CCGACTAGTT ACGTAAAGCT
     CCCCCGCGCG GTGGCCACCG GGCCCGGCCA GGCTGATCAA TGCATTTCGA
```

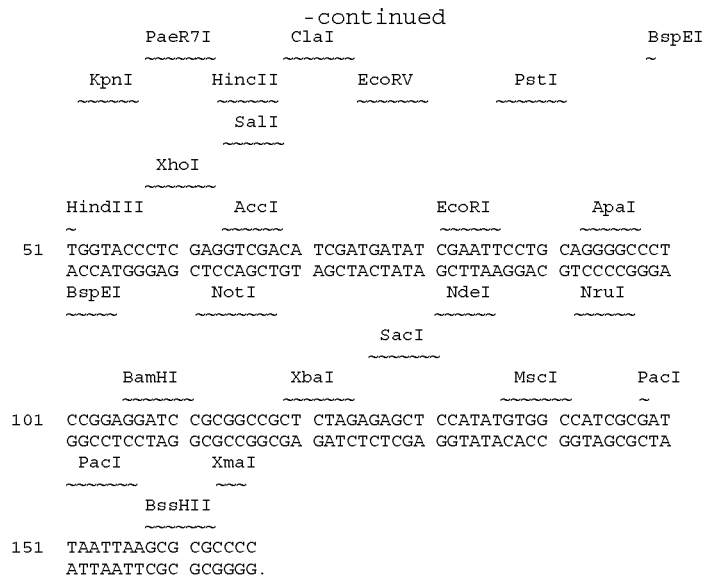

The present invention contemplates amplifiable vectors or universal transfer vectors comprising the above-referenced multiple cloning sites in the orientation shown or in the opposite orientation.

The plasmids of the present invention can be introduced into any cell line for expression of the target polypeptides. In one embodiment of the invention, the plasmids are introduced into a mammalian cell line, preferably a Chinese hamster ovary (CHO) cell line. A commonly used cell line is DHFR-CHO cell line which can be transformed to the DHFR$^+$ phenotype using DHFR cDNA as an amplifiable dominant marker. One such known DHFR-CHO cell line is DX-B11 or DG-44. In another embodiment, the plasmids of the invention can be introduced into a lower eukaryotic cell line, such as from *S. cerevisiae, K. lactis, P. pastoris, C. albicans* or *A. fumigatus*. Further, the plasmids of the invention may also be introduced into higher eukaryotic non-mammalian cell lines such as from insect cells (e.g., *Drosophila melanogaster*, sf9 cells, sf21 cells), amphibian cells (e.g., *X. laevis*), plant cells (e.g., *A. thaliana*) and avian cells.

Plasmids of the invention can also be introduced into a bacterial cell. In one embodiment, competent *E. coli* are transformed. Examples of suitable *E. coli* include DH1, DH5, DH5α, XL1-Blue, SURE, SCS110, OneShot Top 10, and HB101.

Plasmids may be introduced into a cell by any of the many methods which are commonly known in the art. For example, a plasmid of the invention can be used to transform a cell by the calcium phosphate method, electroporation, the DEAE-dextran method or the liposome method.

The plasmids of the invention can include any gene or combination of genes. In an embodiment of the invention the plasmids include heavy and light chain immunoglobulin genes. The immunoglobulin chains may be part of antibodies which specifically recognize any antigen such as IL-5, IGFR1 or IL-10. Receptors or receptor subunits may also be expressed. For example, a gene encoding the IL-2 receptor or a portion thereof (e.g., membrane domain) can be included in a plasmid of the invention.

U.S. patent application Ser. No. 10/443,466; filed May 22, 2003, which is herein incorporated by reference in its entirety, sets forth the nucleotide and amino acid sequences of immunoglobulin light chain and heavy chain variable regions of anti-IGFR1 antibodies. Any of the light and heavy chain variable regions disclosed therein can be incorporated into the plasmid system of the invention and expressed. In one embodiment, the anti-IGFR1 antibody light chain variable region is encoded by the nucleotide sequence set forth in SEQ ID NO: 15 or 19 or is any polynucleotide encoding a polypeptide comprising the amino acid sequence of SEQ ID NO: 16 or 20 and/or the anti-IGFR1 antibody heavy chain variable region is encoded by the nucleotide sequence set forth in SEQ ID NO: 17 or 21 or is any polynucleotide encoding a polypeptide comprising the amino acid sequence of SEQ ID NO: 18 or 22.

Expression cassettes encoding the immunoglobulin heavy and light chain of the anti-IGFR1 antibody can each be introduced into the multiple cloning site of either pULLS or pUHLS. Preferably, the immunoglobulin heavy and light chains, in the expression cassettes, are linked to an immunoglobulin constant region such as γ1, γ4 or κ. Preferably, the expression cassettes are then inserted into the amplifiable vector pXBLS which is then introduced into a cell suitable for causing the expression of the light and heavy chains. For example, the plasmid, pAIGFRV3, which contains the immunoglobulin heavy and light chains of an anti-IGFR1 antibody, can be introduced into a dhfr mammalian cell line (e.g., CHO-DXB11) wherein the chains are expressed.

Kits

The plasmid system of the invention may be provided in a kit. The kits of the invention may include, in addition to the plasmid system, any reagent which may be employed in the use of the plasmid system. In one embodiment, the kit includes reagents necessary for transformation of the plasmids into mammalian cells. For example, the kit may include reagents for a calcium phosphate transformation procedure: calcium chloride, buffer (e.g., 2×HEPES buffered saline), and sterile, distilled water. In another embodiment, the kit includes reagents for a DEAE-Dextran transformation: Chloroquine in PBS, DEAE-dextran in PBS and Phosphate buffered saline. In yet another embodiment, reagents for a liposome transformation are included in the kit: Liposomes extruded from DOTAP/cholesterol extruded liposomes. For example, the kit may include the cationic lipid-based transfection reagent Lipofectamine™ (Invitrogen Life Technologies; Carlsbad, Calif.).

The kit may include reagents required for bacterial transformation of the plasmids of the invention. For example, the kit may include transformation competent bacteria (e.g., DH1, DH5, DH5α, XL1-Blue, SURE, SCS110, OneShot Top 10, or HB101).

The kit may include growth media or reagents required for making growth media. For example, in one embodiment, the kit can include fetal calf serum or DMEM (Dulbecco/Vogt modified Eagle's (Harry Eagle) minimal essential medium) for growth of mammalian cells. In another embodiment, the kit can contain powdered luria broth media or luria broth plates containing an appropriate antibiotic (e.g., ampicillin or kanamycin) for growing bacteria.

Components supplied in the kit may be provided in appropriate vials or containers (e.g., plastic or glass vials). The kit can include appropriate label directions for storage, and appropriate instructions for usage.

Protein Expression and Purification

Polypeptides produced in the plasmid system of the invention can be purified by standard methods, including, but not limited to, salt or alcohol precipitation, affinity chromatography (e.g., used in conjunction with a purification tag), preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in "*Guide to Protein Purification*", *Methods in Enzymology*, Vol. 182, M. Deutscher, Ed., 1990, Academic Press, New York, N.Y.

Particularly where a polypeptide is being isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

Polypeptides of the invention may be fused with a second polypeptide or polynucleotide moiety, which may be referred to as a "tag". A tag may be used, for example, to facilitate purification or detection of the polypeptide after expression. A fused polypeptide may be constructed, for example, by in-frame insertion of a polynucleotide encoding the tag on the 5' or 3' end of the polynucleotide encoding the polypeptide to be expressed. The fused polynucleotide may then be expressed in the plasmid system of the invention. Such tags include glutathione-S-transferase (GST), hexahistidine (His6) tags, maltose binding protein (MBP) tags, haemagglutinin (HA) tags, cellulose binding protein (CBP) tags and myc tags. Detectable tags such as $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides and polynucleotides of the invention. Methods for constructing and using such fusions are very conventional and well known in the art.

EXAMPLES

The following examples are provided to further describe the present invention and should not be construed as a limitation thereof. The scope of the present invention includes any and all plasmids set forth, below, in the following examples either individually or as part of a kit. Also included within the scope of the invention are any and all of the methods which are set forth below in the following examples.

Example 1

Construction of Amplifiable Cloning Vectors, pSRXBLS and pXBLS

This example describes the construction of the mammalian expression vectors, pSRXBLS and pXBLS. A large multi-cloning site was inserted in the plasmid pDSRG downstream of the SRα promoter, to generate pSRXBLS. pXBLS, a derivative of pSRXBLS, is devoid of any promoter. Both of the plasmids can serve as amplifiable vectors into which more than one expression cassette, e.g., for the heavy and light chain cDNAs of an antibody gene, can be easily inserted.

A multiple cloning site of 155 bp, pDSRG-xba-xho, was designed, synthesized by PCR and cloned initially in the TA Cloning Vector (Invitrogen; Carlsbad, Calif.). It was later cloned at the XhoI and XbaI sites of pDSRG, resulting in pSRXBLS. The SRα promoter was retained in the pSRXBLS vector.

pSRXBLS was further digested with XhoI and HindIII to remove the SRα promoter. The ends were then filled in by Klenow and religated, regenerating the HindIII site, to construct pXBLS.

Example 2

Construction of Universal Transfer Vectors pUHLS, pULLS and their Descendents

This example describes the construction of universal transfer vectors, each having a large multiple cloning site, and their descendents, each carrying a promoter and a terminator/poly A addition site. pUHLS and pULLS are the universal transfer vectors, and pUHSRstopLS and pULSRstopLS are their corresponding descendents that carry the SRα promoter and the chicken β-globin terminator. The plasmid system is so constructed that different subunits of a large, complex protein can be expressed in these vectors separately. Later, the expression cassettes for each subunit can be transferred to a single vector, such as pXBLS or pSRXBLS, to facilitate transfection, integration and equimolar production of a multi-subunit protein.

Two multiple cloning sites, Universal Plasmid Primer 1 of 160 bp and Universal Plasmid Primer 2 of 166 bp, were designed to construct pUHLS and pULLS. Both of the cloning sites were synthesized by PCR, cloned in the TA Cloning Vector (Invitrogen) and later cloned at the BssHII sites of the pCRScript vector (Stratagene). Thus, the original multiple cloning site of pCRScript was replaced with newly synthesized multiple cloning sites. The new vectors, pUHLS and pULLS, were derived from the Universal Plasmid Primer 1 and Universal Plasmid Primer 2, respectively.

A 249 bp region of the chicken β-globin terminator, derived from pDSRG by digestion with BamHI and XbaI, was inserted in both pUHLS and pULLS at the BamHI and XbaI sites to generate pUHstopLS and pULstopLS, respectively. The SRα promoter and its accompanying intron, derived from pDSRG by digestion with HindIII and SalI, was inserted in pUHstopLS and pULstopLS at the HindIII and XhoI sites to generate pUHSRstopLS and pULSRstopLS, respectively.

Example 3

Construction of pAIL5V1

The construction of pAIL5V1 for the expression of heavy and light antibody chains in a single vector is described here.

Aside from variations in their orientations, two types of plasmids have been constructed. The first carries only the dhfr marker for selection with amplification. The second type of expression plasmid carries the dhfr marker, along with the gene for hygromycin resistance (Hyg). This adds versatility, allowing selection with or without amplification.

The heavy chain gene of the anti-huIL5 human monoclonal antibody, (MAb) was isolated and inserted in the pUHSR-stopLS vector (supra) at the EcoRI and XmaI sites to generate pUSRHLS. The light chain gene of the anti-huIL5 MAb was isolated and inserted in pULSRstopLS at the EcoRI and ApaI sites to generate pUSRLLS.

The hCMV minimal promoter, derived from pcDNA3.1 (Invitrogen; Carlsbad, Calif.) by digestion with NruI and EcoRI, replaced the SRα promoter, which was removed by digestion with SnaBI and EcoRI, in pUSRHLS and pUSRLLS to generate pUhCMVHLS and pUhCMVLLS. The TK-hygromycin gene (TK/Hyg) was inserted in pUhCMVHLS at the FseI sites to construct pUHhyg(+)hCMVLS and pUHhyg(−)hCMVLS. The light chain antibody cassette was transferred from pUhCMVLLS, by digestion with PacI and SrfI, to pXBLS at the PacI and SrfI sites to construct pAIL5L(−)hCMVLS and pAIL5L(+)hCMVLS. The heavy chain antibody cassette was transferred from pUHhyg(−)hCMVLS to pAIL5L(−)hCMVLS at the BssHII sites to generate pAIL5V1.

Example 4

Construction of pAIGFRV3 cDNAs encoding the variable regions from a hybridoma expressing an anti-IGFR1 monoclonal antibody 19D12/15H12 were isolated and cloned in TA cloning vectors (Invitrogen; Carlsbad, Calif.). The light and heavy chain amino acid and nucleotide sequences of antibody 19D12/15H12 are set forth in U.S. patent application Ser. No. 10/443,466; filed May 22, 2003 which is herein incorporated by reference in its entirety. The heavy chain was transferred from the EcoRI and ApaI sites of the TA vector containing cDNA for heavy chain of variable region of anti-IGFR1 to the same sites of pUhCMVHLS (supra) to construct pUhCMVIGFRHLS containing cDNA for light chain of anti-IGFR1. For selection, a TK-hygromycin resistance cassette was inserted at the FseI site of pUhCMVIGFRHLS to construct pUhCMVHyg(−)IG-FRHLS. The light chain was transferred from the EcoRI and BbsI sites of the TA plasmid to the same sites of pUhCMVLLS (supra) to construct pUhCMVIGFRLLS. The entire light chain expression cassette was then transferred from pUhCMVIGFRLLS to pXBLS at the PacI and SrfI sites to construct pAIGFRLLS. The heavy chain expression cassette, along with the hygromycin expression cassette, was transferred to pAIGFRLLS at the BssHII sites to construct pAIGFRV1 and pAIGFRV3 (pIAGFRV1 is essentially identical to pAIGFRV3 except that the orientation of the heavy chain and the TK-Hyg genes are opposite).

Example 5

Construction of pAIL10V3 cDNAs encoding the variable regions of 12G8, a rat antibody which recognizes IL-10 were isolated. The heavy chain variable region of 12G8 was transferred to KpnI and ApaI site of pUhyg(−)IG1FRhuH plasmid to construct pUIL10H. The pUhyg(−)IG1FrhuH plasmid carries the modified cDNA for variable region of IGFR1 along with IgG1 cDNA and TK-Hygromycin cassette. The light chain variable region of 12G8 was transferred to the EcoRI and ApaI sites of pAIL5(−)hCMVLS to construct pAIL10(−)L. The heavy chain expression cassette from the pUIL10H was transferred to pAIL10 (−)L at BssHII restriction sites to construct pAIL10V3.

Example 6

Construction of pAIG1FR(−)IL2LS pAIG1FR(−)IL2LS was constructed in a three step process. The construction process started with transfer of an IRES-IL2Rα element to pULstopLS. The plasmid containing the IRES-IL2Rα, pme18IRES, was digested with SpeI and NotI restriction enzymes and the NotI site was completely filled in using Klenow enzyme to derive the IRES-IL2Rα element. Simultaneously, pULstopLS was digested with EcoRV and SpeI enzymes and the SpeI site was filled in, using the Klenow enzyme, and ligated with the IRES-IL2Rα element to construct pULstopIRESIL2R. pULstopIRESIL2R was further digested with SpeI and XbaI enzyme and SpeI site was completely filled in with Klenow enzyme. Also pUhC-MVIGFRLLS was digested with XbaI and BspEI enzymes and the BspEI site was completely filled in using Klenow enzyme and ligated with the XbaI-SpeI fragment that was generated from pULstopIRESIL2R to construct pUIGFRL-IRESIL2R. The heavy chain expression cassette of IGFR1 was transferred from pUhyg(−)IG1FRhuH to pUIGFRL-IRESIL2R at BssHII restriction sites to construct pAIG1FR (−)IL2LS.

Example 7

Development of Cell Lines for Expressing Anti-IGFR1 Monoclonal Antibody 19D12

In this example, the development and growth of cell lines for expressing the 19D12 antibody (LCF/HCA) are presented.

DXB11 Cell Culture. Cells were grown in MEM Alpha Medium with ribonucleosides and deoxyribonucleosides (GIBCO Cat. #12571-063; Gibco-Invitrogen Corp; Carlsbad, Calif.) plus 10% FBS (HyClone Cat. # SH30071.03; Hyclone; Logan, Utah).

Hygromycin selection media. Cells were split at 48 hours post-transfection. Cells were grown in MEM Alpha Medium without ribonucleosides and deoxyribonucleosides (GIBCO Cat. #12561-056) plus 10% Dialyzed FBS (HyClone Cat. # SH30079.03) plus Hygromycin B (CLONTECH Cat. #8057-1; BD Biosciences-Clontech; Palo Alto, Calif.) at 300 µg/mL.

Subcloning media. Subcloning was performed in MEM Alpha Medium without ribonucleosides and deoxyribonucleosides (GIBCO Cat. #12561-056) plus 10% Dialyzed FBS (HyClone Cat. # SH30079.03).

Methotrexate (MTX) amplification media. Methotrexate amplification was carried out in MEM Alpha Medium without ribonucleosides and deoxyribonucleosides (GIBCO Cat. #12561-056) plus 10% Dialyzed FBS (HyClone Cat. # SH30079.03) plus MTX (Sigma Cat. # M8407; Sigma-Aldrich Corp; St. Louis, Mo.) at 20, 80 and 320 nM, respectively.

Media for adaptation to serum free suspension. Adaptation to serum free suspension was performed in CHO Protein-Free Medium (Sigma Cat. # C5467) supplemented with 20 ml/L L-Glutamine-200 mM (GIBCO Cat. #25030-081) and 10 ml/L Lipids (Cholesterol rich) (Sigma Cat. # L4646).

Feed medium for 3L production batch. L-Glutamine-200 mM (GIBCO Cat. #25030-081) and Glucose Solution (Sigma Cat. # G8769) were served as the feed during production runs.

Transfection and Subcloning method. DXB11 cells were trypsinized, counted and plated @ $2\times10^6$ cells/T25 flask on the day before transfection, so that they became 50-90% confluent on the day of transfection. Transfections were performed using 2.5 µg DNA (pAIGFRV3)/T25 flask and LipofectAMINE PLUS™ reagent (GIBCO, cat. #10964-013). As per the vendor's instructions, the DNA was first complexed with PLUS reagent, the DNA-PLUS complex was mixed with LipofectAMINE reagent and the DNA-PLUS-LipofectAMINE complex was then used to transfect the cells. The cells were incubated at 37° C. at 5% $CO_2$ for 3 hours. Following incubation, DXB11 cell culture medium was added to the desired volume, the cells and medium were transferred to a T75 flask, and the cells were grown for 2 days. The medium was exchanged with hygromycin selection medium, and the cells were grown for 10 days to 2 weeks. Some cells were banked at this stage, and the remaining cells were subcloned in 96 well plates.

Subcloning was initiated in 96 well plates with subcloning media. Single clones were successively grown in 24 well plates, 6 well plates, T-25 flasks and T-75 flasks, following detection of satisfactory expression by ELISA at each stage. Methotrexate media was added on 20-30% confluent cultures for amplification. Amplification was carried out at 20, 40, 80, and 320 nM methotrexate for 10 days to 2 weeks. Following amplification, the media was exchanged with the subcloning media and the cells were allowed to grow to ~10% confluence. The cells were subjected to another round of subcloning at this stage. Following the second round of subcloning, the cells were subjected to adaptation to serum free suspension culture with the designated media at the T-25 flask stage. Serum was sequentially eliminated from the media by dilution with serum free adaptation medium, and the cells were finally transferred to shake flasks with 2.5% serum. The remaining serum was eliminated by subsequent dilution (splitting) of the cultures. The serum free culture was scaled to 3 liters.

Example 8

Propagation of Cells Expressing Anti-IL5 Antibody

Cells carrying pAIL5V1 from a frozen vial are thawed and propagated in suspension using Sigma CHO protein-free medium (C-5467 supplemented with 0.57 g/L L-glutamine). All cultures are maintained in a 37° C., 7.5% $CO_2$ incubator or on a rocker bag platform set at 37° C. and supplying 7.5% $CO_2$. The inoculum train begins in a shake flask and is continuously passaged and scaled-up until there is enough culture to start a 20-Liter bag with a 2-liter working volume. When the bag reaches the predetermined split criteria, it is scaled up to a 10-liter working volume. When the bag reaches the predetermined split criteria, it is split and the remaining culture will be used to start another 20-liter rocker bag (10-liter working volume) in parallel. When the two rocker bags reach the appropriate split density, they are used to seed the production bioreactor. Shake flasks and rocker bags are typically split at 1:4 dilutions when the viable cell density reaches $1$-$1.5\times10^6$ viable cells/mL. The inoculum pool is diluted 1:4 going into the bioreactor.

Flow diagram illustrating the propagation process:

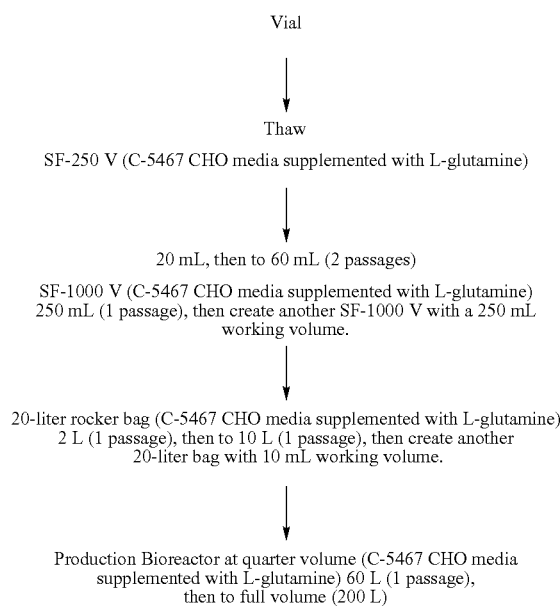

Example 9

Process for Purifying Anti-IL10 Antibody

This example describes the process for purifying the anti-IL10 antibody encoded by pAIL10V3 from a 200 liter CHO cell fermentation. The steps include:

- Harvesting of cell culture supernatant by filtration with a positively charged CUNO filter in series with a 0.2 um filter.
- Affinity chromatography on Amersham rProtein-A Sepharose™ Fast Flow (4 L) eluted by a pH 3.0 step.
- Viral Inactivation by incubation at pH 3.5 for 1 hour at 20-22° C., followed by pH adjustment to 5.5.
- Cation exchange chromatography on EMD Fractogel® SE HiCap (4L) at pH 5.5 eluted with a 20 BV gradient to 250 mM NaCl.
- Concentration (2×)/Diafiltration (10×) into 20 mM Tris, pH 8.0.
- Anion exchange chromatography on Amersham Q Sepharose™ Fast Flow (4 L) in flow-through mode. The unretained peak is pooled and adjusted to pH 5.5.
- Viral Filtration with Planova filters: one 0.1 $m^2$ Planova 35 in series with 2-4 0.1 $m^2$ Planova 20 filters.
- Final concentration (6-10×) and diafiltration (10×) into 20 mM sodium acetate followed by filtration (0.2 µm).

This process yields material that is >99% pure by RP-HPLC. Overall yield is 70%.

Example 10

Expression of Anti-IGFR1 and Anti-IL-10 Antibody

In this example, expression plasmids including the anti-IGFR and anti-IL-10 antibody chains were constructed wherein the antibody chain genes were situated, in the plasmids, adjacent to a MAR element (Selexis; Geneva, Switzerland; Kim et al., J. Biotechnol. 107(2): 95-105 (2004); Stief et al., Nature 341: 343-345 (1989); Phi-Van et al., Mol. Cell.

Biol. 10: 2302-2307 (1990); Kalos et al., Mol. Cell. Biol. 15: 198-207 (1995)). The MAR element is a ~3 kb DNA element that aids the expression of a recombinant gene which is stably integrated in the host chromosome following incorporation into the cell.

The MAR element was inserted into the mammalian expression plasmids, pAIL10Vi, having anti-IL10 along with hygromycin expression cassette, pAIL10V1/puro, having anti-IL10 along with puromycin instead of hygromycin expression cassette, pAIGFRLCb2V1, having anti-IGFR1 along with hygromycin expression cassette, and pAIGFRLCb2V1/puro, having anti-IGFR1 along with puromycin instead of hygromycin expression cassette. Each plasmid already contained four independent mammalian expression cassettes.

The vector, pPAG01 contained the ~3 kb chicken lysozyme matrix attachment region (MAR) DNA element. One of the universal vectors, pULLS was digested by restriction enzymes, Age1 and BamH1 and was religated, following end filling by Klenow enzyme, to construct vector pULLSmod. The pPAG01 plasmid was digested by BamH1 and Xba1 to transfer the MAR element over to pULLSmod at the same sites to construct the plasmid pULMAR. The MAR element was finally transferred to the plasmids expressing anti-IL10 and anti-IGFR1. pULMAR was digested with BssHII and the fragment containing MAR element was transferred to the Asc1 sites of the plasmids pAIL10Vi, pAIL10V1/puro, pAIGFRLCb2V1 and pAIGFRLCb2V1/puro to construct pinAIL10/MAR(-), pAIL10V1/puro/MAR(-), pAIGFR-LCb2/MAR(-) and pAIGFRLCb2/puro/MAR(-), respectively.

The MAR containing plasmids were introduced into the CHO cell line, DXB11 cells and the antibody chains were expressed. Expression of the antibody chains were confirmed by ELISA as well as HPLC analysis. In the HPLC analysis, the proteins isolated from the CHO cells was fractionated using a reverse-phase column or a protein-A column. Eluted protein was detected spectrophotometrically at $A_{280\ nm}$.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

I claim:

1. A method for producing an antibody comprising culturing an isolated host cell comprising a recombined amplifiable vector under conditions favorable to expression of cassettes in said vector; which vector is the product of a method comprising:
   (a) introducing one or more expression cassettes encoding an immunoglobulin light chain or immunoglobulin heavy chain of said antibody into the multiple cloning site of a first universal transfer vector comprising a first multiple cloning site which comprises nucleotides 620-766 of the nucleotide sequence set forth in SEQ ID NO: 2; wherein said multiple cloning site is in said orientation or in a reverse orientation;
   (b) introducing one or more expression cassettes encoding an immunoglobulin light chain or heavy chain of said antibody, different from the cassettes introduced into said first universal transfer vector, into a second universal transfer vector comprising a second multiple cloning site which comprises nucleotides 620-772 of the nucleotide sequence set forth in SEQ ID NO: 1; wherein said multiple cloning site is in said orientation or in a reverse orientation; and
   (c) introducing said cassettes from steps (a) and (b) into an amplifiable vector comprising a third multiple cloning site, comprising nucleotides 5037-5183 of the nucleotide sequence set forth in SEQ ID NO: 3; wherein said multiple cloning site is in said orientation or in a reverse orientation; and wherein the cassettes from steps (a) and (b) encode an immunoglobulin light chain and an immunoglobulin heavy chain, of said antibody.

2. The method of claim 1 wherein said first or second cassette comprises a polynucleotide encoding a polypeptide comprising the amino acid sequence set forth in SEQ ID NO: 20 and the other cassette comprises a polynucleotide encoding a polypeptide comprising the amino acid sequence set forth in SEQ ID NO: 22.

3. The method of claim 2 wherein said polynucleotide encoding said polypeptide comprising the amino acid sequence set forth in SEQ ID NO: 20 comprises the nucleotide sequence set forth in SEQ ID NO: 19 and wherein said polynucleotide encoding said polypeptide comprising the amino acid sequence set forth in SEQ ID NO: 22 comprises the nucleotide sequence set forth in SEQ ID NO: 21.

Figure 2:
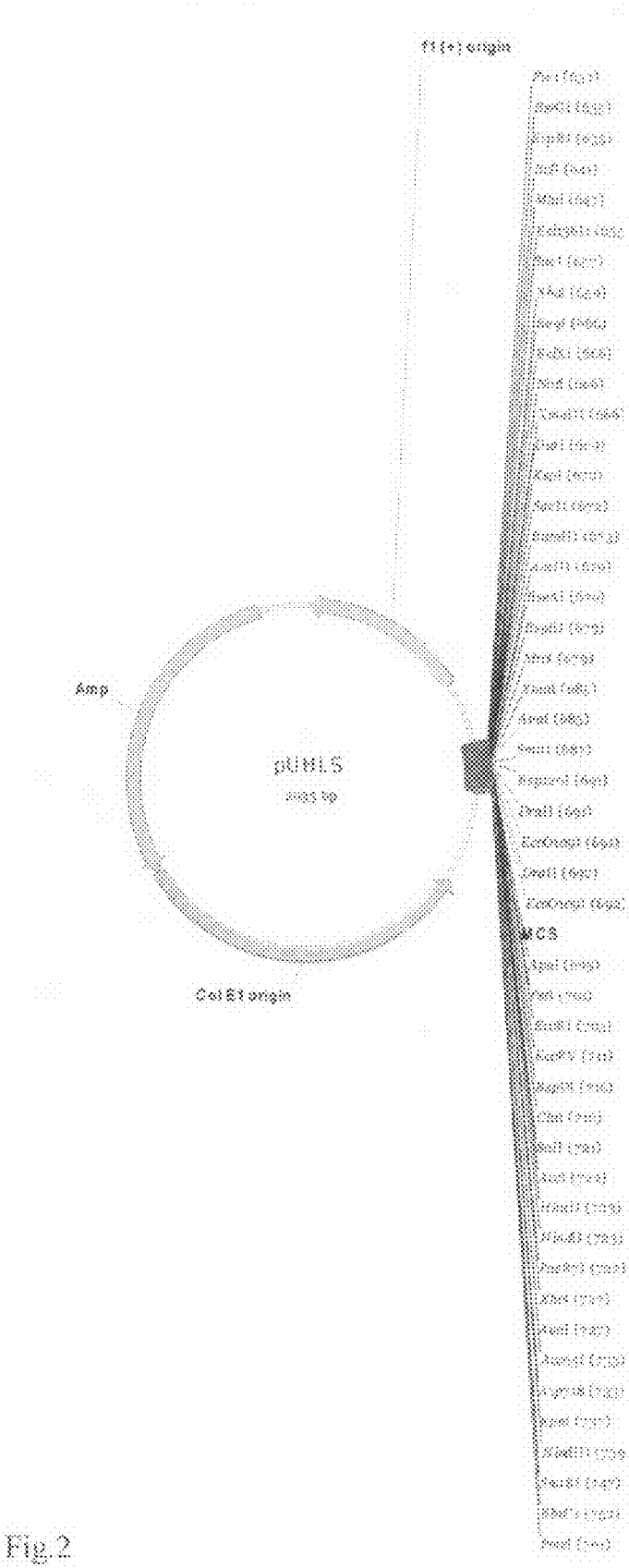
FIG. 2. Plasmid map of universal transfer vector pUHLS.
Amp: Start: 1949 End: 2806
MCS: Start: 620 End: 766
f1 (+) origin: Start: 3 End: 459
Col E1 origin: Start: 1006 End: 1946

4. The method of claim 1 wherein said first universal transfer vector comprises the plasmid map set forth in FIG. 2.

5. The method of claim 1 wherein said second universal transfer vector comprises the plasmid map set forth in FIG. 1.

Figure 3:
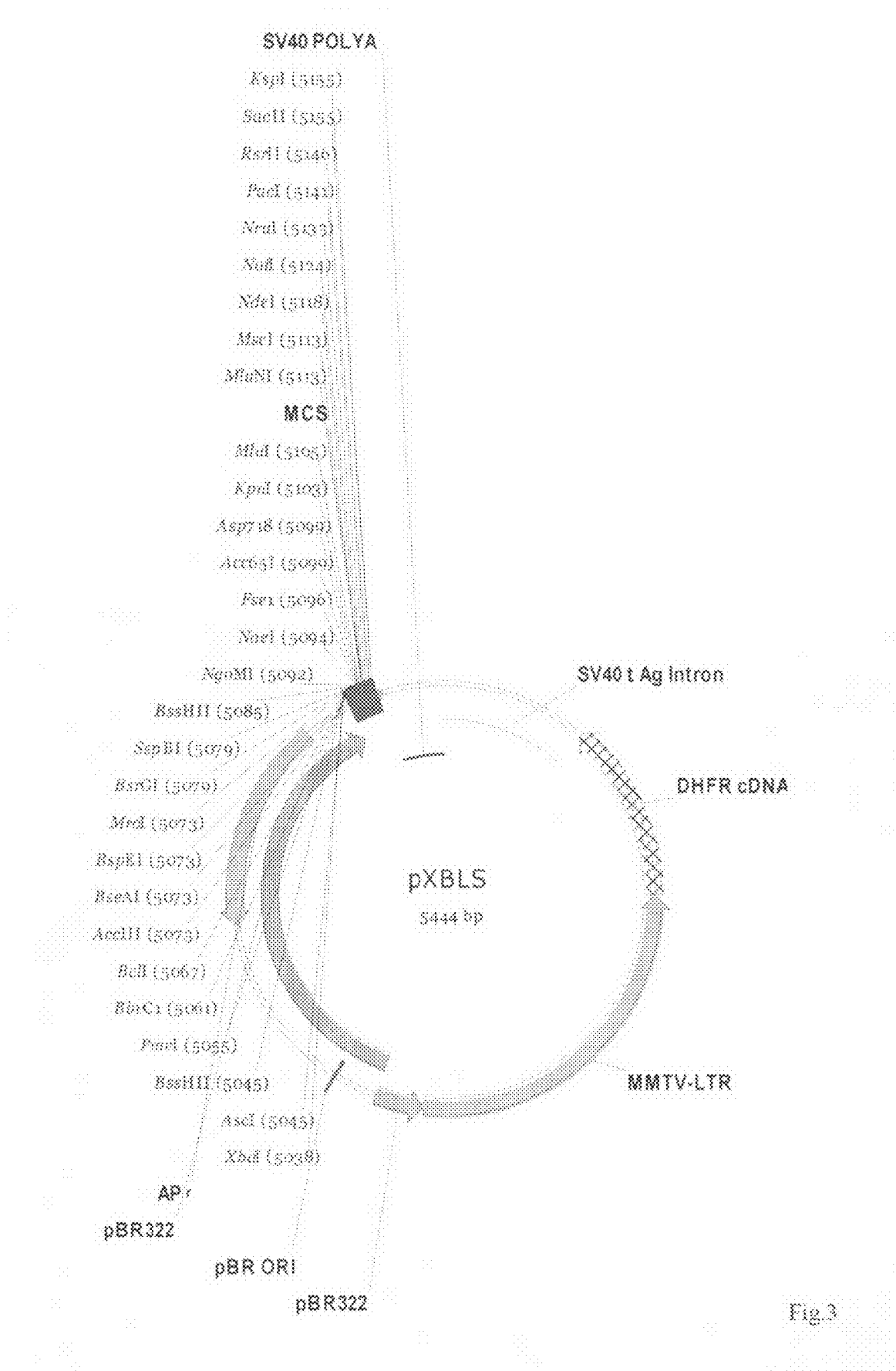
FIG. 3. Plasmid map of amplifiable vector pXBLS.
SV40 T-antigen (t Ag) Intron: Start: 5431 End: 600
SV40 POLY A signal: Start: 5184 End: 5432
MCS: Start: 5037 End: 5183
Ampicillin resistance (Amp): Start: 3965 End: 4828
pBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347.

6. The method of claim 1 wherein said amplifiable vector comprises the plasmid map set forth in FIG. 3.

7. The method of claim 1 wherein said first universal transfer vector comprises the nucleotide sequence set forth in SEQ ID NO: 2.

8. The method of claim 1 wherein said second universal transfer vector comprises the nucleotide sequence set forth in SEQ ID NO: 1.

9. The method of claim 1 wherein said amplifiable vector comprises the nucleotide sequence set forth in SEQ ID NO: 3.

10. The method of claim 1 wherein one set of expression cassettes comprises a polynucleotide, operably associated with a promoter, which polynucleotide encodes an anti-IGFR1 antibody immunoglobulin heavy chain and the other set of expression cassettes comprises a polynucleotide, operably associated with a promoter, which polynucleotide encodes an anti-IGFR1 antibody immunoglobulin light chain.

* * * * *

SEQUENCE LISTING

```
<160> NUMBER OF SEQ ID NOS: 27

<210> SEQ ID NO 1
<211> LENGTH: 2941
<212> TYPE: DNA
<213> ORGANISM: Artificial sequence
<220> FEATURE:
<223> OTHER INFORMATION: pULLs plasmid

<400> SEQUENCE: 1
ctaaattgta agcgttaata ttttgttaaa attcgcgtta aattttgtt aaatcagctc      60 attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgccaccgg tgcccgggc cggtccgact agttacgtaa    660
agcttggtac cctcgaggtc gacatcgatg atatcgaatt cctgcagggg ccctccggag    720
gatccgcggc cgctctagag agctccatat gtggccatcg cgattaatta agcgcgcttg    780
gcgtaatcat ggtcatagct gtttcctgtg tgaaattgtt atccgctcac aattccacac    840
aacatacgag ccggaagcat aaagtgtaaa gcctggggtg cctaatgagt gagctaactc    900
acattaattg cgttgcgctc actgcccgct ttccagtcgg gaaacctgtc gtgccagctg    960
cattaatgaa tcggccaacg cgcggggaga ggcggtttgc gtattgggcg ctcttccgct   1020
tcctcgctca ctgactcgct gcgctcggtc gttcggctgc ggcgagcggt atcagctcac   1080
```

| | |
|---|---:|
| tcaaaggcgg taatacggtt atccacagaa tcaggggata acgcaggaaa gaacatgtga | 1140 |
| gcaaaaggcc agcaaaaggc caggaaccgt aaaaaggccg cgttgctggc gttttccat | 1200 |
| aggctccgcc cccctgacga gcatcacaaa atcgacgct caagtcagag gtggcgaaac | 1260 |
| ccgacaggac tataaagata ccaggcgttt ccccctggaa gctccctcgt gcgctctcct | 1320 |
| gttccgaccc tgccgcttac cggatacctg tccgcctttc tcccttcggg aagcgtggcg | 1380 |
| ctttctcata gctcacgctg taggtatctc agttcggtgt aggtcgttcg ctccaagctg | 1440 |
| ggctgtgtgc acgaaccccc cgttcagccc gaccgctgcg ccttatccgg taactatcgt | 1500 |
| cttgagtcca acccggtaag acacgactta tcgccactgg cagcagccac tggtaacagg | 1560 |
| attagcagag cgaggtatgt aggcggtgct acagagttct tgaagtggtg cctaactac | 1620 |
| ggctacacta aaggacagt atttggtatc tgcgctctgc tgaagccagt taccttcgga | 1680 |
| aaaagagttg gtagctcttg atccggcaaa caaccaccg ctggtagcgg tggtttttt | 1740 |
| gtttgcaagc agcagattac gcgcagaaaa aaggatctc aagaagatcc tttgatcttt | 1800 |
| tctacggggt ctgacgctca gtggaacgaa aactcacgtt aagggatttt ggtcatgaga | 1860 |
| ttatcaaaaa ggatcttcac ctagatcctt ttaaattaaa aatgaagttt taaatcaatc | 1920 |
| taaagtatat atgagtaaac ttggtctgac agttaccaat gcttaatcag tgaggcacct | 1980 |
| atctcagcga tctgtctatt tcgttcatcc atagttgcct gactccccgt cgtgtagata | 2040 |
| actacgatac gggagggctt accatctggc cccagtgctg caatgatacc gcgagaccca | 2100 |
| cgctcaccgg ctccagattt atcagcaata aaccagccag ccggaagggc cgagcgcaga | 2160 |
| agtggtcctg caactttatc cgcctccatc cagtctatta attgttgccg ggaagctaga | 2220 |
| gtaagtagtt cgccagttaa tagtttgcgc aacgttgttg ccattgctac aggcatcgtg | 2280 |
| gtgtcacgct cgtcgtttgg tatggcttca ttcagctccg gttcccaacg atcaaggcga | 2340 |
| gttacatgat cccccatgtt gtgcaaaaaa gcggttagct ccttcggtcc tccgatcgtt | 2400 |
| gtcagaagta agttggccgc agtgttatca ctcatggtta tggcagcact gcataattct | 2460 |
| cttactgtca tgccatccgt aagatgcttt tctgtgactg gtgagtactc aaccaagtca | 2520 |
| ttctgagaat agtgtatgcg gcgaccgagt tgctcttgcc cggcgtcaat acgggataat | 2580 |
| accgcgccac atagcagaac tttaaaagtg ctcatcattg gaaaacgttc ttcggggcga | 2640 |
| aaactctcaa ggatcttacc gctgttgaga tccagttcga tgtaacccac tcgtgcaccc | 2700 |
| aactgatctt cagcatcttt tactttcacc agcgtttctg ggtgagcaaa aacaggaagg | 2760 |
| caaaatgccg caaaaaaggg aataagggcg acacggaaat gttgaatact catactcttc | 2820 |
| ctttttcaat attattgaag catttatcag ggttattgtc tcatgagcgg atacatattt | 2880 |
| gaatgtattt agaaaaataa acaaataggg gttccgcgca catttccccg aaaagtgcca | 2940 |
| c | 2941 |

<210> SEQ ID NO 2
<211> LENGTH: 2935
<212> TYPE: DNA
<213> ORGANISM: Artificial sequence
<220> FEATURE:
<223> OTHER INFORMATION: pUHLS plasmid

<400> SEQUENCE: 2

| | |
|---|---:|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gatagggttg agtgttgttc cagtttggaa caagagtcca ctattaaaga acgtggactc | 180 |

-continued

```
caacgtcaaa gggcgaaaaa ccgtctatca gggcgatggc ccactacgtg aaccatcacc    240
ctaatcaagt ttttgggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgccgttta accctcagc tacgtaaagc ttggtaccct     660
cgaggtcgac atcgatgata tcgaattcct gcaggggccc cccgggtccg gaggatccgc    720
ggccgctcta gagagctcac gcgttgatca tgtacaggcc ggccagcgcg cttggcgtaa    780
tcatggtcat agctgtttcc tgtgtgaaat tgttatccgc tcacaattcc acacaacata    840
cgagccggaa gcataaagtg taaagcctgg ggtgcctaat gagtgagcta actcacatta    900
attgcgttgc gctcactgcc cgcttttcag tcgggaaacc tgtcgtgcca gctgcattaa    960
tgaatcggcc aacgcgcggg gagaggcggt ttgcgtattg ggcgctcttc cgcttcctcg   1020
ctcactgact cgctgcgctc ggtcgttcgg ctgcggcgag cggtatcagc tcactcaaag   1080
gcggtaatac ggttatccac agaatcaggg gataacgcag gaaagaacat gtgagcaaaa   1140
ggccagcaaa aggccaggaa ccgtaaaaag gccgcgttgc tggcgttttt ccataggctc   1200
cgcccccctg acgagcatca caaaaatcga cgctcaagtc agaggtggcg aaacccgaca   1260
ggactataaa gataccaggc gtttccccct ggaagctccc tcgtgcgctc tcctgttccg   1320
accctgccgc ttaccggata cctgtccgcc tttctccctt cgggaagcgt ggcgctttct   1380
catagctcac gctgtaggta tctcagttcg gtgtaggtcg ttcgctccaa gctgggctgt   1440
gtgcacgaac cccccgttca gcccgaccgc tgcgccttat ccggtaacta tcgtcttgag   1500
tccaacccgg taagacacga cttatcgcca ctggcagcag ccactggtaa caggattagc   1560
agagcgaggt atgtaggcgg tgctacagag ttcttgaagt ggtggcctaa ctacggctac   1620
actagaagga cagtatttgg tatctgcgct ctgctgaagc cagttacctt cggaaaaaga   1680
gttggtagct cttgatccgg caaacaaacc accgctggta gcggtggttt ttttgtttgc   1740
aagcagcaga ttacgcgcag aaaaaaagga tctcaagaag atcctttgat cttttctacg   1800
gggtctgacg ctcagtggaa cgaaaactca cgttaaggga ttttggtcat gagattatca   1860
aaaaggatct tcacctagat ccttttaaat taaaaatgaa gttttaaatc aatctaaagt   1920
atatatgagt aaacttggtc tgacagttac caatgcttaa tcagtgaggc acctatctca   1980
gcgatctgtc tatttcgttc atccatagtt gcctgactcc ccgtcgtgta gataactacg   2040
atacgggagg gcttaccatc tggccccagt gctgcaatga taccgcgaga cccacgctca   2100
ccggctccag atttatcagc aataaaccag ccagccggaa gggccgagcg cagaagtggt   2160
cctgcaactt tatccgcctc catccagtct attaattgtt gccgggaagc tagagtaagt   2220
agttcgccag ttaatagttt gcgcaacgtt gttgccattg ctacaggcat cgtggtgtca   2280
cgctcgtcgt ttggtatggc ttcattcagc tccggttccc aacgatcaag gcgagttaca   2340
tgatccccca tgttgtgcaa aaaagcggtt agctccttcg gtcctccgat cgttgtcaga   2400
agtaagttgg ccgcagtgtt atcactcatg gttatggcag cactgcataa ttctcttact   2460
gtcatgccat ccgtaagatg cttttctgtg actggtgagt actcaaccaa gtcattctga   2520
gaatagtgta tgcggcgacc gagttgctct tgcccggcgt caatacggga taataccgcg   2580
```

```
ccacatagca gaactttaaa agtgctcatc attggaaaac gttcttcggg gcgaaaactc    2640
tcaaggatct taccgctgtt gagatccagt tcgatgtaac ccactcgtgc acccaactga    2700
tcttcagcat cttttacttt caccagcgtt tctgggtgag caaaaacagg aaggcaaaat    2760
gccgcaaaaa agggaataag ggcgacacgg aaatgttgaa tactcatact cttcctttt     2820 caatattatt gaagcattta tcagggttat tgtctcatga gcggatacat atttgaatgt    2880
atttagaaaa ataaacaaat aggggttccg cgcacatttc cccgaaaagt gccac         2935
```

<210> SEQ ID NO 3
<211> LENGTH: 5444
<212> TYPE: DNA
<213> ORGANISM: Artificial sequence
<220> FEATURE:
<223> OTHER INFORMATION: pXBLS plasmid

<400> SEQUENCE: 3

```
gcactataca tcaaatattc cttattaacc cctttacaaa ttaaaaagct aaaggtacac      60 aattttgag catagttatt aatagcagac actctatgcc tgtgtggagt aagaaaaaac     120
agtatgttat gattataact gttatgccta cttataaagg ttacagaata ttttccata     180 attttcttgt atagcagtgc agcttttcc tttgtggtgt aaatagcaaa gcaagcaaga     240
gttctattac taaacacagc atgactcaaa aaacttagca attctgaagg aaagtccttg    300
gggtcttcta cctttctctt ctttttgga ggagtagaat gttgagagtc agcagtagcc     360
tcatcatcac tagatggcat ttcttctgag caaaacaggg tttcctcatt aaaggcattc    420
caccactgct cccattcatc agttccatag gttggaatct aaaatacaca aacaattaga    480
atcagtagtt taacacatta tacttaaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga aagtttata    780 tttccccaaa tcaattctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt ccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg ggaccctct ggaaagtgaa ggataagtga   1560
cgagcggaga cgggatggcg aacagacaca acacacaag aggtgaatgt taggactgtt   1620
gcaagtttac tcaaaaaatc agcactcttt tatatcttgg tttacataag catttacata   1680
agatttggat aaaattccaaa agaacatagg aaaatagaac actcagagct cagatcagaa   1740
```

```
cctttgatac caaaccaagt caggaaacca cttgtctcac atcctcgttt taagaacagt    1800
ttgtaaccaa aaacttactt aagccctggg aaccgcaagg ttgggccaat aaaggctatt    1860
cataataact catgccatga gttttttgcag aataatgttc tattagtcca gccactgtcc   1920
cctccttggt atggaaaatc ttttccccaaa agtgcattcc tgttcctaga taaatataat   1980
catgtacctg ttgttttcatg tcgtcttttt cttcttgaga caacatacac caaggaggtc   2040
tagctctggc gagtctttca cgaaaaggga gggatctata taacactttta tagccattga   2100
ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actctttttt ccctttttta cttctaggcc tgtggtcaat agtccttgca    2280
cctgttcttc aattgaggtt gagcgtctct ttctattttc tattcccatt tctaacttct    2340
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca agtttgcagc agagaatgaa tatgtctttg tctgatgggc    2700
tcatccgttt gtgcgcagac gggtcgtcct tggtgggaaa caaccccttg gctgcttctc    2760
ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag cataggctt    2940
ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga aagaacatgt gagcaaaagg ccagcaaaag gccaggaacc    3180
gtaaaaaggc cgcgttgctg gcgtttttcc ataggctccg ccccctgac gagcatcaca    3240
aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc aacccggta agacacgact    3540
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt ttgtttgcaa gcagcagatt acgcgcagaa    3780
aaaaaggatc tcaagaagat cctttgatct ttttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
```

```
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca acacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
cgacacggaa atgttgaata ctcatactct tcctttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgcc gtttaaaccc tcagctgatc atccggatgt acagcgcgcg gccggccggt    5100
accacgcgtt ggccacatat ggcggccgct cgcgattaat taacggaccg ccgcggacta    5160
gtgcccgggc caccggtgct cgaagcttgg atcgatccag acatgataag atacattgat    5220
gagtttggac aaaccacaac tagaatgcag tgaaaaaaat gctttatttg tgaaatttgt    5280
gatgctattg ctttatttgt aaccattata agctgcaata acaagttaa caacaacaat     5340 tgcattcatt ttatgtttca ggttcagggg gaggtgtggg aggttttta aagcaagtaa     5400 aacctctaca aatgtggtat ggctgattat gatctctagt caag                     5444
```

<210> SEQ ID NO 4
<211> LENGTH: 3176
<212> TYPE: DNA
<213> ORGANISM: Artificial sequence
<220> FEATURE:
<223> OTHER INFORMATION: pULstopLs plasmid

<400> SEQUENCE: 4

```
ctaaattgta agcgttaata ttttgttaaa attcgcgtta aattttttgtt aaatcagctc      60 atttttaac caataggccg aaatcggcaa atcccttat aaatcaaaag aatagaccga       120 gataggttg agtgttgttc cagttttgga caagagtcca ctattaaaga acgtggactc      180
caacgtcaaa gggcgaaaaa ccgtctatca gggcgatggc ccactacgtg aaccatcacc     240
ctaatcaagt tttttggggt cgaggtgccg taaagcacta atcggaacc ctaaagggag      300 ccccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgccaccgg tgcccgggc cggtccgact agttacgtaa   660
agcttggtac cctcgaggtc gacatcgatg atatcgaatt cctgcagggg ccctccggag   720
gatccagatc cccctcgctt tcttgctgtc caatttctat taaaggttcc tttgttccct   780
```

```
aagtccaact actaaactgg gggatattat gaagggcctt gagcatctgg attctgccta      840
ataaaaaaca tttattttca ttgcaatgat gtatttaaat tatttctgaa tattttacta      900
aaaagggaat gtgggaggtc agtgcattta aaacataaag aaatgaagag ggggatctgt      960
cgacaagctc tagagagctc catatgtggc catcgcgatt aattaagcgc gcttggcgta     1020
atcatggtca tagctgtttc ctgtgtgaaa ttgttatccg ctcacaattc cacacaacat     1080
acgagccgga agcataaagt gtaaagcctg gggtgcctaa tgagtgagct aactcacatt     1140
aattgcgttg cgctcactgc ccgctttcca gtcgggaaac ctgtcgtgcc agctgcatta     1200
atgaatcggc caacgcgcgg ggagaggcgg tttgcgtatt gggcgctctt ccgcttcctc     1260
gctcactgac tcgctgcgct cggtcgttcg gctgcggcga gcggtatcag ctcactcaaa     1320
ggcggtaata cggttatcca cagaatcagg ggataacgca ggaaagaaca tgtgagcaaa     1380
aggccagcaa aaggccagga accgtaaaaa ggccgcgttg ctggcgtttt tccataggct     1440
ccgcccccct gacgagcatc acaaaaatcg acgctcaagt cagaggtggc gaaacccgac     1500
aggactataa agataccagg cgtttccccc tggaagctcc ctcgtgcgct ctcctgttcc     1560
gaccctgccg cttaccggat acctgtccgc ctttctccct tcgggaagcg tggcgctttc     1620
tcatagctca cgctgtaggt atctcagttc ggtgtaggtc gttcgctcca agctgggctg     1680
tgtgcacgaa ccccccgttc agcccgaccg ctgcgcctta tccggtaact atcgtcttga     1740
gtccaacccg gtaagacacg acttatcgcc actggcagca gccactggta acaggattag     1800
cagagcgagg tatgtaggcg gtgctacaga gttcttgaag tggtggccta actacggcta     1860
cactagaagg acagtatttg gtatctgcgc tctgctgaag ccagttacct tcggaaaaag     1920
agttggtagc tcttgatccg gcaaacaaac caccgctggt agcggtggtt tttttgtttg     1980
caagcagcag attacgcgca gaaaaaagg atcctttga tcttttctac                  2040 ggggtctgac gctcagtgga acgaaaactc acgttaaggg attttggtca tgagattatc     2100
aaaaaggatc ttcacctaga tccttttaaa ttaaaaatga agttttaaat caatctaaag     2160
tatatatgag taaacttggt ctgacagtta ccaatgctta atcagtgagg cacctatctc     2220
agcgatctgt ctatttcgtt catccatagt tgcctgactc cccgtcgtgt agataactac     2280
gatacgggag ggcttaccat ctggccccag tgctgcaatg ataccgcgag acccacgctc     2340
accggctcca gatttatcag caataaacca gccagccgga agggccgagc gcagaagtgg     2400
tcctgcaact ttatccgcct ccatccagtc tattaattgt tgccgggaag ctagagtaag     2460
tagttcgcca gttaatagtt tgcgcaacgt tgttgccatt gctacaggca tcgtggtgtc     2520
acgctcgtcg tttggtatgg cttcattcag ctccggttcc caacgatcaa ggcgagttac     2580
atgatccccc atgttgtgca aaaaagcggt tagctccttc ggtcctccga tcgttgtcag     2640
aagtaagttg gccgcagtgt tatcactcat ggttatggca gcactgcata attctcttac     2700
tgtcatgcca tccgtaagat gcttttctgt gactggtgag tactcaacca agtcattctg     2760
agaatagtgt atgcggcgac cgagttgctc ttgcccggcg tcaatacggg ataataccgc     2820
gccacatagc agaactttaa aagtgctcat cattggaaaa cgttcttcgg ggcgaaaact     2880
ctcaaggatc ttaccgctgt tgagatccag ttcgatgtaa cccactcgtg cacccaactg     2940
atcttcagca tcttttactt tcaccagcgt ttctgggtgt gcaaaaacag gaaggcaaaa     3000
tgccgcaaaa aagggaataa gggcgacacg gaaatgttga atactcatac tcttcctttt     3060
tcaatattat tgaagcattt atcagggtta ttgtctcatg agcggataca tatttgaatg     3120
tatttagaaa aataaacaaa tagggggttcc gcgcacattt ccccgaaaag tgccac       3176
```

<210> SEQ ID NO 5
<211> LENGTH: 3170
<212> TYPE: DNA
<213> ORGANISM: Artificial sequence
<220> FEATURE:
<223> OTHER INFORMATION: pUHstopLS plasmid

<400> SEQUENCE: 5

| | | | | | |
|---|---|---|---|---|---|
| ctaaattgta | agcgttaata | ttttgttaaa | attcgcgtta | aattttttgtt | aaatcagctc | 60 |
| attttttaac | aataggccg | aaatcggcaa | atcccttat | aaatcaaaag | aatagaccga | 120 |
| gatagggttg | agtgttgttc | cagtttggaa | caagagtcca | ctattaaaga | acgtggactc | 180 |
| caacgtcaaa | gggcgaaaaa | ccgtctatca | gggcgatggc | ccactacgtg | aaccatcacc | 240 |
| ctaatcaagt | tttttggggt | cgaggtgccg | taaagcacta | aatcggaacc | ctaaagggag | 300 |
| cccccgattt | agagcttgac | ggggaaagcc | ggcgaacgtg | gcgagaaagg | aagggaagaa | 360 |
| agcgaaagga | gcgggcgcta | gggcgctggc | aagtgtagcg | gtcacgctgc | gcgtaaccac | 420 |
| cacacccgcc | gcgcttaatg | cgccgctaca | gggcgcgtcc | cattcgccat | tcaggctgcg | 480 |
| caactgttgg | gaagggcgat | cggtgcgggc | ctcttcgcta | ttacgccagc | tggcgaaagg | 540 |
| gggatgtgct | gcaaggcgat | taagttgggt | aacgccaggg | ttttcccagt | cacgacgttg | 600 |
| taaaacgacg | gccagtgagc | gcgcgtttta | accctcagc | tacgtaaagc | ttggtaccct | 660 |
| cgaggtcgac | atcgatgata | tcgaattcct | gcaggggccc | cccgggtccg | gaggatccag | 720 |
| atccccctcg | ctttcttgct | gtccaatttc | tattaaaggt | tcctttgttc | cctaagtcca | 780 |
| actactaaac | tgggggatat | tatgaagggc | cttgagcatc | tggattctgc | ctaataaaaa | 840 |
| acatttattt | tcattgcaat | gatgtattta | aattatttct | gaatatttta | ctaaaaaggg | 900 |
| aatgtgggag | gtcagtgcat | ttaaaacata | agaaatgaa | gaggggggatc | tgtcgacaag | 960 |
| ctctagagac | ctcacgcgtt | gatcatgtac | aggccggca | gcgcgcttgg | cgtaatcatg | 1020 |
| gtcatagctg | tttcctgtgt | gaaattgtta | tccgctcaca | attccacaca | acatacgagc | 1080 |
| cggaagcata | aagtgtaaag | cctggggtgc | ctaatgagtg | agctaactca | cattaattgc | 1140 |
| gttgcgctca | ctgcccgctt | tccagtcggg | aaacctgtcg | tgccagctgc | attaatgaat | 1200 |
| cggccaacgc | gcggggagag | gcggtttgcg | tattgggcgc | tcttccgctt | cctcgctcac | 1260 |
| tgactcgctg | cgctcggtcg | ttcggctgcg | gcgagcggta | tcagctcact | caaaggcggt | 1320 |
| aatacggtta | tccacagaat | caggggataa | cgcaggaaag | aacatgtgag | caaaaggcca | 1380 |
| gcaaaaggcc | aggaaccgta | aaaaggccgc | gttgctggcg | ttttccata | ggctccgccc | 1440 |
| ccctgacgag | catcacaaaa | atcgacgctc | aagtcagagg | tggcgaaacc | cgacaggact | 1500 |
| ataaagatac | caggcgtttc | ccctggaag | ctccctcgtg | cgctctcctg | ttccgaccct | 1560 |
| gccgcttacc | ggatacctgt | ccgcctttct | cccttcggga | agcgtggcgc | tttctcatag | 1620 |
| ctcacgctgt | aggtatctca | gttcggtgta | ggtcgttcgc | tccaagctgg | gctgtgtgca | 1680 |
| cgaaccccc | gttcagcccg | accgctgcgc | cttatccggt | aactatcgtc | ttgagtccaa | 1740 |
| cccggtaaga | cacgacttat | cgccactggc | agcagccact | ggtaacagga | ttagcagagc | 1800 |
| gaggtatgta | ggcggtgcta | cagagttctt | gaagtggtgg | cctaactacg | gctacactag | 1860 |
| aaggacagta | tttggtatct | gcgctctgct | gaagccagtt | accttcggaa | aaagagttgg | 1920 |
| tagctcttga | tccggcaaac | aaaccaccgc | tggtagcggt | ggtttttttg | tttgcaagca | 1980 |
| gcagattacg | cgcagaaaaa | aaggatctca | agaagatcct | ttgatctttt | ctacggggtc | 2040 |
| tgacgctcag | tggaacgaaa | actcacgtta | agggattttg | gtcatgagat | tatcaaaaag | 2100 |

```
gatcttcacc tagatccttt taaattaaaa atgaagtttt aaatcaatct aaagtatata    2160
tgagtaaact tggtctgaca gttaccaatg cttaatcagt gaggcaccta tctcagcgat    2220
ctgtctattt cgttcatcca tagttgcctg actcccgtc  gtgtagataa ctacgatacg    2280
ggagggctta ccatctggcc ccagtgctgc aatgataccg cgagacccac gctcaccggc    2340
tccagattta tcagcaataa accagccagc cggaagggcc gagcgcagaa gtggtcctgc    2400
aactttatcc gcctccatcc agtctattaa ttgttgccgg gaagctagag taagtagttc    2460
gccagttaat agtttgcgca acgttgttgc cattgctaca ggcatcgtgg tgtcacgctc    2520
gtcgtttggt atggcttcat tcagctccgg ttcccaacga tcaaggcgag ttacatgatc    2580
ccccatgttg tgcaaaaaag cggttagctc cttcggtcct ccgatcgttg tcagaagtaa    2640
gttggccgca gtgttatcac tcatggttat ggcagcactg cataattctc ttactgtcat    2700
gccatccgta agatgctttt ctgtgactgg tgagtactca accaagtcat tctgagaata    2760
gtgtatgcgg cgaccgagtt gctcttgccc ggcgtcaata cggataata  ccgcgccaca    2820 tagcagaact ttaaaagtgc tcatcattgg aaaacgttct cggggcgaa  aactctcaag    2880 gatcttaccg ctgttgagat ccagttcgat gtaacccact cgtgcaccca actgatcttc    2940
agcatctttt actttcacca gcgtttctgg gtgagcaaaa acaggaaggc aaaatgccgc    3000
aaaaaaggga ataagggcga cacggaaatg ttgaatactc atactcttcc ttttcaata    3060 ttattgaagc atttatcagg gttattgtct catgagcgga tacatatttg aatgtattta    3120
gaaaaataaa caatagggg  ttccgcgcac atttccccga aaagtgccac              3170

<210> SEQ ID NO 6
<211> LENGTH: 12190
<212> TYPE: DNA
<213> ORGANISM: Artificial sequence
<220> FEATURE:
<223> OTHER INFORMATION: pAIL5V1 plasmid

<400> SEQUENCE: 6
gcactataca tcaaatattc cttattaacc cctttacaaa ttaaaaagct aaaggtacac      60
aatttttgag catagttatt aatagcagac actctatgcc tgtgtggagt aagaaaaaac     120
agtatgttat gattataact gttatgccta cttataaagg ttacagaata ttttccata     180 attttcttgt atagcagtgc agcttttcc  tttgtggtgt aaatagcaaa gcaagcaaga     240
gttctattac taaacacagc atgactcaaa aacttagca  attctgaagg aaagtccttg     300
gggtcttcta ccctttctctt ctttttgga ggagtagaat gttgagagtc agcagtagcc     360
tcatcatcac tagatggcat tcttctgag  caaaacaggt tttcctcatt aaaggcattc     420
caccactgct cccattcatc agttccatag gttggaatct aaaatacaca aacaattaga     480
atcagtagtt taacacatta tacacttaaa aattttatat ttaccttaga gctttaaatc     540
tctgtaggta gtttgtccaa ttatgtcaca ccacagaagt aaggttcctt cacaaagatc     600
gatctaaagc cagcaaaagt cccatggtct tataaaaatg catagcttta ggaggggagc     660
agagaacttg aaagcatctt cctgttagtc tttcttctcg tagacttcaa acttatactt     720
gatgcctttt tcctcctgga cctcagagag gacgcctggg tattctggga gaagtttata     780
tttccccaaa tcaatttctg ggaaaaacgt gtcactttca aattcctgca tgatccttgt     840
cacaaagagt ctgaggtggc ctggttgatt catggcttcc tggtaaacag aactgcctcc     900
gactatccaa accatgtcta ctttacttgc caattccggt tgttcaataa gtcttaaggc     960
atcatccaaa cttttggcaa gaaaatgagc tcctcgtggt ggttctttga gttctctact    1020
```

```
gagaactata ttaattctgt cctttaaagg tcgattcttc tcaggaatgg agaaccaggt    1080
tttcctaccc ataatcacca gattctgttt accttccact gaagaggttg tggtcattct    1140
ttggaagtac ttgaactcgt tcctgagcgg aggccaggt aggtctccgt tcttgccaat     1200
ccccatattt tgggacacgg cgacgatgca gttcaatggt cgaaccatga tggcagcggg    1260
gataaaatcc taccagcctt cacgctagga ttgccgtcaa gtttggcgcg aaatcgcagc    1320
cctgagctgt ccccccccc aagctcagat ctgagcttgg tccctatggt gagtccgttc     1380
cgctcttgtg atgatagcca gacaagaaag agacaataca agacaaacac caaatagtag    1440
aaatagagac aagggtcact tatccgaggg tccctgttcg ggcgccagct gccgcagtcg    1500
gccgacctga gggtcgccgg ggtctgcggg gggaccctct ggaaagtgaa ggataagtga    1560
cgagcggaga cgggatggcg aacagacaca aacacacaag aggtgaatgt taggactgtt    1620
gcaagtttac tcaaaaaatc agcactcttt tatatcttgg tttacataag catttacata    1680
agatttggat aaattccaaa agaacatagg aaaatagaac actcagagct cagatcagaa    1740
cctttgatac caaccaagt caggaaacca cttgtctcac atcctcgttt taagaacagt     1800
ttgtaaccaa aaacttactt aagccctggg aaccgcaagg ttgggccaat aaaggctatt    1860
cataataact catgccatga gtttttgcag aataatgttc tattagtcca gccactgtcc    1920
cctccttggt atggaaaatc tttccccaaa agtgcattcc tgttcctaga taatataat     1980 catgtacctg ttgtttcatg tcgtcttttt cttcttgaga caacatacac caaggaggtc    2040
tagctctggc gagtctttca cgaaaaggga gggatctata taacacttta tagccattga    2100
ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actcttttt cccttttta cttctaggcc tgtggtcaat agtccttgca      2280
cctgttcttc aattgaggtt gagcgtctct ttctattttc tattcccatt tctaacttct    2340
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca agtttgcagc agagaatgaa tatgtctttg tctgatgggc    2700
tcatccgttt gtgcgcagac gggtcgtcct tggtgggaaa caaccccttg gctgcttctc    2760
ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag catcaggctt    2940
ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga aagaacatgt gagcaaaagg ccagcaaaag gccaggaacc    3180
gtaaaaaggc cgcgttgctg cgttttttcc ataggctccg ccccctgac gagcatcaca     3240 aaaatcgacg ctcaagtcag aggtggcgaa acccgacagg actataaaga taccaggcgt    3300 ttcccctgg aagctccctc gtgcgctctc ctgttccgac cctgccgctt accggatacc     3360
tgtccgcctt tctcccttcg ggaagcgtgg cgctttctca tagctcacgc tgtaggtatc    3420
```

```
tcagttcggt gtaggtcgtt cgctccaagc tgggctgtgt gcacgaaccc cccgttcagc    3480
ccgaccgctg cgccttatcc ggtaactatc gtcttgagtc caacccggta agacacgact    3540
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg aaaaagagt tggtagctct tgatccggca     3720
aacaaaccac cgctggtagc ggtggttttt ttgtttgcaa gcagcagatt acgcgcagaa    3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atccccatg ttgtgcaaaa     4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca acacgggata ataccgcgcc acatagcaga actttaaaag    4620
tgctcatcat tggaaaacgt tcttcgggc gaaaactctc aaggatctta ccgctgttga     4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
cgacacggaa atgttgaata ctcatactct tcctttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgcc gtttaaaccc tcagctaccg atgtacgggc cagatatacg cgttgacatt    5100
gattattgac tagttattaa tagtaatcaa ttacggggtc attagttcat agcccatata    5160
tggagttccg cgttacataa cttacggtaa atggcccgcc tggctgaccg cccaacgacc    5220
cccgcccatt gacgtcaata atgacgtatg ttcccatagt aacgccaata gggactttcc    5280
attgacgtca atgggtggac tatttacggt aaactgccca cttggcagta catcaagtgt    5340
atcatatgcc aagtacgccc cctattgacg tcaatgacgg taaatggccc gcctggcatt    5400
atgcccagta catgacctta tgggactttc ctacttggca gtacatctac gtattagtca    5460
tcgctattac catggtgatg cggttttggc agtacatcaa tgggcgtgga tagcggtttg    5520
actcacgggg atttccaagt ctccacccca ttgacgtcaa tgggagtttg ttttggcacc    5580
aaaatcaacg ggactttcca aaatgtcgta acaactccgc cccattgacg caaatgggcg    5640
gtaggcgtgt acggtgggag gtctatataa gcagagctct ctggctaact agagaaccca    5700
ctgcttactg gcttatcgaa attaatacga ctcactatag ggagaccaa gctggctagc     5760
gtttaaactt aagcttggta ccgagctcgg atccactagt ccagtgtggt ggaattccag    5820
```

```
agagaactca ccatggagtt tgggctgagc tggcttttc ttgtggctat tttaaaaggt   5880
gtccagtgtg aggtgcagct gttggagtct gggggaggct tggtacagcc tggggggtcc   5940
ctgagactct cctgtgcagc ctctggattc acctttagca gctatgccat gagctgggtc   6000
cgccaggctc cagggaaggg gctggagtgg gtctcaacta ttagtggtag tggtggtagc   6060
acatactacg cagactccgt gaagggccgg ttcaccatct ccagagacaa ttccaagaac   6120
acgctgtatc tgcaaatgaa cagcctgaga gccgaggaca cggccgtata ttactgtgcg   6180
aaagagaggt ataactggaa ctacctacac tactggggcc agggaaccct ggtcaccgtc   6240
tcctcagcta gcaccaaggg cccatccgtc ttcccctgg cgccctgctc caggagcacc   6300
tccgagagca cagccgccct gggctgcctg gtcaaggact acttccccga accggtgacg   6360
gtgtcgtgga actcaggcgc cctgaccagc ggcgtgcaca ccttcccggc tgtcctacag   6420
tcctcaggac tctactccct cagcagcgtg gtgaccgtgc cctccagcag cttgggcacg   6480
aagacctaca cctgcaacgt agatcacaag cccagcaaca ccaaggtgga caagagagtt   6540
ggtgagaggc cagcacaggg agggagggtg tctgctggaa gccaggctca gccctcctgc   6600
ctggacgcac cccggctgtg cagccccagc ccagggcagc aaggcatgcc ccatctgtct   6660
cctcacccgg aggcctctga ccaccccact catgctcagg gagagggtct tctggatttt   6720
tccaccaggc tccgggcagc cacaggctgg atgcccctac cccaggccct gcgcatacag   6780
gggcaggtgc tgcgctcaga cctgccaaga gccatatccg ggaggaccct gcccctgacc   6840
taagcccacc ccaaaggcca aactctccac tccctcagct cagacacctt ctctcctccc   6900
agatctgagt aactcccaat cttctctctg cagagtccaa atatggtccc ccatgcccat   6960
catgcccagg taagccaacc caggcctcgc cctccagctc aaggcgggac aggtgcccta   7020
gagtagcctg catccaggga caggccccag ccgggtgctg acgcatccac ctccatctct   7080
tcctcagcac ctgagttcct gggggaccca tcagtcttcc tgttccccc aaaacccaag   7140 gacactctca tgatctcccg gacccctgag gtcacgtgcg tggtggtgga cgtgagccag   7200
gaagaccccg aggtccagtt caactggtac gtggatggcg tggaggtgca taatgccaag   7260
acaaagccgc gggaggagca gttcaacagc acgtaccgtg tggtcagcgt cctcaccgtc   7320
ctgcaccagg actggctgaa cggcaaggag tacaagtgca aggtctccaa caaaggcctc   7380
ccgtcctcca tcgagaaaac catctccaaa gccaaaggtg ggacccacgg ggtgcgaggg   7440
ccacatggac agaggtcagc tcggcccacc ctctgccctg ggagtgaccg ctgtgccaac   7500
ctctgtccct acagggcagc cccgagagcc acaggtgtac accctgcccc catcccagga   7560
ggagatgacc aagaaccagg tcagcctgac ctgcctggtc aaaggcttct accccagcga   7620
catcgccgtg gagtgggaga gcaatgggca gccggagaac aactacaaga ccacgcctcc   7680
cgtgctggac tccgacggct ccttcttcct ctacagcagg ctaaccgtgg acaagagcag   7740
gtggcaggag gggaatgtct tctcatgctc cgtgatgcat gaggctctgc acaaccacta   7800
cacacagaag agcctctccc tgtctctggg taaatgagtg ccaggccgg caagcccccg   7860 ctccccgggt ccgaggatc cagatccccc tcgctttctt gctgtccaat ttctattaaa   7920
ggttcctttg ttccctaagt ccaactacta aactggggga tattatgaag ggccttgagc   7980
atctggattc tgcctaataa aaacatttta ttttcattgc aatgatgtat ttaaattatt   8040
tctgaatatt ttactaaaaa gggaatgtgg gaggtcagtg catttaaaac ataaagaaat   8100 gaagagggg atctgtcgac aagctctaga gagctcacgc gttgatcatg tacaggccgg   8160
cctgtgccac tgggcgccag aaatccgcgc ggtggttttt gggggtcggg ggtgtttggc   8220
```

```
agccacagac gcccggtgtt cgtgtcgcgc cagtacatgc ggtccatgcc caggccatcc   8280
aaaaaccatg ggtctgtctg ctcagtccag tcgtggacca gaccccacgc aacgcccaaa   8340
ataataaccc ccacgaacca taaaccattc cccatggggg accccgtccc taacccacgg   8400
ggccagtggc tatggcaggg cctgccgccc cgacgttggc tgcgagccct gggccttcac   8460
ccgaacttgg ggggtggggt ggggaaaagg aagaaacgcg ggcgtattgg ccccaatggg   8520
gtctcggtgg ggtatcgaca gagtgccagc cctgggaccg aaccccgcgt ttatgaacaa   8580
acgacccaac acccgtgcgt tttattctgt cttttttattg ccgtcatagc gcgggttcct   8640
tccggtattg tctccttccg tgtttcagtt agcctccccc atctcccta ttcctttgcc   8700 ctcggacgag tgctggggcg tcggtttcca ctatcggcga gtacttctac acagccatcg   8760
gtccagacgg ccgcgcttct gcgggcgatt tgtgtacgcc cgacagtccc ggctccggat   8820
cggacgattg cgtcgcatcg accctgcgcc caagctgcat catcgaaatt gccgtcaacc   8880
aagctctgat agagttggtc aagaccaatg cggagcatat acgcccggag ccgcggcgat   8940
cctgcaagct ccggatgcct ccgctcgaag tagcgcgtct gctgctccat acaagccaac   9000
cacggcctcc agaagaagat gttggcgacc tcgtattggg aatccccgaa catcgcctcg   9060
ctccagtcaa tgaccgctgt tatgcggcca ttgtccgtca ggacattgtt ggagccgaaa   9120
tccgcgtgca cgaggtgccg gacttcgggg cagtcctcgg cccaaagcat cagctcatcg   9180
agagcctgcg cgacggacgc actgacggtg tcgtccatca cagtttgcca gtgatacaca   9240
tggggatcag caatcgcgca tatgaaatca cgccatgtag tgtattgacc gattccttgc   9300
ggtccgaatg ggccgaaccc gctcgtctgg ctaagatcgg ccgcagcgat cgcatccatg   9360
gcctccgcga ccggctgcag aacagcgggc agttcggttt caggcaggtc ttgcaacgtg   9420
acaccctgtg cacggcggga gatgcaatag gtcaggctct cgctgaattc cccaatgtca   9480
agcacttccg gaatcgggag cgcggccgat gcaaagtgcc gataaacata acgatctttg   9540
tagaaaccat cggcgcagct atttacccgc aggacatatc cacgccctcc tacatcgaag   9600
ctgaaagcac gagattcttc gccctccgag agctgcatca ggtcggagac gctgtcgaac   9660
ttttcgatca gaaacttctc gacagacgtc gcggtgagtt caggcttttt catatctcat   9720
tgcccgggat ctgcggcacg ctgttgacgc tgttaagcgg gtcgctgcag ggtcgctcgg   9780
tgttcgaggc cacacgcgtc accttaatat gcgaagtgga cctgggaccg cgccgccccg   9840
actgcatctg cgtgttcgaa ttcgccaatg acaagacgct gggcggggtt tgtgtcatca   9900
tagaactaaa gacatgcaaa tatatttctt ccggggacac cgccagcaaa cgcgagcaac   9960
gggccacggg gatgaagcag ggcatggcgg ccgacgcgct gggctacgtc ttgctggcgt  10020
tcgcacaggc cggccagcgc gcggccggcc ggtaccacgc gttggccaca tatggcggcc  10080
gctcgcgatt aattaatcgc gatggccaca tatggagctc tctagagctt gtcgacagat  10140
ccccctcttc atttctttat gttttaaatg cactgacctc ccacattccc tttttagtaa  10200
aatattcaga aataatttaa atacatcatt gcaatgaaaa taatgttttt ttattaggca  10260
gaatccagat gctcaaggcc cttcataata tcccccagtt tagtagttgg acttagggaa  10320
caaaggaacc tttaatagaa attggacagc aagaaagcga gggggatctg gatcctccgg  10380
agggcccctt ctccctctaa cactctcccc tgttgaagct ctttgtgacg ggcgagctca  10440
ggccctgatg ggtgacttcg caggcgtaga cttttgtgttt ctcgtagtct gctttgctca  10500
gcgtcagggt gctgctgagg ctgtaggtgc tgtccttgct gtcctgctct gtgacactct  10560
cctgggagtt acccgattgg agggcgttat ccaccttcca ctgtactttg gcctctctgg  10620
```

```
gatagaagtt attcagcagg cacacaacag aggcagttcc agatttcaac tgctcatcag    10680
atggcgggaa gatgaagaca gatggtgcag ccacagttcg tctgatctcc accttggtcc    10740
ctccgccgaa agtgagcggg tgattatcat actgttgaca ataatatgtt gcaatatctt    10800
caggctgcag gctgctgatg gtgaaagtaa aatctgtccc agaaccactt ccactgaacc    10860
ttgatgggac tcttgtttcc aaattggaag cactgtagat caggagttta ggggcttttcc   10920 ctggtttctg ctgataccaa tttaaatagt tgataatgtc ctgactcgcc tggcaagtga    10980
tggtgactct gtctcccaca gatgcagaca gggaggatgg agactgggtc atctggatgt    11040
cacatctggc acctgagagc cagagcagca ggagcccag gagctgagca gggaccctca     11100
tgtccatgct gtgtcccggt tgggactgac tcctgcacag ggtgaattcc accacactgg    11160
actagtggat ccgagctcgg taccaagctt aagtttaaac gctagccagc ttgggtctcc    11220
ctatagtgag tcgtattaat ttcgataagc cagtaagcag tgggttctct agttagccag    11280
agagctctgc ttatatagac ctcccaccgt acacgcctac cgcccatttg cgtcaatggg    11340
gcggagttgt tacgacattt tggaaagtcc cgttgatttt ggtgccaaaa caaactccca    11400
ttgacgtcaa tggggtggag acttggaaat ccccgtgagt caaaccgcta tccacgccca    11460
ttgatgtact gccaaaaccg catcaccatg gtaatagcga tgactaatac gtagatgtac    11520
tgccaagtag gaaagtccca taggtcatg tactgggcat aatgccaggc gggccattta     11580
ccgtcattga cgtcaatagg gggcgtactt ggcatatgat acacttgatg tactgccaag    11640
tgggcagttt accgtaaata gtccacccat tgacgtcaat ggaaagtccc tattggcgtt    11700
actatgggaa catacgtcat tattgacgtc aatgggcggg ggtcgttggg cggtcagcca    11760
ggcgggccat ttaccgtaag ttatgtaacg cggaactcca tatatgggct atgaactaat    11820
gaccccgtaa ttgattacta ttaataacta gtcaataatc aatgtcaacg cgtatatctg    11880
gcccgtacat cggtaactag tcggaccggc ccgggccacc ggtgctcgaa gcttggatcg    11940
atccagacat gataagatac attgatgagt ttggacaaac cacaactaga atgcagtgaa    12000
aaaaatgctt tatttgtgaa atttgtgatg ctattgcttt atttgtaacc attataagct    12060
gcaataaaca agttaacaac aacaattgca ttcattttat gtttcaggtt cagggggagg    12120
tgtgggaggt ttttaaagc aagtaaaacc tctacaaatg tggtatggct gattatgatc     12180
tctagtcaag                                                          12190

<210> SEQ ID NO 7
<211> LENGTH: 12225
<212> TYPE: DNA
<213> ORGANISM: Artificial sequence
<220> FEATURE:
<223> OTHER INFORMATION: pAIGFRV3 plasmid

<400> SEQUENCE: 7
gcactataca tcaaatattc cttattaacc cctttacaaa ttaaaaagct aaaggtacac      60
aatttttgag catagttatt aatagcagac actctatgcc tgtgtggagt aagaaaaaac     120
agtatgttat gattataact gttatgccta cttataaagg ttacagaata ttttccata      180 attttcttgt atagcagtgc agcttttttc tttgtggtgt aaatagcaaa gcaagcaaga     240
gttctattac taaacacagc atgactcaaa aacttagca attctgaagg aaagtccttg      300
gggtcttcta cctttctctt cttttttgga ggagtagaat gttgagagtc agcagtagcc     360
tcatcatcac tagatggcat ttcttctgag caaaacaggt tttcctcatt aaaggcattc     420
caccactgct cccattcatc agttccatag gttggaatct aaaatacaca aacaattaga     480
```

```
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt ccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gttttttgcag aataatgttc tattagtcca gccactgtcc   1920
cctccttggt atggaaaatc tttccccaaa agtgcattcc tgttcctaga taaatataat   1980
catgtacctg ttgtttcatg tcgtctttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag ggggcatctg   2160
ttggtctgta gatgtaaggt cccctataag tcccctggttg ccaccacctg tctcctattt   2220
tgacaaaaac actctttttt cccttttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca gtttgcagc agagaatgaa tatgtctttg tctgatgggc   2700
tcatccgttt gtgcgcagac gggtcgtcct tggtgggaaa caacccctttg gctgcttctc   2760 ccctaggtgt aggacactct cgggagttca accatttctg cccaagctca gatctgagct   2820
ttaatgcggt agtttatcac agttaaattg ctaacgcagt caggcaccgt gtatgaaatc   2880
```

```
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgtcttccg cttcctcgct cactgactcg ctgcgctcgg    3060
tcgttcggct gcggcgagcg gtatcagctc actcaaaggc ggtaatacgg ttatccacag   3120
aatcagggga taacgcagga agaacatgt gagcaaaagg ccagcaaaag gccaggaacc    3180
gtaaaaaggc cgcgttgctg gcgttttcc ataggctccg ccccctgac gagcatcaca     3240 aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc aacccggta agacacgact    3540 tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg aaaaagagt tggtagctct tgatccggca    3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tccttttca atattattga agcatttatc    4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgct ggccggcctg tgcgaacgcc agcaagacgt agcccagcgc gtcggccgcc   5100
atgccctgct tcatccccgt ggcccgttgc tcgcgtttgc tggcggtgtc cccggaagaa   5160
atatatttgc atgtctttag ttctatgatg acacaaaccc cgcccagcgt cttgtcattg   5220
gcgaattcga acacgcagat gcagtcgggg cggcgcggtc ccaggtccac ttcgcatatt   5280
```

```
aaggtgacgc gtgtggcctc gaacaccgag cgaccctgca gcgacccgct taacagcgtc    5340
aacagcgtgc cgcagatccc gggcaatgag atatgaaaaa gcctgaactc accgcgacgt    5400
ctgtcgagaa gtttctgatc gaaaagttcg acagcgtctc cgacctgatg cagctctcgg    5460
agggcgaaga atctcgtgct ttcagcttcg atgtaggagg gcgtggatat gtcctgcggg    5520
taaatagctg cgccgatggt ttctacaaag atcgttatgt ttatcggcac tttgcatcgg    5580
ccgcgctccc gattccggaa gtgcttgaca ttggggaatt cagcgagagc ctgacctatt    5640
gcatctcccg ccgtgcacag ggtgtcacgt tgcaagacct gcctgaaacc gaactgcccg    5700
ctgttctgca gccggtcgcg gaggccatgg atgcgatcgc tgcggccgat cttagccaga    5760
cgagcgggtt cggcccattc ggaccgcaag gaatcggtca atacactaca tggcgtgatt    5820
tcatatgcgc gattgctgat ccccatgtgt atcactggca aactgtgatg gacgacaccg    5880
tcagtgcgtc cgtcgcgcag gctctcgatg agctgatgct ttgggccgag gactgccccg    5940
aagtccggca cctcgtgcac gcggatttcg gctccaacaa tgtcctgacg gacaatggcc    6000
gcataacagc ggtcattgac tggagcgagg cgatgttcgg ggattcccaa tacgaggtcg    6060
ccaacatctt cttctggagg ccgtggttgg cttgtatgga gcagcagacg cgctacttcg    6120
agcggaggca tccggagctt gcaggatcgc cgcggctccg ggcgtatatg ctccgcattg    6180
gtcttgacca actctatcag agcttggttg acggcaattt cgatgatgca gcttgggcgc    6240
agggtcgatg cgacgcaatc gtccgatccg gagccgggac tgtcgggcgt acacaaatcg    6300
cccgcagaag cgcggccgtc tggaccgatg gctgtgtaga agtactcgcc gatagtggaa    6360
accgacgccc cagcactcgt ccgagggcaa aggaataggg gagatggggg aggctaactg    6420
aaacacggaa ggagacaata ccggaaggaa cccgcgctat gacggcaata aaagacagaa    6480
ataaaacgca cgggtgttgg gtcgtttgtt cataaacgcg gggttcggtc ccagggctgg    6540
cactctgtcg ataccccacc gagacccccat tgggccaat acgcccgcgt tcttcctttt    6600
tccccacccc accccccaag ttcgggtgaa ggcccagggc tcgcagccaa cgtcggggcg    6660
gcaggccctg ccatagccac tggccccgtg ggttagggac ggggtccccc atggggaatg    6720
gtttatggtt cgtgggggtt attattttgg gcgttgcgtg gggtctggtc cacgactgga    6780
ctgagcagac agacccatgg tttttggatg gcctgggcat ggaccgcatg tactggcgcg    6840
acacgaacac cgggcgtctg tggctgccaa acaccccga ccccaaaaa ccaccgcgcg    6900 gatttctggc gccagtggc acaggccggc ctgtacatga tcaacgcgtg agctctctag    6960
agcttgtcga cagatccccc tcttcatttc tttatgtttt aaatgcactg acctcccaca    7020 ttccctttt agtaaaatat tcagaaataa tttaaataca tcattgcaat gaaaataaat    7080 gtttttatt aggcagaatc cagatgctca aggcccttca taatatcccc cagtttagta    7140
gttggactta gggaacaaag gaacctttaa tagaaattgg acagcaagaa agcgaggggg    7200
atctggatcc tccggacccg gggagcgggg gcttgccggc cctggcactc atttacccag    7260
agacagggag aggctcttct gtgtgtagtg gttgtgcaga gcctcatgca tcacggagca    7320
tgagaagaca ttcccctcct gccacctgct cttgtccacg gttagcctgc tgtagaggaa    7380
gaaggagccg tcggagtcca gcacgggagg cgtggtcttg tagttgttct ccggctgccc    7440
attgctctcc cactccacgg cgatgtcgct ggggtagaag ccttttgacca ggcaggtcag    7500 gctgacctgg ttcttggtca tctcctcctg ggatggggc agggtgtaca cctgtggctc    7560
tcggggctgc cctgtaggga cagaggttgg cacagcggtc actcccaggg cagagggtgg    7620
gccgagctga cctctgtcca tgtggccctc gcaccccgtg ggtcccacct ttggctttgg    7680
```

```
agatggtttt ctcgatggag gacgggaggc ctttgttgga gaccttgcac ttgtactcct    7740
tgccgttcag ccagtcctgg tgcaggacgg tgaggacgct gaccacacgg tacgtgctgt    7800
tgaactgctc ctcccgcggc tttgtcttgg cattatgcac ctccacgcca tccacgtacc    7860
agttgaactg gacctcgggg tcttcctggc tcacgtccac caccacgcac gtgacctcag    7920
gggtccggga gatcatgaga gtgtcctgg gttttggggg aacaggaag actgatggtc    7980 cccccaggaa ctcaggtgct gaggaagaga tggaggtgga tgcgtcagca cccggctggg    8040
gcctgtccct ggatgcaggc tactctaggg cacctgtccc gccttgagct ggagggcgag    8100
gcctgggttg gcttacctgg gcatgatggg catggggac catatttgga ctctgcagag    8160
agaagattgg gagttactca gatctgggag gagagaaggt gtctgagctg agggagtgga    8220
gagtttggcc tttggggtgg gcttaggtca ggggcagggt cctcccggat atggctcttg    8280
gcaggtctga gcgcagcacc tgcccctgta tgcgcagggc ctggggtagg gcatccagc     8340 ctgtggctgc ccggagcctg gtggaaaaat ccagaagacc ctctccctga gcatgagtgg    8400
ggtggtcaga ggcctccggg tgaggagaca gatgggcat gccttgctgc cctgggctgg    8460
ggctgcacag ccggggtgcg tccaggcagg agggctgagc ctggcttcca gcagacaccc    8520
tccctccctg tgctggcctc tcaccaactc tcttgtccac cttggtgttg ctgggcttgt    8580
gatctacgtt gcaggtgtag gtcttcgtgc ccaagctgct ggagggcacg gtcaccacgc    8640
tgctgaggga gtagagtcct gaggactgta ggacagccgg gaaggtgtgc acgccgctgg    8700
tcagggcgcc tgagttccac gacaccgtca ccggttcggg gaagtagtcc ttgaccaggc    8760
agcccagggc ggctgtgctc tcggaggtgc tcctggagca gggcgccagg gggaagacgg    8820
atgggccctt ggtggaagct gaggagacgg tgaccgtggt cccttggccc cagacgtcca    8880
taccgtagta gaagttcccc agtcttgcac agtaatacac agccatgtcc tcggctctca    8940
ggctgttcat ttgaagatac aaggagttct tggcattgtc tctggagatg gtgaatcggc    9000
ccttcacgga gtctgcatag tatgtggcac cacgagtatc aataactgat atccactcca    9060 gacctttcc tggagcctgg cgaacccagt gcatagcaaa gctactgaag gtgaatccag    9120
aggctgcaca ggagagtctc agggacccc caggatgtac caagcctccc ccagactgca    9180
ccagctgaac ctcacactgg acaccttta atatagcaac aaggaaaacc cagctcagcc    9240
caaactccat aagggcgaat tccaccacac tggactagtg gatccgagct cggtaccaag    9300
cttaagttta acgctagcc agcttgggtc tccctatagt gagtcgtatt aatttcgata    9360
agccagtaag cagtgggttc tctagttagc cagagagctc tgcttatata gacctcccac    9420
cgtacacgcc taccgcccat ttgcgtcaat ggggcggagt tgttacgaca ttttggaaag    9480
tcccgttgat tttggtgcca aaacaaactc ccattgacgt caatggggtg gagacttgga    9540 aatcccgtg agtcaaaccg ctatccacgc ccattgatgt actgccaaaa ccgcatcacc    9600
atggtaatag cgatgactaa tacgtagatg tactgccaag taggaaagtc ccataaggtc    9660
atgtactggg cataatgcca ggcgggccat ttaccgtcat tgacgtcaat aggggggcgta   9720 cttggcatat gatacacttg atgtactgcc aagtgggcag tttaccgtaa atagtccacc    9780
cattgacgtc aatggaaagt ccctattggc gttactatgg aacatacgt cattattgac     9840 gtcaatgggc ggggtcgtt gggcggtcag ccaggcgggc catttaccgt aagttatgta    9900
acgcggaact ccatatatgg gctatgaact aatgacccg taattgatta ctattaataa    9960
ctagtcaata atcaatgtca acgcgtatat ctggcccgta catcggtagc tgagggttta    10020
aacggcgcgc ggccggccgg taccacgcgt tggccacata tggcggccgc tcgcgattaa    10080
```

```
ttaatcgcga tggccacata tggagctctc tagagcttgt cgacagatcc ccctcttcat    10140
ttctttatgt tttaaatgca ctgacctccc acattcccct tttagtaaaa tattcagaaa    10200
taatttaaat acatcattgc aatgaaaata aatgtttttt attaggcaga atccagatgc    10260 tcaaggcct  tcataatatc ccccagttta gtagttggac ttagggaaca aaggaacctt    10320
taatagaaat tggacagcaa gaaagcgagg gggatctgga tcctccggag ggccccttct    10380
ccctctaaca ctctcccctg ttgaagctct ttgtgacggg cgagctcagg ccctgatggg    10440
tgacttcgca ggcgtagact ttgtgtttct cgtagtctgc tttgctcagc gtcagggtgc    10500
tgctgaggct gtaggtgctg tccttgctgt cctgctctgt gacactctcc tgggagttac    10560
ccgattggag ggcgttatcc accttccact gtactttggc ctctctggga tagaagttat    10620
tcagcaggca cacaacagag gcagttccag atttcaactg ctcatcagat ggcgggaaga    10680
tgaagacaga tggtgcagcc acagttcgtt tgatctccac cttggtccct ccgccgaaag    10740
tgtgaggtaa acgactactc tgatgacagt aatacgctgc agcatcttca gcttccaggc    10800
tattgatggt gagggtgaaa tctgtcccag atccactgcc actgaacctc gagggaccc    10860 ctgagaggga ctgggaagca tacttgatga ggagctttgg agactgatct ggtttctgct    10920
ggtaccagtg taagctacta ccaatgctct gactggcccg gcaggtgatg gtgactttct    10980
cctttggagt cacagactga aagtctggaa cctgagtcag cacaatttca ccctggagg     11040 ctggaaccca gagcagcaga aacccaatga gttgtgatgg cgacatcttc ctgccttgac    11100
ttgtcagttt tgctcatgcc cccgcgtact ctgcgttgtt accactgctt gcctatagt     11160 gagtcgtatt agaagggcga attccaccac actggactag tggatccgag ctcggtacca    11220
agcttaagtt taaacgctag ccagcttggg tctccctata gtgagtcgta ttaatttcga    11280
taagccagta agcagtgggt tctctagtta gccagagagc tctgcttata tagacctccc    11340
accgtacacg cctaccgccc atttgcgtca atggggcgga gttgttacga cattttggaa    11400
agtcccgttg atttggtgc  caaaacaaac tcccattgac gtcaatgggg tggagacttg    11460 gaaatcccg  tgagtcaaac cgctatccac gcccattgat gtactgccaa aaccgcatca    11520
ccatggtaat agcgatgact aatacgtaga tgtactgcca agtaggaaag tcccataagg    11580
tcatgtactg gcataatgc  caggcgggcc atttaccgtc attgacgtca ataggggcg     11640 tacttggcat atgatacact tgatgtactg ccaagtgggc agtttaccgt aaatagtcca    11700
cccattgacg tcaatggaaa gtccctattg gcgttactat gggaacatac gtcattattg    11760
acgtcaatgg gcgggggtcg ttgggcggtc agccaggcgg gccatttacc gtaagttatg    11820
taacgcggaa ctccatatat gggctatgaa ctaatgaccc cgtaattgat tactattaat    11880
aactagtcaa taatcaatgt caacgcgtat atctggcccg tacatcggta actagtcgga    11940
ccggcccggg ccaccggtgc tcgaagcttg atcgatcca  gacatgataa gatacattga    12000
tgagtttgga caaaccacaa ctagaatgca gtgaaaaaaa tgctttattt gtgaaatttg    12060
tgatgctatt gctttatttg taaccattat aagctgcaat aaacaagtta acaacaacaa    12120
ttgcattcat tttatgtttc aggttcaggg ggaggtgtgg gaggttttt  aaagcaagta    12180 aaacctctac aaatgtggta tggctgatta tgatctctag tcaag              12225
```

<210> SEQ ID NO 8
<211> LENGTH: 13079
<212> TYPE: DNA
<213> ORGANISM: Artificial sequence
<220> FEATURE:
<223> OTHER INFORMATION: pAIG1FR(-)IL2LS plasmid

```
<400> SEQUENCE: 8
gcactataca tcaaatattc cttattaacc cctttacaaa ttaaaaagct aaaggtacac      60
aattttttgag catagttatt aatagcagac actctatgcc tgtgtggagt aagaaaaaac    120
agtatgttat gattataact gttatgccta cttataaagg ttacagaata ttttttccata   180
attttcttgt atagcagtgc agcttttttcc tttgtggtgt aaatagcaaa gcaagcaaga    240
gttctattac taaacacagc atgactcaaa aaacttagca attctgaagg aaagtccttg    300
gggtcttcta cctttctctt ctttttttgga ggagtagaat gttgagagtc agcagtagcc   360
tcatcatcac tagatggcat ttcttctgag caaaacaggt tttcctcatt aaaggcattc    420
caccactgct cccattcatc agttccatag gttggaatct aaaatacaca acaattaga     480
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata   780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt ccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gttttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtcttttca cgaaaaggga gggatctata taacacttta tagccattga   2100
ctgtaaccca cctatcccaa tttaagtcat atcttcctgt atatggtaag ggggcatctg   2160
ttggtctgta gatgtaaggt cccctataag tccctggttg ccaccacctg tctcctattt   2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
```

```
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca agtttgcagc agagaatgaa tatgtctttg tctgatgggc    2700
tcatccgttt gtgcgcagac gggtcgtcct tggtgggaaa caaccccttg gctgcttctc    2760
ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag cataggctt     2940 ggttatgccg gtactgccgg gcctcttgcg ggatatcgtc cattccgaca gcatcgccag    3000
tcactatggg gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga agaacatgt gagcaaaagg ccagcaaaag gccaggaacc     3180
gtaaaaaggc cgcgttgctg gcgttttttcc ataggctccg cccccctgac gagcatcaca    3240
aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc caacccggta agacacgact    3540
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt ttgtttgcaa gcagcagatt acgcgcagaa    3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca acacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
```

```
ccagcgtttc tgggtgagca aaaacaggaa ggcaaaatgc cgcaaaaaag ggaataaggg      4800
cgacacggaa atgttgaata ctcatactct tcctttttca atattattga agcatttatc      4860
agggttattg tctcatgagc ggatacatat ttgaatgtat ttagaaaaat aaacaaatag      4920
gggttccgcg cacatttccc cgaaaagtgc cacctgacgt ctaagagacc attattatca      4980
tgacattaac ctataaaaat aggcgtatca cgaggccctt tcgtcttcaa gaattgtcta      5040
gaggcgcgct ggccggcctg tgcgaacgcc agcaagacgt agcccagcgc gtcggccgcc      5100
atgccctgct tcatccccgt ggcccgttgc tcgcgtttgc tggcggtgtc cccgaagaa       5160
atatatttgc atgtctttag ttctatgatg acacaaaccc cgcccagcgt cttgtcattg      5220
gcgaattcga acacgcagat gcagtcgggg cggcgcggtc ccaggtccac ttcgcatatt      5280
aaggtgacgc gtgtggcctc gaacaccgag cgaccctgca gcgacccgct taacagcgtc      5340
aacagcgtgc cgcagatccc gggcaatgag atatgaaaaa gcctgaactc accgcgacgt      5400
ctgtcgagaa gtttctgatc gaaaagttcg acagcgtctc cgacctgatg cagctctcgg      5460
agggcgaaga atctcgtgct ttcagcttcg atgtaggagg gcgtggatat gtcctgcggg      5520
taaatagctg cgccgatggt ttctacaaag atcgttatgt ttatcggcac tttgcatcgg      5580
ccgcgctccc gattccggaa gtgcttgaca ttggggaatt cagcgagagc ctgacctatt      5640
gcatctcccg ccgtgcacag ggtgtcacgt tgcaagacct gcctgaaacc gaactgcccg      5700
ctgttctgca gccggtcgcg gaggccatgg atgcgatcgc tgcggccgat cttagccaga      5760
cgagcgggtt cggcccattc ggaccgcaag gaatcggtca atacactaca tggcgtgatt      5820
tcatatgcgc gattgctgat ccccatgtgt atcactggca aactgtgatg gacgacaccg      5880
tcagtgcgtc cgtcgcgcag gctctcgatg agctgatgct ttgggccgag gactgccccg      5940
aagtccggca cctcgtgcac gcggatttcg gctccaacaa tgtcctgacg gacaatggcc      6000
gcataacagc ggtcattgac tggagcgagg cgatgttcgg ggattcccaa tacgaggtcg      6060
ccaacatctt cttctggagg ccgtggttgg cttgtatgga gcagcagacg cgctacttcg      6120
agcggaggca tccggagctt gcaggatcgc cgcggctccg ggcgtatatg ctccgcattg      6180
gtcttgacca actctatcag agcttggttg acggcaattt cgatgatgca gcttgggcgc      6240
agggtcgatg cgacgcaatc gtccgatccg gagccgggac tgtcgggcgt acacaaatcg      6300
cccgcagaag cgcggccgtc tggaccgatg gctgtgtaga agtactcgcc gatagtggaa      6360
accgacgccc cagcactcgt ccagggcaa aggaataggg gagatggggg aggctaactg       6420
aaacacggaa ggagacaata ccggaaggaa cccgcgctat gacggcaata aaaagacaga      6480
ataaaacgca cgggtgttgg gtcgtttgtt cataaacgcg gggttcggtc ccagggctgg      6540
cactctgtcg ataccccacc gagacccat tggggccaat acgcccgcgt ttcttccttt        6600
tccccacccc accccccaag ttcgggtgaa ggcccagggc tcgcagccaa cgtcggggcg      6660
gcaggccctg ccatagccac tggccccgtg ggttaggac ggggtccccc atggggaatg       6720
gtttatggtt cgtggggggtt attattttgg gcgttgcgtg gggtctggtc cacgactgga     6780
ctgagcagac agacccatgg ttttttggatg gcctgggcat ggaccgcatg tactggcgcg     6840
acacgaacac cggcgtctg tggctgccaa caccccccga ccccaaaaa ccaccgcgcg         6900
gatttctggc gcccagtggc acaggccggc ctgtacatga tcaacgcgtg agctctctag      6960
agcttgtcga cagatccccc tcttcatttc tttatgtttt aaatgcactg acctcccaca      7020
ttccctttt agtaaaatat tcagaaataa tttaaataca tcattgcaat gaaaataaat        7080
gttttttatt aggcagaatc cagatgctca aggcccttca taatatcccc cagtttagta      7140
```

```
gttggactta gggaacaaag gaacctttaa tagaaattgg acagcaagaa agcgaggggg     7200
atctggatcc tccggacccg tatctagaat catcgattca tttacccgga gacagggaga     7260
ggctcttctg cgtgtagtgg ttgtgcagag cctcatgcat cacggagcat gagaagacgt     7320 tccctgctg ccacctgctc ttgtccacgg tgagcttgct gtagaggaag aaggagccgt      7380
cggagtccag cacggaggc gtggtcttgt agttgttctc cggctgccca ttgctctccc      7440
actccacggc gatgtcgctg ggatagaagc cttgaccag gcaggtcagg ctgacctggt      7500
tcttggtcag ctcatcccgg gatgggggca gggtgtacac ctgtggttct cggggctgcc     7560
ctttggcttt ggagatggtt ttctcgatgg gggctgggag ggctttgttg gagaccttgc     7620
acttgtactc cttgccattc agccagtcct ggtgcaggac ggtgaggacg ctgaccacac     7680
ggtacgtgct gttgtactgc tcctcccgcg gctttgtctt ggcattatgc acctccacgc     7740
cgtccacgta ccagttgaac ttgacctcag ggtcttcgtg gctcacgtcc accaccacgc     7800
atgtgacctc aggggtccgg gagatcatga gggtgtcctt gggttttggg gggaagagga     7860
agactgacgg tccccccagg agttcaggtg ctgggcacgg tgggcatgtg tgagttttgt     7920
cacaagattt gggctcaact ttcttgtcca ccttggtgtt gctgggcttg tgattcacgt     7980
tgcagatgta ggtctgggtg cccaagctgc tggagggcac ggtcaccacg ctgctgaggg     8040
agtagagtcc tgaggactgt aggacagccg ggaaggtgtg cacgccgctg gtcagggcgc     8100
ctgagttcca cgacaccgtc accggttcgg ggaagtagtc cttgaccagg cagcccaggg     8160
ccgctgtgcc cccagaggtg ctcttggagg agggtgccag ggggaagacc gatgggccct     8220
tggtggaagc tgaggagacg gtgaccgtgg tcccttggcc ccagacgtcc ataccgtagt     8280
agaagttccc cagtcttgca cagtaataca cagcagtgtc ctcggctctc aggctgttca     8340
tttgaagata caaggagttc ttggcattgt ctctggagat ggtgaatcgg cccttcacgg     8400
agtctgcata gtatgtggca ccacgagtat caataactga tatccactcc agccttttc      8460 ctggagcctg gcgaacccag tgcatagcaa agctactgaa ggtgaatcca gaggctgcac     8520
aggagagtct cagggacccc ccaggctta ccaagcctcc cccagactgc accagctgaa      8580
cctcacactg gacaccttt aatatagcaa caaggaaaac ccagctcagc ccaaactcca      8640
taagggcgaa ttccaccaca ctggactagt ggatccgagc tcggtaccaa gcttaagttt     8700
aaacgctagc cagcttgggt ctccctatag tgagtcgtat taatttcgat aagccagtaa     8760 gcagtggggtt ctctagttag ccagagagct ctgcttatat agacctccca ccgtacacgc    8820
ctaccgccca tttgcgtcaa tggggcggag ttgttacgac attttggaaa gtcccgttga     8880
ttttggtgcc aaaacaaact cccattgacg tcaatgggt ggagacttgg aaatccccgt      8940
gagtcaaacc gctatccacg cccattgatg tactgccaaa accgcatcac catggtaata     9000
gcgatgacta atacgtagat gtactgccaa gtaggaaagt cccataaggt catgtactgg     9060
gcataatgcc aggcgggcca tttaccgtca ttgacgtcaa taggggggcgt acttggcata     9120 tgatacactt gatgtactgc caagtgggca gtttaccgta aatagtccac ccattgacgt     9180
caatggaaag tccctattgg cgttactatg gaacatacg tcattattga cgtcaatggg      9240 cggggtcgt tggcggtca gccaggcggg ccatttaccg taagttatgt aacgcggaac       9300
tccatatatg ggctatgaac taatgacccc gtaattgatt actattaata actagtcaat     9360
aatcaatgtc aacgcgtata tctggcccgt acatcggtag ctgagggttt aaacggcgcg     9420
cggccggccg gtaccacgcg ttggccacat atggcggccg ctcgcgatta attaatcgcg     9480
atggccacat atggagctct ctagagcttg tcgacagatc cccctcttca tttctttatg     9540
```

```
ttttaaatgc actgacctcc cacattccct ttttagtaaa atattcagaa ataatttaaa   9600
tacatcattg caatgaaaat aaatgttttt tattaggcag aatccagatg ctcaaggccc   9660
ttcataatat cccccagttt agtagttgga cttaggaac aaaggaacct ttaatagaaa    9720
ttggacagca agaaagcgag ggggatctgg atcctccgga gggcccctgc aggaattcga   9780
tggccgctag attgttcttc tactcttcct ctgtctccgc tgccaggtga gcccactcag   9840
gaggaggacg ctgatcagca ggaaaacaca gccggccact gctacctggt actctgttgt   9900
aaatatggac gtctccatgg ttgcagccat ttctgtctgt atttgaaaat ctgttgttgt   9960
gacgaggcag gaagtctcac tctcaggacg gccttcgggg cttgcctgag gcttctcttc  10020
acctggaaac tgactggtct ccatttcacc tgtgcatatg agctggggct gggtccacct  10080
tgtcttcccg tgggtcattt tgcagacgct ctcagcagga cctctgtgta gagccctgta  10140
tccctggacg cactgataat aaaccatctg ccccaccacg aaatgataaa ttctctctgt  10200
ggcttcattt tcccatggtg gaggttccct gcagtgacct ggaaggctcg cttggtccac  10260
tggctgcatt ggactttgca tttctgtggt tttccttcct ttctgttctt caggttgagg  10320
tgtcacttgt ttcgttgtgt tccgagtggc agagcttgtg cattgacatt ggttgtccca  10380
ggacgagtgg ctagagtttc ctgtacagag catatagagt gacccgcttt ttattctgcg  10440
gaaacctctc ttgcattcac agttcaacat ggttccttcc ttgtaggcca tggctttgaa  10500
tgtggcgtgt gggatctctg gcgggtcatc gtcacagagc tctgcctggc agccaggcac  10560
catgatgaac gtgagcagtc cccacatcag caggtatgaa tccatggtgg cggcaaccgg  10620
ttatcatcgt gttttcaaa ggaaaaccac gtccccgtgg ttcgggggc ctagacgttt    10680
tttaacctcg actaaacaca tgtaaagcat gtgcaccgag gccccagatc agatcccata  10740
caatggggta ccttctgggc atccttcagc cccttgttga atacgcttga ggagagccat  10800
ttgactcttt ccacaactat ccaactcaca acgtggcact ggggttgtgc cgcctttgca  10860
ggtgtatctt atacacgtgg cttttggccg cagaggcacc tgtcgccagg tgggggttc   10920
cgctgcctgc aaagggtcgc tacagacgtt gtttgtcttc aagaagcttc agaggaact   10980
gcttccttca cgacattcaa cagaccttgc attccttgg cgagagggga aagacccta    11040
ggaatgctcg tcaagaagac agggccaggt ttccgggccc tcacattgcc aaaagacggc  11100
aatatggtgg aaaataacat atagacaaac gcacaccggc cttattccaa gcggcttcgg  11160
ccagtaacgt taggggggg ggaggggag gggcgctcga gactagccgg agggcccctt    11220
ctccctctaa cactctcccc tgttgaagct ctttgtgacg ggcgagctca ggccctgatg  11280
ggtgacttcg caggcgtaga cttttgtgttt ctcgtagtct gctttgctca gcgtcagggt 11340
gctgctgagg ctgtaggtgc tgtccttgct gtcctgctct gtgacactct cctgggagtt  11400
acccgattgg agggcgttat ccaccttcca ctgtactttg gcctctctgg atagaagtt   11460
attcagcagg cacacaacag aggcagttcc agatttcaac tgctcatcag atggcgggaa  11520
gatgaagaca gatggtgcag ccacagttcg tttgatctcc accttggtcc ctccgccgaa  11580
agtgtgaggt aaacgactac tctgatgaca gtaaatacgct gcagcatctt cagcttccag  11640
gctattgatg gtgagggtga aatctgtccc agatccactg ccactgaacc tcgagggac   11700
ccctgagagg gactgggaag catacttgat gaggagcttt ggagactgat ctggtttctg  11760
ctggtaccag tgtaagctac taccaatgct ctgactggcc cggcaggtga tggtgacttt  11820
ctcctttgga gtcacagact gaaagtctgg aacctgagtc agcacaattt caccccctgga 11880
ggctggaacc cagagcagca gaaacccaat gagttgtgat ggcgacatct tcctgccttg  11940
```

-continued

```
acttgtcagt tttgctcatg cccccgcgta ctctgcgttg ttaccactgc ttgccctata    12000
gtgagtcgta ttagaagggc gaattccacc acactggact agtggatccg agctcggtac    12060
caagcttaag tttaaacgct agccagcttg ggtctcccta tagtgagtcg tattaatttc    12120
gataagccag taagcagtgg gttctctagt tagccagaga gctctgctta tatagacctc    12180
ccaccgtaca cgcctaccgc ccatttgcgt caatggggcg gagttgttac gacattttgg    12240
aaagtcccgt tgattttggt gccaaaacaa actcccattg acgtcaatgg ggtggagact    12300
tggaaatccc cgtgagtcaa accgctatcc acgcccattg atgtactgcc aaaaccgcat    12360
caccatggta atagcgatga ctaatacgta gatgtactgc caagtaggaa agtcccataa    12420
ggtcatgtac tgggcataat gccaggcggg ccatttaccg tcattgacgt caatagggggg    12480 cgtacttggc atatgataca cttgatgtac tgccaagtgg gcagtttacc gtaaatagtc    12540
cacccattga cgtcaatgga aagtccctat tggcgttact atgggaacat acgtcattat    12600
tgacgtcaat gggcgggggt cgttgggcgg tcagccaggc gggccattta ccgtaagtta    12660
tgtaacgcgg aactccatat atgggctatg aactaatgac cccgtaattg attactatta    12720
ataactagtc aataatcaat gtcaacgcgt atatctggcc cgtacatcgg taactagtcg    12780
daccgccgcg gactagtgcc cgggccaccg gtgctcgaag cttggatcga tccagacatg    12840
ataagataca ttgatgagtt tggacaaacc acaactagaa tgcagtgaaa aaaatgcttt    12900
atttgtgaaa tttgtgatgc tattgcttta tttgtaacca ttataagctg caataaacaa    12960
gttaacaaca acaattgcat tcattttatg tttcaggttc agggggaggt gtgggaggtt    13020
ttttaaagca agtaaaacct ctacaaatgt ggtatggctg attatgatct ctagtcaag     13079
```

<210> SEQ ID NO 9
<211> LENGTH: 11520
<212> TYPE: DNA
<213> ORGANISM: Artificial sequence
<220> FEATURE:
<223> OTHER INFORMATION: pAIL10V3 plasmid

<400> SEQUENCE: 9

```
gcactataca tcaaatattc cttattaacc cctttacaaa ttaaaaagct aaaggtacac      60 aattttttgag catagttatt aatagcagac actctatgcc tgtgtggagt aagaaaaaac    120
agtatgttat gattataact gttatgccta cttataaagg ttacagaata ttttttccata   180 attttcttgt atagcagtgc agcttttttcc tttgtggtgt aaatagcaaa gcaagcaaga   240
gttctattac taaacacagc atgactcaaa aaacttagca attctgaagg aaagtccttg    300
gggtcttcta ccttctctt ctttttttgga ggagtagaat gttgagagtc agcagtagcc    360
tcatcatcac tagatggcat ttcttctgag caaaacaggt tttcctcatt aaaggcattc    420
caccactgct cccattcatc agttcccatag gttggaatct aaaatacaca acaattaga    480 atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
```

```
atcatccaaa cttttggcaa gaaaatgagc tcctcgtggt ggttctttga gttctctact    1020
gagaactata ttaattctgt cctttaaagg tcgattcttc tcaggaatgg agaaccaggt    1080
tttcctaccc ataatcacca gattctgttt accttccact gaagaggttg tggtcattct    1140
ttggaagtac ttgaactcgt tcctgagcgg aggccagggt aggtctccgt tcttgccaat    1200
ccccatattt tgggacacgg cgacgatgca gttcaatggt cgaaccatga tggcagcggg    1260
gataaaatcc taccagcctt cacgctagga ttgccgtcaa gtttggcgcg aaatcgcagc    1320
cctgagctgt cccccccccc aagctcagat ctgagcttgg tccctatggt gagtccgttc    1380
cgctcttgtg atgatagcca gacaagaaag agacaataca agacaaacac caaatagtag    1440
aaatagagac aagggtcact tatccgaggg tccctgttcg ggcgccagct gccgcagtcg    1500
gccgacctga gggtcgccgg ggtctgcggg gggaccctct ggaaagtgaa ggataagtga    1560
cgagcggaga cgggatggcg aacagacaca aacacacaag aggtgaatgt taggactgtt    1620
gcaagtttac tcaaaaaatc agcactcttt tatatcttgg tttacataag catttacata    1680
agatttggat aaattccaaa gaacatagg aaaatagaac actcagagct cagatcagaa    1740
cctttgatac caaaccaagt caggaaacca cttgtctcac atcctcgttt taagaacagt    1800
ttgtaaccaa aaacttactt aagccctggg aaccgcaagg ttgggccaat aaaggctatt    1860
cataataact catgccatga gttttttgcag aataatgttc tattagtcca gccactgtcc    1920
cctccttggt atggaaaatc tttccccaaa agtgcattcc tgttcctaga taaatataat    1980
catgtacctg ttgtttcatg tcgtcttttt cttcttgaga caacatacac caaggaggtc    2040
tagctctggc gagtctttca cgaaaaggga gggatctata taacacttta tagccattga    2100
ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actctttttt ccctttttta cttctaggcc tgtggtcaat agtccttgca    2280
cctgttcttc aattgaggtt gagcgtctct ttctattttc tattcccatt tctaacttct    2340
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca gtttgcagc agagaatgaa tatgtctttg tctgatgggc    2700
tcatccgttt gtgcgcagac gggtcgtcct tggtgggaaa caaccccttg gctgcttctc    2760
ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag cataggctt    2940 ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga agaacatgt gagcaaaagg ccagcaaaag gccaggaacc    3180
gtaaaaaggc cgcgttgctg gcgttttttcc ataggctccg ccccctgac gagcatcaca    3240 aaaatcgacg ctcaagtcag aggtggcgaa acccgacagg actataaaga taccaggcgt    3300 ttcccctgg aagctccctc gtgcgctctc ctgttccgac cctgccgctt accggatacc    3360
```

```
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg aaaaagagt tggtagctct tgatccggca    3720
aacaaaccac cgctggtagc ggtggttttt ttgtttgcaa gcagcagatt acgcgcagaa   3780 aaaaggatc tcaagaagat cctttgatct tttctacggg gtctgacgct cagtggaacg    3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca cacgggata taccgcgcc acatagcaga actttaaaag     4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgct ggccggcctg tgcgaacgcc agcaagacgt agcccagcgc gtcggccgcc   5100
atgccctgct tcatccccgt ggcccgttgc tcgcgtttgc tggcggtgtc cccggaagaa   5160
atatatttgc atgtctttag ttctatgatg acacaaaccc cgcccagcgt cttgtcattg   5220
gcgaattcga acacgcagat gcagtcgggg cggcgcggtc ccaggtccac ttcgcatatt   5280
aaggtgacgc gtgtggcctc gaacaccgag cgaccctgca gcgacccgct taacagcgtc   5340
aacagcgtgc cgcagatccc gggcaatgag atatgaaaaa gcctgaactc accgcgacgt   5400
ctgtcgagaa gtttctgatc gaaaagttcg acagcgtctc cgacctgatg cagctctcgg   5460
agggcgaaga atctcgtgct ttcagcttcg atgtaggagg gcgtggatat gtcctgcggg   5520
taaatagctg cgccgatggt ttctacaaag atcgttatgt ttatcggcac tttgcatcgg   5580
ccgcgctccc gattccggaa gtgcttgaca ttggggaatt cagcgagagc ctgacctatt   5640
gcatctcccg ccgtgcacag ggtgtcacgt tgcaagacct gcctgaaacc gaactgcccg   5700
ctgttctgca gccggtcgcg gaggccatgg atgcgatcgc tgcggccgat cttagccaga   5760
```

-continued

```
cgagcgggtt cggcccattc ggaccgcaag gaatcggtca atacactaca tggcgtgatt    5820
tcatatgcgc gattgctgat ccccatgtgt atcactggca aactgtgatg gacgacaccg    5880
tcagtgcgtc cgtcgcgcag gctctcgatg agctgatgct ttgggccgag gactgccccg    5940
aagtccggca cctcgtgcac gcggatttcg gctccaacaa tgtcctgacg gacaatggcc    6000
gcataacagc ggtcattgac tggagcgagg cgatgttcgg ggattcccaa tacgaggtcg    6060
ccaacatctt cttctggagg ccgtggttgg cttgtatgga gcagcagacg cgctacttcg    6120
agcggaggca tccggagctt gcaggatcgc cgcggctccg ggcgtatatg ctccgcattg    6180
gtcttgacca actctatcag agcttggttg acggcaattt cgatgatgca gcttgggcgc    6240
agggtcgatg cgacgcaatc gtccgatccg gagccgggac tgtcgggcgt acacaaatcg    6300
cccgcagaag cgcggccgtc tggaccgatg gctgtgtaga agtactcgcc gatagtggaa    6360
accgacgccc cagcactcgt ccagggcaa aggaataggg gagatggggg aggctaactg    6420
aaacacggaa ggagacaata ccggaaggaa cccgcgctat gacggcaata aaaagacaga    6480
ataaaacgca cgggtgttgg gtcgtttgtt cataaacgcg gggttcggtc ccagggctgg    6540
cactctgtcg atacccccacc gagacccat tggggccaat acgcccgcgt tcttcctttt    6600
tccccacccc accccccaag ttcgggtgaa ggcccagggc tcgcagccaa cgtcggggcg    6660
gcaggccctg ccatagccac tggccccgtg ggttagggac ggggtccccc atggggaatg    6720
gtttatggtt cgtgggggtt attattttgg gcgttgcgtg gggtctggtc cacgactgga    6780
ctgagcagac agacccatgg ttttttggatg gcctgggcat ggaccgcatg tactggcgcg    6840
acacgaacac cgggcgtctg tggctgccaa acaccccccga cccccaaaaa ccaccgcgcg    6900
gatttctggc gcccagtggc acaggccggc ctgtacatga tcaacgcgtg agctctctag    6960
agcttgtcga cagatccccc tcttcatttc tttatgtttt aaatgcactg acctcccaca    7020
ttcccttttt agtaaaatat tcagaaataa tttaaataca tcattgcaat gaaaataaat    7080
gttttttatt aggcagaatc cagatgctca aggcccttca taatatcccc cagtttagta    7140
gttggactta gggaacaaag gaaccttaa tagaaattgg acagcaagaa agcgaggggg    7200
atctggatcc tccggacccg tatctagaat catcgattca tttacccgga gacagggaga    7260
ggctcttctg cgtgtagtgg ttgtgcagag cctcatgcat cacggagcat gagaagacgt    7320
tcccctgctg ccacctgctc ttgtccacgg tgagcttgct gtagaggaag aaggagccgt    7380
cggagtccag cacgggaggc gtggtcttgt agttgttctc cggctgccca ttgctctccc    7440
actccacggc gatgtcgctg ggatagaagc ctttgaccag gcaggtcagg ctgacctggt    7500
tcttggtcag ctcatcccgg gatgggggca gggtgtacac ctgtggttct cggggctgcc    7560
cttggctttt ggagatggtt ttctcgatgg gggctgggag ggctttgttg gagaccttgc    7620
acttgtactc cttgccattc agccagtcct ggtgcaggac ggtgaggacg ctgaccacac    7680
ggtacgtgct gttgtactgc tcctcccgcg gctttgtctt ggcattatgc acctccacgc    7740
cgtccacgta ccagttgaac ttgacctcag ggtcttcgtg gctcacgtcc accaccacgc    7800
atgtgacctc aggggtccgg gagatcatga gggtgtcctt gggttttggg gggaagagga    7860
agactgacgg tcccccagg agttcaggtg ctgggcacgg tgggcatgtg tgagttttgt    7920
cacaagattt gggctcaact ttcttgtcca ccttggtgtt gctgggcttg tgattcacgt    7980
tgcagatgta ggtctgggtg cccaagctgc tggagggcac ggtcaccacg ctgctgaggg    8040
agtagagtcc tgaggactgt aggacagccg ggaaggtgtg cacgccgctg gtcagggcgc    8100
ctgagttcca cgacaccgtc accggttcgg ggaagtagtc cttgaccagg cagcccaggg    8160
```

-continued

```
ccgctgtgcc cccagaggtg ctcttggagg agggtgccag ggggaagacc gatgggccct   8220
tggtgctagc cgacgagacg gtgaccaggg tgccttggcc ccagtaatca agccagacgc   8280
taaagcctcg atgtctcgca cagtaataca cagccgtgtc ctcagctctc aggctgttca   8340
tttgcagata cagcgtgttc ttggaattgt ctctggagat ggtgaagcgg ccgcgcacgg   8400
agtcgcgata gtaagtgtag gtagcatcaa gagtaatgct tgccacccac tccagcccct   8460
tgcctggagc ctggcggacc caggccatat gatagtcact gaaagtgaat ccagaggctg   8520
cacaggagag tctcagggac ctcccaggct ggaccacgcc tccccagac tccaccagct   8580 gcacctggga taggacacag cttgggaatg tcaccaggca gaagagcagc cccaagacag   8640
ccatgttaac tttctggtac caagcttaag tttaaacgct agccagcttg ggtctccta   8700 tagtgagtcg tattaatttc gataagccag taagcagtgg gttctctagt tagccagaga   8760
gctctgctta tatagacctc ccaccgtaca cgcctaccgc ccatttgcgt caatggggcg   8820
gagttgttac gacattttgg aaagtcccgt tgattttggt gccaaaacaa actcccattg   8880
acgtcaatgg ggtggagact tggaaatccc cgtgagtcaa accgctatcc acgcccattg   8940
atgtactgcc aaaaccgcat caccatggta atagcgatga ctaatacgta gatgtactgc   9000
caagtaggaa agtcccataa ggtcatgtac tgggcataat gccaggcggg ccatttaccg   9060
tcattgacgt caataggggg cgtacttggc atatgataca cttgatgtac tgccaagtgg   9120
gcagtttacc gtaaatagtc cacccattga cgtcaatgga aagtccctat tggcgttact   9180
atgggaacat acgtcattat tgacgtcaat gggcgggggt cgttgggcgg tcagccaggc   9240
gggccattta ccgtaagtta tgtaacgcgg aactccatat atgggctatg aactaatgac   9300
cccgtaattg attactatta ataactagtc aataatcaat gtcaacgcgt atatctggcc   9360
cgtacatcgg tagctgaggg tttaaacggc gcgcggccgg ccggtaccac gcgttggcca   9420
catatggcgg ccgctcgcga ttaattaatc gcgatggcca catatggagc tctctagagc   9480
ttgtcgacag atccccctct tcatttcttt atgttttaaa tgcactgacc tcccacattc   9540 ccttttagt aaaatattca gaaataattt aaatacatca ttgcaatgaa ataaatgtt   9600 ttttattagg cagaatccag atgctcaagg cccttcataa tatcccccag tttagtagtt   9660 ggacttaggaa acaaaggaa cctttaatag aaattggaca gcaagaaagc gaggggatc   9720 tggatcctcc ggagggccct ggatcctcct acgtatctag aatcatcgat taacactctc   9780
ccctgttgaa gctctttgtg acgggcgagc tcaggccctg atgggtgact tcgcaggcgt   9840
agactttgtg tttctcgtag tctgctttgc tcagcgtcag ggtgctgctg aggctgtagg   9900
tgctgtcctt gctgtcctgc tctgtgacac tctcctggga gttaccgat tggagggcgt   9960 tatccacctt ccactgtact ttggcctctc tgggatagaa gttattcagc aggcacacaa  10020
cagaggcagt tccagatttc aactgctcat cagatggcgg gaagatgaag acagatggtg  10080
cagccaccgt acgtttcagt tccagcttgg tcccaggtcc aaacgtgtac ccgctataat  10140
actggtgaca gtagtaagtt gcaaaatctt caggttgcag actgctgatg gtgagagtga  10200
aatctgtccc agatccactg ccactgaacc ttgatggac ccccgcttgc aaagggcttg  10260
cattatagat caggagctta ggggcttttc ctggtttctg ctgataccag gccaagttct  10320
caaaaatgtt ctgacttgtc ttgcaagtga tggtgactct gtctcctaca gatgcagaca  10380
gggaggatgg agactgggtc atctggatgt cacatctcat ggctgggagg aagagcacca  10440
aaagccctaa aagttgaact ggagccatct cgagaattcc accacactgg actagtggat  10500
ccgagctcgg taccaagctt aagtttaaac gctagccagc ttgggtctcc ctatagtgag  10560
```

```
tcgtattaat ttcgataagc cagtaagcag tgggttctct agttagccag agagctctgc    10620
ttatatagac ctcccaccgt acacgcctac cgcccatttg cgtcaatggg cggagttgt     10680 tacgacattt tggaaagtcc cgttgatttt ggtgccaaaa caaactccca ttgacgtcaa    10740
tggggtggag acttggaaat ccccgtgagt caaaccgcta ccacgccca ttgatgtact     10800 gccaaaaccg catcaccatg gtaatagcga tgactaatac gtagatgtac tgccaagtag    10860
gaaagtccca taaggtcatg tactgggcat aatgccaggc gggccattta ccgtcattga    10920
cgtcaatagg gggcgtactt ggcatatgat acacttgatg tactgccaag tgggcagttt    10980
accgtaaata gtccacccat tgacgtcaat ggaaagtccc tattggcgtt actatgggaa    11040
catacgtcat tattgacgtc aatgggcggg ggtcgttggg cggtcagcca ggcgggccat    11100
ttaccgtaag ttatgtaacg cggaactcca tatatgggct atgaactaat gaccccgtaa    11160
ttgattacta ttaataacta gtcaataatc aatgtcaacg cgtatatctg gcccgtacat    11220
cggtaactag tcggaccggc ccgggccacc ggtgctcgaa gcttggatcg atccagacat    11280
gataagatac attgatgagt ttggacaaac cacaactaga atgcagtgaa aaaaatgctt    11340
tatttgtgaa atttgtgatg ctattgcttt atttgtaacc attataagct gcaataaaca    11400
agttaacaac aacaattgca ttcattttat gtttcaggtt cagggggagg tgtgggaggt    11460
tttttaaagc aagtaaaacc tctacaaatg tggtatggct gattatgatc tctagtcaag    11520
```

<210> SEQ ID NO 10
<211> LENGTH: 155
<212> TYPE: DNA
<213> ORGANISM: Artificial sequence
<220> FEATURE:
<223> OTHER INFORMATION: multiple cloning site

<400> SEQUENCE: 10

```
aaatctagag gcgcgccgtt taaaccctca gctgatcatc cggatgtaca gcgcgcggcc     60
ggccggtacc acgcgttggc cacatatggc ggccgctcgc gattaattaa cggaccgccg    120
cggactagtg cccgggccac cggtgctcga gaaaa                                155
```

<210> SEQ ID NO 11
<211> LENGTH: 160
<212> TYPE: DNA
<213> ORGANISM: Artificial sequence
<220> FEATURE:
<223> OTHER INFORMATION: multiple cloning site

<400> SEQUENCE: 11

```
gggggcgcgc cgtttaaacc ctcagctacg taaagcttgg taccctcgag gtcgacatcg     60
atgatatcga attcctgcag gggcccccg gtccggagg atccgcggcc gctctagaga      120
gctcacgcgt tgatcatgta caggccggcc agcgcgcccc                           160
```

<210> SEQ ID NO 12
<211> LENGTH: 166
<212> TYPE: DNA
<213> ORGANISM: Artificial sequence
<220> FEATURE:
<223> OTHER INFORMATION: multiple cloning site

<400> SEQUENCE: 12

```
gggggcgcgc caccggtggc ccgggccggt ccgactagtt acgtaaagct tggtaccctc     60
gaggtcgaca tcgatgatat cgaattcctg caggggccct ccgaggatc cgcggccgct    120 ctagagagct ccatatgtgg ccatcgcgat taattaagcg cgcccc                   166
```

<210> SEQ ID NO 13
<211> LENGTH: 6078
<212> TYPE: DNA
<213> ORGANISM: Artificial sequence
<220> FEATURE:
<223> OTHER INFORMATION: pSRXBLS plasmid

<400> SEQUENCE: 13

| | | | | | |
|---|---|---|---|---|---|
| gcactataca | tcaaatattc | cttattaacc | cctttacaaa | ttaaaaagct | aaaggtacac | 60 |
| aattttttgag | catagttatt | aatagcagac | actctatgcc | tgtgtggagt | aagaaaaaac | 120 |
| agtatgttat | gattataact | gttatgccta | cttataaagg | ttacagaata | ttttttccata | 180 |
| attttcttgt | atagcagtgc | agcttttttcc | tttgtggtgt | aaatagcaaa | gcaagcaaga | 240 |
| gttctattac | taaacacagc | atgactcaaa | aaacttagca | attctgaagg | aaagtccttg | 300 |
| gggtcttcta | cctttctctt | cttttttgga | ggagtagaat | gttgagagtc | agcagtagcc | 360 |
| tcatcatcac | tagatggcat | tcttctgag | caaaacaggt | tttcctcatt | aaaggcattc | 420 |
| caccactgct | cccattcatc | agttccatag | gttggaatct | aaaatacaca | acaattaga | 480 |
| atcagtagtt | taacacatta | tacacttaaa | aattttatat | ttaccttaga | gctttaaatc | 540 |
| tctgtaggta | gtttgtccaa | ttatgtcaca | ccacagaagt | aaggttcctt | cacaaagatc | 600 |
| gatctaaagc | cagcaaaagt | cccatggtct | tataaaaatg | catagcttta | ggagggagc | 660 |
| agagaacttg | aaagcatctt | cctgttagtc | tttcttctcg | tagacttcaa | acttatactt | 720 |
| gatgcctttt | tcctcctgga | cctcagagag | gacgcctggg | tattctggga | gaagttttata | 780 |
| tttccccaaa | tcaatttctg | ggaaaaacgt | gtcactttca | aattcctgca | tgatccttgt | 840 |
| cacaaagagt | ctgaggtggc | ctggttgatt | catggcttcc | tggtaaacag | aactgcctcc | 900 |
| gactatccaa | accatgtcta | ctttacttgc | caattccggt | tgttcaataa | gtcttaaggc | 960 |
| atcatccaaa | cttttggcaa | gaaaatgagc | tcctcgtggt | ggttctttga | gttctctact | 1020 |
| gagaactata | ttaattctgt | cctttaaagg | tcgattcttc | tcaggaatgg | agaaccaggt | 1080 |
| tttcctaccc | ataatcacca | gattctgttt | accttccact | gaagaggttg | tggtcattct | 1140 |
| ttggaagtac | ttgaactcgt | tcctgagcgg | aggccagggt | aggtctccgt | tcttgccaat | 1200 |
| ccccatattt | tgggacacgg | cgacgatgca | gttcaatggt | cgaaccatga | tggcagcggg | 1260 |
| gataaaatcc | taccagcctt | cacgctagga | ttgccgtcaa | gtttggcgcg | aaatcgcagc | 1320 |
| cctgagctgt | cccccccccc | aagctcagat | ctgagcttgg | tccctatggt | gagtccgttc | 1380 |
| cgctcttgtg | atgatagcca | gacaagaaag | agacaataca | agacaaacac | caaatagtag | 1440 |
| aaatagagac | aagggtcact | tatccgaggg | tccctgttcg | ggcgccagct | gccgcagtcg | 1500 |
| gccgacctga | gggtcgccgg | ggtctgcggg | gggaccctct | ggaaagtgaa | ggataagtga | 1560 |
| cgagcggaga | cgggatggcg | aacagacaca | aacacacaag | aggtgaatgt | taggactgtt | 1620 |
| gcaagtttac | tcaaaaaatc | agcactcttt | tatatcttgg | tttacataag | catttacata | 1680 |
| agatttggat | aaaattccaaa | agaacatagg | aaaatagaac | actcagagct | cagatcagaa | 1740 |
| cctttgatac | caaaccaagt | caggaaacca | cttgtctcac | atcctcgttt | taagaacagt | 1800 |
| ttgtaaccaa | aaacttactt | aagccctggg | aaccgcaagg | ttgggccaat | aaaggctatt | 1860 |
| cataataact | catgccatga | gttttgcag | aataatgttc | tattagtcca | gccactgtcc | 1920 |
| cctccttggt | atggaaaatc | tttccccaaa | agtgcattcc | tgttcctaga | taaatataat | 1980 |
| catgtacctt | tgtttcatg | tcgtcttttt | cttcttgaga | caacatacac | caaggaggtc | 2040 |
| tagctctggc | gagtctttca | cgaaaaggga | gggatctata | taacactta | tagccattga | 2100 |

```
ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actcttttt ccctttttta cttctaggcc tgtggtcaat agtccttgca    2280
cctgttcttc aattgaggtt gagcgtctct ttctattttc tattcccatt tctaacttct    2340
gaatttgagt aaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca gtttgcagc agagaatgaa tatgtctttg tctgatgggc    2700
tcatccgttt gtgcgcagac gggtcgtcct tggtgggaaa caacccttg gctgcttctc    2760 ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcacctg gatgctgtag cataggctt    2940 ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga agaacatgt gagcaaaagg ccagcaaaag gccaggaacc    3180
gtaaaaaggc cgcgttgctg gcgttttttcc ataggctccg ccccctgac gagcatcaca    3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc aacccggta agacacgact    3540 tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt ttgtttgcaa gcagcagatt acgcgcagaa    3780
aaaaaggatc tcaagaagat cctttgatct ttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
```

```
tttctgtgac tggtgagtac tcaaccaagt cattctgaga atagtgtatg cggcgaccga    4560
gttgctcttg cccggcgtca acacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
cgacacggaa atgttgaata ctcatactct tcctttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgcc gtttaaaccc tcagctgatc atccggatgt acagcgcgcg gccggccggt    5100
accacgcgtt ggccacatat ggcggccgct cgcgattaat taacggaccg ccgcggacta    5160
gtgcccgggc caccggtgct cgaggagctt ggatctgtaa cggcgcagaa cagaaaacga    5220
aacaaagacg tagagttgag caagcagggt caggcaaagc gtggagagcc ggctgagtct    5280
aggtaggctc caagggagcg ccggacaaag gcccggtctc gacctgagct ttaaacttac    5340
ctagacggcg gacgcagttc aggaggcacc acaggcggga ggcggcagaa cgcgactcaa    5400
ccggcgtgga tggcggcctc agtaggcgcg gcggcgcgt gaaggagaga tgcgagcccc    5460
tcgatcgagg agcttttgc aaaagcctag gcctccaaaa aagcctcctc actacttctg    5520
gaatagctca gaggccgagg cggcctcggc tctgcataa ataaaaaaaa ttagtcagcc    5580
atggggcgga gaatgggcgg aactgggcgg agttaggggc gggatgggcg gagttagggg    5640
cgggactatg gttgctgact aattgagatg catgctttgc atacttctgc ctgctgggga    5700
gcctggggac tttccacacc tggttgctga ctaattgaga tgcatgcttt gcatacttct    5760
gcctgctggg gagcctgggg actttccaca ccctaactga cacacattcc acagccaagc    5820
ttggatcgat ccagacatga taagatacat tgatgagttt ggacaaacca caactagaat    5880
gcagtgaaaa aaatgcttta tttgtgaaat ttgtgatgct attgctttat ttgtaaccat    5940
tataagctgc aataaacaag ttaacaacaa caattgcatt catttatgt ttcaggttca    6000 gggggaggtg tgggaggttt tttaaagcaa gtaaaacctc tacaaatgtg gtatggctga    6060
ttatgatctc tagtcaag                                                  6078
```

<210> SEQ ID NO 14
<211> LENGTH: 6384
<212> TYPE: DNA
<213> ORGANISM: Artificial sequence
<220> FEATURE:
<223> OTHER INFORMATION: pDSRG plasmid

<400> SEQUENCE: 14

```
gcactataca tcaaatattc cttattaacc cctttacaaa ttaaaaagct aaaggtacac      60 aattttttgag catagttatt aatagcagac actctatgcc tgtgtggagt aagaaaaaac    120
agtatgttat gattataact gttatgccta cttataaagg ttacagaata ttttccata     180 atttctttgt atagcagtgc agcttttttcc tttgtggtgt aaatagcaaa gcaagcaaga    240
gttctattac taaacacagc atgactcaaa aaacttagca attctgaagg aaagtccttg    300
gggtcttcta cctttctctt cttttttgga ggagtagaat gttgagagtc agcagtagcc    360
tcatcatcac tagatggcat tcttctgagc aaaacaggt tttcctcatt aaaggcattc      420
caccactgct cccattcatc agttccatag gttggaatct aaaatacaca aacaattaga    480
```

```
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt ccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca acacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaccaagt caggaaacca cttgtctcac atcctcgttt taagaacagt    1800
ttgtaaccaa aaacttactt aagccctggg aaccgcaagg ttgggccaat aaaggctatt   1860
cataataact catgccatga gtttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag ggggcatctg   2160
ttggtctgta gatgtaaggt cccctataag tccctggttg ccaccacctg tctcctattt   2220
tgacaaaaac actcttttt cccttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca gtttgcagc agagaatgaa tatgtctttg tctgatgggc    2700
tcatccgttt gtgcgcagac gggtcgtcct tggtgggaaa caaccccttg ctgcttctc    2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
```

```
taacaatgcg ctcatcgtca tcctcggcac cgtcaccctg gatgctgtag gcataggctt    2940
ggttatgccg gtactgccgg gcctcttgcg ggatatcgtc cattccgaca gcatcgccag    3000
tcactatggc gtgctgctag cgtcttccg cttcctcgct cactgactcg ctgcgctcgg     3060
tcgttcggct gcggcgagcg gtatcagctc actcaaaggc ggtaatacgg ttatccacag    3120
aatcagggga taacgcagga agaacatgt gagcaaaagg ccagcaaaag gccaggaacc     3180
gtaaaaaggc cgcgttgctg gcgttttcc ataggctccg ccccctgac gagcatcaca     3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc aacccggta agacacgact     3540 tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg aaaaagagt tggtagctct tgatccggca     3720
aacaaaccac cgctggtagc ggtggttttt ttgtttgcaa gcagcagatt acgcgcagaa    3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atccccatg ttgtgcaaaa      4380 aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca acacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
cgacacggaa atgttgaata ctcatactct tcctttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gagcttgtcg acagatcccc ctcttcattt ctttatgttt taaatgcact gacctcccac    5100
attccctttt tagtaaaata ttcagaaata atttaaatac atcattgcaa tgaaaataaa    5160
tgttttttat taggcagaat ccagatgctc aaggcccttc ataatatccc ccagtttagt    5220
agttggactt agggaacaaa ggaacctta atagaaattg gacagcaaga aagcgagggg    5280
```

```
gatctggatc cctcgaggaa ttcccgggga tccgtcgacc tgcagcagct tttagagcag      5340
aagtaacact tccgtacagg cctagaagta aaggcaacat ccactgagga gcagttcttt      5400
gatttgcacc accaccggat ccgggacctg aaataaaaga caaaaagact aaacttacca      5460
gttaactttc tggtttttca gttcctcgag gagcttggat ctgtaacggc gcagaacaga      5520
aaacgaaaca aagacgtaga gttgagcaag cagggtcagg caaagcgtgg agagccggct      5580
gagtctaggt aggctccaag ggagcgccgg acaaaggccc ggtctcgacc tgagctttaa      5640
acttacctag acggcggacg cagttcagga ggcaccacag gcgggaggcg gcagaacgcg      5700
actcaaccgg cgtggatggc ggcctcaggt agggcggcgg gcgcgtgaag gagagatgcg      5760 agccctcga tcgaggagct ttttgcaaaa gcctaggcct ccaaaaaagc ctcctcacta      5820
cttctggaat agctcagagg ccgaggcggc ctcggcctct gcataaataa aaaaaattag      5880
tcagccatgg ggcggagaat gggcggaact gggcggagtt aggggcggga tgggcggagt      5940
taggggcggg actatggttg ctgactaatt gagatgcatg ctttgcatac ttctgcctgc      6000
tggggagcct ggggactttc cacacctggt tgctgactaa ttgagatgca tgctttgcat      6060
acttctgcct gctggggagc ctggggactt tccacaccct aactgacaca cattccacag      6120
ccaagcttgg atcgatccag acatgataag atacattgat gagtttggac aaaccacaac      6180
tagaatgcag tgaaaaaaat gctttatttg tgaaatttgt gatgctattg ctttatttgt      6240
aaccattata agctgcaata aacaagttaa caacaacaat tgcattcatt ttatgtttca      6300
ggttcagggg gaggtgtggg aggttttttta aagcaagtaa aacctctaca aatgtggtat      6360
ggctgattat gatctctagt caag                                             6384

<210> SEQ ID NO 15
<211> LENGTH: 384
<212> TYPE: DNA
<213> ORGANISM: Homo sapiens
<220> FEATURE:
<221> NAME/KEY: CDS
<222> LOCATION: 1..384
<220> FEATURE:
<221> NAME/KEY: sig_peptide
<222> LOCATION: 1..57

<400> SEQUENCE: 15 atg tcg cca tca caa ctc att ggg ttt ctg ctg ctc tgg gtt cca gcc        48
Met Ser Pro Ser Gln Leu Ile Gly Phe Leu Leu Leu Trp Val Pro Ala
1               5                   10                  15 tcc agg ggt gaa att gtg ctg act cag gtt cca gac ttt cag tct gtg        96
Ser Arg Gly Glu Ile Val Leu Thr Gln Val Pro Asp Phe Gln Ser Val
            20                  25                  30 act cca aag gag aaa gtc acc atc acc tgc cgg gcc agt cag agc att       144
Thr Pro Lys Glu Lys Val Thr Ile Thr Cys Arg Ala Ser Gln Ser Ile
        35                  40                  45 ggt agt agc tta cac tgg tac cag cag aaa cca gat cag tct cca aag       192
Gly Ser Ser Leu His Trp Tyr Gln Gln Lys Pro Asp Gln Ser Pro Lys
    50                  55                  60 ctc ctc atc aag tat gct tcc cag tcc ctc tca ggg gtc ccc tcg agg       240
Leu Leu Ile Lys Tyr Ala Ser Gln Ser Leu Ser Gly Val Pro Ser Arg
65                  70                  75                  80 ttc agt ggc agt gga tct ggg aca gat ttc acc ctc acc atc aat agc       288
Phe Ser Gly Ser Gly Ser Gly Thr Asp Phe Thr Leu Thr Ile Asn Ser
                85                  90                  95 ctg gaa gct gaa gat gct gca gcg tat tac tgt cat cag agt agt cgt       336
Leu Glu Ala Glu Asp Ala Ala Ala Tyr Tyr Cys His Gln Ser Ser Arg
            100                 105                 110
```

```
tta cct cac act ttc ggc gga ggg acc aag gtg gag atc aaa cga act    384
Leu Pro His Thr Phe Gly Gly Gly Thr Lys Val Glu Ile Lys Arg Thr
        115                 120                 125
```

<210> SEQ ID NO 16
<211> LENGTH: 128
<212> TYPE: PRT
<213> ORGANISM: Homo sapiens

<400> SEQUENCE: 16

```
Met Ser Pro Ser Gln Leu Ile Gly Phe Leu Leu Leu Trp Val Pro Ala
1               5                   10                  15

Ser Arg Gly Glu Ile Val Leu Thr Gln Val Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Arg
            100                 105                 110

Leu Pro His Thr Phe Gly Gly Gly Thr Lys Val Glu Ile Lys Arg Thr
        115                 120                 125
```

<210> SEQ ID NO 17
<211> LENGTH: 411
<212> TYPE: DNA
<213> ORGANISM: Homo sapiens
<220> FEATURE:
<221> NAME/KEY: CDS
<222> LOCATION: 1..411
<220> FEATURE:
<221> NAME/KEY: sig_peptide
<222> LOCATION: 1..57

<400> SEQUENCE: 17

```
atg gag ttt ggg ctg agc tgg gtt ttc ctt gtt gct ata tta aaa ggt    48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta cat    96
Val Gln Cys Glu Val Gln Leu Val Gln Ser Gly Gly Gly Leu Val His
            20                  25                  30 cct ggg ggg tcc ctg aga ctc tcc tgt gca gcc tct gga ttc acc ttc    144
Pro Gly Gly Ser Leu Arg Leu Ser Cys Ala Ala Ser Gly Phe Thr Phe
        35                  40                  45 agt agc ttt gct atg cac tgg gtt cgc cag gct cca gga aaa ggt ctg    192
Ser Ser Phe Ala Met His Trp Val Arg Gln Ala Pro Gly Lys Gly Leu
    50                  55                  60 gag tgg ata tca gtt att gat act cgt ggt gcc aca tac tat gca gac    240
Glu Trp Ile Ser Val Ile Asp Thr Arg Gly Ala Thr Tyr Tyr Ala Asp
65                  70                  75                  80 tcc gtg aag ggc cga ttc acc atc tcc aga gac aat gcc aag aac tcc    288
Ser Val Lys Gly Arg Phe Thr Ile Ser Arg Asp Asn Ala Lys Asn Ser
                85                  90                  95 ttg tat ctt caa atg aac agc ctg aga gcc gag gac atg gct gtg tat    336
Leu Tyr Leu Gln Met Asn Ser Leu Arg Ala Glu Asp Met Ala Val Tyr
            100                 105                 110 tac tgt gca aga ctg ggg aac ttc tac tac ggt atg gac gtc tgg ggc    384
Tyr Cys Ala Arg Leu Gly Asn Phe Tyr Tyr Gly Met Asp Val Trp Gly
```

```
Tyr Cys Ala Arg Leu Gly Asn Phe Tyr Tyr Gly Met Asp Val Trp Gly
        115                 120                 125 caa ggg acc acg gtc acc gtc tcc tca                              411
Gln Gly Thr Thr Val Thr Val Ser Ser
        130                 135

<210> SEQ ID NO 18
<211> LENGTH: 137
<212> TYPE: PRT
<213> ORGANISM: Homo sapiens

<400> SEQUENCE: 18

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val His
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
        130                 135

<210> SEQ ID NO 19
<211> LENGTH: 384
<212> TYPE: DNA
<213> ORGANISM: Homo sapiens
<220> FEATURE:
<221> NAME/KEY: CDS
<222> LOCATION: (1)..(384)

<400> SEQUENCE: 19 atg tcg cca tca caa ctc att ggg ttt ctg ctg ctc tgg gtt cca gcc     48
Met Ser Pro Ser Gln Leu Ile Gly Phe Leu Leu Leu Trp Val Pro Ala
1               5                   10                  15 tcc agg ggt gaa att gtg ctg act cag agc cca ggt acc ctg tct gtg     96
Ser Arg Gly Glu Ile Val Leu Thr Gln Ser Pro Gly Thr Leu Ser Val
            20                  25                  30 tct cca ggc gag aga gcc acc ctc tcc tgc cgg gcc agt cag agc att    144
Ser Pro Gly Glu Arg Ala Thr Leu Ser Cys Arg Ala Ser Gln Ser Ile
        35                  40                  45 ggt agc agc tta cac tgg tac cag cag aaa cca ggt cag gct cca agg    192
Gly Ser Ser Leu His Trp Tyr Gln Gln Lys Pro Gly Gln Ala Pro Arg
    50                  55                  60 ctt ctc atc aag tat gca tcc cag tcc ctc tca ggg atc ccc gat agg    240
Leu Leu Ile Lys Tyr Ala Ser Gln Ser Leu Ser Gly Ile Pro Asp Arg
65                  70                  75                  80 ttc agt ggc agt gga tct ggg aca gat ttc acc ctc acc atc agt aga    288
Phe Ser Gly Ser Gly Ser Gly Thr Asp Phe Thr Leu Thr Ile Ser Arg
                85                  90                  95 ctg gag cct gaa gat ttc gca gtg tat tac tgt cat cag agt agt cgt    336
Leu Glu Pro Glu Asp Phe Ala Val Tyr Tyr Cys His Gln Ser Ser Arg
            100                 105                 110
```

```
tta cct cac act ttc ggc caa ggg acc aag gtg gag atc aaa cgt aca      384
Leu Pro His Thr Phe Gly Gln Gly Thr Lys Val Glu Ile Lys Arg Thr
        115                 120                 125

<210> SEQ ID NO 20
<211> LENGTH: 128
<212> TYPE: PRT
<213> ORGANISM: Homo sapiens

<400> SEQUENCE: 20

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 21
<211> LENGTH: 411
<212> TYPE: DNA
<213> ORGANISM: Homo sapiens
<220> FEATURE:
<221> NAME/KEY: CDS
<222> LOCATION: (1)..(411)

<400> SEQUENCE: 21 atg gag ttt ggg ctg agc tgg gtt ttc ctt gtt gct ata tta aaa ggt       48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta aag       96
Val Gln Cys Glu Val Gln Leu Val Gln Ser Gly Gly Gly Leu Val Lys
            20                  25                  30 cct ggg ggg tcc ctg aga ctc tcc tgt gca gcc tct gga ttc acc ttc      144
Pro Gly Gly Ser Leu Arg Leu Ser Cys Ala Ala Ser Gly Phe Thr Phe
        35                  40                  45 agt agc ttt gct atg cac tgg gtt cgc cag gct cca gga aaa ggt ctg      192
Ser Ser Phe Ala Met His Trp Val Arg Gln Ala Pro Gly Lys Gly Leu
    50                  55                  60 gag tgg ata tca gtt att gat act cgt ggt gcc aca tac tat gca gac      240
Glu Trp Ile Ser Val Ile Asp Thr Arg Gly Ala Thr Tyr Tyr Ala Asp
65                  70                  75                  80 tcc gtg aag ggc cga ttc acc atc tcc aga gac aat gcc aag aac tcc      288
Ser Val Lys Gly Arg Phe Thr Ile Ser Arg Asp Asn Ala Lys Asn Ser
                85                  90                  95 ttg tat ctt caa atg aac agc ctg aga gcc gag gac act gct gtg tat      336
Leu Tyr Leu Gln Met Asn Ser Leu Arg Ala Glu Asp Thr Ala Val Tyr
            100                 105                 110 tac tgt gca aga ctg ggg aac ttc tac tac ggt atg gac gtc tgg ggc      384
Tyr Cys Ala Arg Leu Gly Asn Phe Tyr Tyr Gly Met Asp Val Trp Gly
        115                 120                 125
```

```
caa ggg acc acg gtc acc gtc tcc tca                              411
Gln Gly Thr Thr Val Thr Val Ser Ser
    130                 135

<210> SEQ ID NO 22
<211> LENGTH: 137
<212> TYPE: PRT
<213> ORGANISM: Homo sapiens

<400> SEQUENCE: 22

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135

<210> SEQ ID NO 23
<211> LENGTH: 2960
<212> TYPE: DNA
<213> ORGANISM: Artificial Sequence
<220> FEATURE:
<223> OTHER INFORMATION: Nucleotide sequence of chicken lysozyme MAR
      element

<400> SEQUENCE: 23
gatccgtaat acaattgtac caggttttgg tttattacat gtgactgacg gcttcctgtg     60
cgtgctcagg aaacggcagt tgggcactgc actgcccgt gatggtgcca cggtggctcc    120
tgccgccttc tttgatattc actctgttgt atttcatctc ttcttgccga tgaaaggata    180
taacagtctg tgaggaaata cttggtattt cttctgatca gcgttttat aagtaatgtt    240 gaatattgga taaggctgtg tgtcctttgt cttgggagac aaagcccaca gcaggtggtg    300
gttggggtgg tggcagctca gtgacaggag aggttttttt gcctgttttt tttgttgttt    360
ttttttttta agtaaggtgt tcttttttct tagtaaaatt tctactggac tgtatgtttt    420
gacaggtcag aaacatttct tcaaaagaag aaccttttgg aaactgtaca gcccttttct    480
ttcattccct ttttgctttc tgtgccaatg cctttggttc tgatttgcat tatggaaaac    540
gttgatcgga acttgaggtt tttatttata gtgtggcttg aaagcttgga tagctgttgt    600
tacatgagat accttattaa gtttaggcca gcttgatgct ttattttttt cccttttgaag   660 tagtgagcgt tctctggttt ttttccttg aaactggcga ggcttagatt tttctaatgg    720 gatttttta c ctgatgatct agttgcatac ccaaatgctt gtaaatgttt tcctagttaa    780
catgttgata acttcggatt tacatgttgt atatacttgt catctgtgtt tctagtaaaa    840
atatatggca tttatagaaa tacgtaattc ctgatttcct ttttttttta tctctatgct    900
```

| | | | | |
|---|---|---|---|---|
| ctgtgtgtac | aggtcaaaca | gacttcactc | ctatttttat ttatagaatt | ttatatgcag | 960 |
| tctgtcgttg | gttcttgtgt | tgtaaggata | cagccttaaa tttcctagag | cgatgctcag | 1020 |
| taaggcgggt | tgtcacatgg | gttcaaatgt | aaaacgggca cgtttggctg | ctgccttccc | 1080 |
| gagatccagg | acactaaact | gcttctgcac | tgaggtataa atcgcttcag | atcccaggga | 1140 |
| agtgtagatc | cacgtgcata | ttcttaaaga | agaatgaata ctttctaaaa | tattttggca | 1200 |
| taggaagcaa | gctgcatgga | tttgtttggg | acttaaatta ttttggtaac | ggagtgcata | 1260 |
| ggttttaaac | acagttgcag | catgctaacg | agtcacagca tttatgcaga | agtgatgcct | 1320 |
| gttgcagctg | tttacggcac | tgccttgcag | tgagcgattt gcagataggg | gtggggtgct | 1380 |
| ttgtgtcgtg | ttcccacacg | ctgccacaca | gccacctccc ggaacacatc | tcacctgctg | 1440 |
| ggtactttc | aaaccatctt | agcagtagta | gatgagttac tatgaaacag | agaagttcct | 1500 |
| cagttggata | ttctcatggg | atgtcttttt | tcccatgttg ggcaaagtat | gataaagcat | 1560 |
| ctctatttgt | aaattatgca | cttgttagtt | cctgaatcct ttctatagca | ccacttattg | 1620 |
| cagcaggtgt | aggctctggt | gtggcctgtg | tctgtgcttc aatcttttaa | gcttctttgg | 1680 |
| aaatacactg | acttgattga | agtctcttga | agatagtaaa cagtacttac | ctttgatccc | 1740 |
| aatgaaatcg | agcatttcag | ttgtaaaaga | attccgccta ttcataccat | gtaatgtaat | 1800 |
| tttacacccc | cagtgctgac | actttggaat | atattcaagt aatagacttt | ggcctcaccc | 1860 |
| tcttgtgtac | tgtatttgt | aatagaaaat | attttaaact gtgcatatga | ttattacatt | 1920 |
| atgaaagaga | cattctgctg | atcttcaaat | gtaagaaaat gaggagtgcg | tgtgctttta | 1980 |
| taaatacaag | tgattgcaaa | ttagtgcagg | tgtccttaaa aaaaaaaaaa | agtaatataa | 2040 |
| aaaggaccag | gtgtttttaca | agtgaaatac | attcctattt ggtaaacagt | tacattttta | 2100 |
| tgaagattac | cagcgctgct | gactttctaa | acataaggct gtattgtctt | cctgtaccat | 2160 |
| tgcatttcct | cattcccaat | ttgcacaagg | atgtctgggt aaactattca | agaaatggct | 2220 |
| ttgaaataca | gcatgggagc | ttgtctgagt | tggaatgcag agttgcactg | caaaatgtca | 2280 |
| ggaaatggat | gtctctcaga | atgcccaact | ccaaaggatt ttatatgtgt | atatagtaag | 2340 |
| cagtttcctg | attccagcag | gccaaagagt | ctgctgaatg ttgcgttgcc | ggagacctgt | 2400 |
| atttctcaac | aaggtaagat | ggtatcctag | caactgcgga ttttaataca | ttttcagcag | 2460 |
| aagtacttag | ttaatctcta | cctttaggga | tcgtttcatc atttttagat | gttatacttg | 2520 |
| aaatactgca | taactttag | ctttcatggg | ttccttttt tcagccttta | ggagactgtt | 2580 |
| aagcaatttg | ctgtccaact | tttgtgttgg | tcttaaactg caatagtagt | ttaccttgta | 2640 |
| ttgaagaaat | aaagaccatt | tttatattaa | aaaatacttt tgtctgtctt | catttgact | 2700 |
| tgtctgatat | ccttgcagtg | ctcattatgt | cagttctgtc agatattcag | acatcaaaac | 2760 |
| ttaacgtgag | ctcagtggag | ttacagctgc | ggttttgatg ctgttattat | ttctgaaact | 2820 |
| agaaatgatg | ttgtcttcat | ctgctcatca | aacacttcat gcagagttta | aggctagtga | 2880 |
| gaaatgcata | catttattga | tacttttta | aagtcaactt tttatcagat | ttttttttca | 2940 |
| tttggaaata | tattgttttc | | | 2960 |

<210> SEQ ID NO 24
<211> LENGTH: 14910
<212> TYPE: DNA
<213> ORGANISM: Artificial Sequence
<220> FEATURE:
<223> OTHER INFORMATION: Nucleotide sequence of pinAIL10/MAR(-)

<400> SEQUENCE: 24

```
gcactataca tcaaatattc cttattaacc cctttacaaa ttaaaaagct aaaggtacac      60
aatttttgag catagttatt aatagcagac actctatgcc tgtgtggagt aagaaaaaac     120
agtatgttat gattataact gttatgccta cttataaagg ttacagaata tttttccata     180
attttcttgt atagcagtgc agcttttcc tttgtggtgt aaatagcaaa gcaagcaaga     240
gttctattac taaacacagc atgactcaaa aacttagca attctgaagg aaagtccttg     300
gggtcttcta cctttctctt cttttttgga ggagtagaat gttgagagtc agcagtagcc     360
tcatcatcac tagatggcat ttcttctgag caaaacaggt tttcctcatt aaaggcattc     420
caccactgct cccattcatc agttccatag gttggaatct aaaatacaca acaattaga     480 atcagtagtt taacacatta tacacttaaa aattttatat ttaccttaga gctttaaatc     540
tctgtaggta gtttgtccaa ttatgtcaca ccacagaagt aaggttcctt cacaaagatc     600
gatctaaagc cagcaaaagt cccatggtct tataaaaatg catagcttta ggaggggagc     660
agagaacttg aaagcatctt cctgttagtc tttcttctcg tagacttcaa acttatactt     720
gatgcctttt tcctcctgga cctcagagag gacgcctggg tattctggga gaagtttata     780
tttccccaaa tcaatttctg ggaaaaacgt gtcactttca aattcctgca tgatccttgt     840
cacaaagagt ctgaggtggc ctggttgatt catggcttcc tggtaaacag aactgcctcc     900
gactatccaa accatgtcta ctttacttgc caattccggt tgttcaataa gtcttaaggc     960
atcatccaaa cttttggcaa gaaaatgagc tcctcgtggt ggttctttga gttctctact    1020
gagaactata ttaattctgt cctttaaagg tcgattcttc tcaggaatgg agaaccaggt    1080
tttcctaccc ataatcacca gattctgttt accttccact gaagaggttg tggtcattct    1140
ttggaagtac ttgaactcgt tcctgagcgg aggccaggt aggtctccgt tcttgccaat    1200
ccccatattt tgggacacgg cgacgatgca gttcaatggt cgaaccatga tggcagcggg    1260
gataaaatcc taccagcctt cacgctagga ttgccgtcaa gtttggcgcg aaatcgcagc    1320
cctgagctgt cccccccccc aagctcagat ctgagcttgg tccctatggt gagtccgttc    1380
cgctcttgtg atgatagcca gacaagaaag agacaataca agacaaacac caaatagtag    1440
aaatagagac aagggtcact tatccgaggg tccctgttcg ggcgccagct gccgcagtcg    1500
gccgacctga gggtcgccgg ggtctgcggg gggaccctct ggaaagtgaa ggataagtga    1560
cgagcggaga cgggatggcg aacagacaca aacacacaag aggtgaatgt taggactgtt    1620
gcaagtttac tcaaaaaatc agcactcttt tatatcttgg tttacataag catttacata    1680
agatttggat aaaattccaa agaacatagg aaaatagaac actcagagct cagatcagaa    1740
cctttgatac caaaccaagt caggaaacca cttgtctcac atcctcgttt taagaacagt    1800
ttgtaaccaa aaacttactt aagccctggg aaccgcaagg ttgggccaat aaaggctatt    1860
cataataact catgccatga gttttttgcag aataatgttc tattagtcca gccactgtcc    1920
cctccttggt atggaaaatc tttccccaaa agtgcattcc tgttcctaga taaatataat    1980
catgtacctg ttgtttcatg tcgtcttttt cttcttgaga caacatacac caaggaggtc    2040
tagctctggc gagtctttca cgaaaaggga gggatctata taacacttta tagccattga    2100
ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actcttttt ccctttttta cttctaggcc tgtggtcaat agtccttgca    2280
cctgttcttc aattgaggtt gagcgtctct ttctatttc tattcccatt tctaacttct    2340
gaatttgagt aaaaatagta ctaaaagata atgattcatt tcttaacata gtaactaata    2400
```

```
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca agtttgcagc agagaatgaa tatgtctttg tctgatgggc    2700
tcatccgttt gtgcgcagac gggtcgtcct tggtgggaaa caaccccttg ctgcttctc     2760 ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag gcataggctt    2940
ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga agaacatgt  gagcaaaagg ccagcaaaag gccaggaacc    3180
gtaaaaaggc cgcgttgctg gcgttttttcc ataggctccg ccccccctgac gagcatcaca    3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc caacccggta agacacgact    3540
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt ttgtttgcaa gcagcagatt acgcgcagaa    3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca cacgggata  ataccgcgcc acatagcaga actttaaaag    4620
tgctcatcat tggaaaacgt tcttcgggc  gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
```

```
cgacacggaa atgttgaata ctcatactct tcctttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgct taattaatcg cgatggccac atatggagct ctctagaaaa caatatattt    5100
ccaaatgaaa aaaaaatctg ataaaaagtt gactttaaaa aagtatcaat aaatgtatgc    5160
atttctcact agccttaaac tctgcatgaa gtgtttgatg agcagatgaa gacaacatca    5220
tttctagttt cagaaataat aacagcatca aaaccgcagc tgtaactcca ctgagctcac    5280
gttaagtttt gatgtctgaa tatctgacag aactgacata atgagcactg caaggatatc    5340
agacaagtca aaatgaagac agacaaaagt atttttttaat ataaaaatgg tctttatttc    5400
ttcaatacaa ggtaaactac tattgcagtt taagaccaac acaaaagttg gacagcaaat    5460
tgcttaacag tctcctaaag gctgaaaaaa aggaacccat gaaagctaaa agttatgcag    5520
tatttcaagt ataacatcta aaaatgatga aacgatccct aaaggtagag attaactaag    5580
tacttctgct gaaaatgtat taaaatccgc agttgctagg ataccatctt accttgttga    5640
gaaatacagg tctccggcaa cgcaacattc agcagactct ttggcctgct ggaatcagga    5700
aactgcttac tatatacaca tataaaatcc tttggagttg ggcattctga gagacatcca    5760
tttcctgaca ttttgcagtg caactctgca ttccaactca gacaagctcc catgctgtat    5820
ttcaaagcca tttcttgaat agtttaccca gacatccttg tgcaaattgg gaatgaggaa    5880
atgcaatggt acaggaagac aatacagcct tatgtttaga aagtcagcag cgctggtaat    5940
cttcataaaa atgtaactgt ttaccaaata ggaatgtatt tcacttgtaa aacacctggt    6000
cctttttata ttactttttt ttttttttaa ggacacctgc actaatttgc aatcacttgt    6060
atttataaaa gcacacgcac tcctcatttt cttacatttg aagatcagca gaatgtctct    6120
ttcataatgt aataatcata tgcacagttt aaaatatttt ctattacaaa atacagtaca    6180
caagagggtg aggccaaagt ctattacttg aatatattcc aaagtgtcag cactgggggt    6240
gtaaaattac attacatggt atgaataggc ggaattcttt tacaactgaa atgctcgatt    6300
tcattgggat caaaggtaag tactgtttac tatcttcaag agacttcaat caagtcagtg    6360
tatttccaaa gaagcttaaa agattgaagc acagacacag gccacaccag agcctacacc    6420
tgctgcaata agtggtgcta tagaaaggat tcaggaacta acaagtgcat aatttacaaa    6480
tagagatgct ttatcatact ttgcccaaca tgggaaaaaa gacatcccat gagaatatcc    6540
aactgaggaa cttctctgtt tcatagtaac tcatctacta ctgctaagat ggtttgaaaa    6600
gtacccagca ggtgagatgt gttccgggag gtggctgtgt ggcagcgtgt gggaacacga    6660
cacaaagcac cccacccccta tctgcaaatc gctcactgca aggcagtgcc gtaaacagct    6720
gcaacaggca tcacttctgc ataaatgctg tgactcgtta gcatgctgca actgtgttta    6780
aaacctatgc actccgttac caaaataatt taagtcccaa acaaatccat gcagcttgct    6840
tcctatgcca aaatatttta gaaagtattc attcttcttt aagaatatgc acgtggatct    6900
acacttccct gggatctgaa gcgatttata cctcagtgca gaagcagttt agtgtcctgg    6960
atctcgggaa ggcagcagcc aaacgtgccc gttttacatt tgaacccatg tgacaacccg    7020
ccttactgag catcgctcta ggaaatttaa ggctgtatcc ttacaacaca agaaccaacg    7080
acagactgca tataaaattc tataaataaa aataggagtg aagtctgttt gacctgtaca    7140
cacagagcat agagataaaa aaaaaaggaa atcaggaatt acgtatttct ataaatgcca    7200
```

```
tatatttta   ctagaaacac   agatgacaag   tatatacaac   atgtaaatcc   gaagttatca    7260
acatgttaac   taggaaaaca   tttacaagca   tttgggtatg   caactagatc   atcaggtaaa    7320
aaatcccatt   agaaaaatct   aagcctcgcc   agtttcaaag   gaaaaaaacc   agagaacgct    7380
cactacttca   aagggaaaaa   aataaagcat   caagctggcc   taaacttaat   aaggtatctc    7440
atgtaacaac   agctatccaa   gctttcaagc   cacactataa   ataaaaacct   caagttccga    7500
tcaacgtttt   ccataatgca   aatcagaacc   aaaggcattg   gcacagaaag   caaaaaggga    7560
atgaaagaaa   agggctgtac   agtttccaaa   aggttcttct   tttgaagaaa   tgtttctgac    7620
ctgtcaaaac   atacagtcca   gtagaaattt   tactaagaaa   aaagaacacc   ttacttaaaa    7680
aaaaaaaaca   acaaaaaaaa   caggcaaaaa   aacctctcct   gtcactgagc   tgccaccacc    7740
ccaaccacca   cctgctgtgg   gctttgtctc   ccaagacaaa   ggacacacag   ccttatccaa    7800
tattcaacat   tacttataaa   aacgctgatc   agaagaaata   ccaagtattt   cctcacagac    7860
tgttatatcc   tttcatcggc   aagaagagat   gaaatacaac   agagtgaata   tcaaagaagg    7920
cggcaggagc   caccgtggca   ccatcaccgg   gcagtgcagt   gcccaactgc   cgtttcctga    7980
gcacgcacag   gaagccgtca   gtcacatgta   ataaaccaaa   acctggtaca   attgtattac    8040
ggatcccggt   ggcgcgccgt   ttaaaccctc   agctaccgat   gtacgggcca   gatatacgcg    8100
ttgacattga   ttattgacta   gttattaata   gtaatcaatt   acgggtcat   tagttcatag    8160 cccatatatg   gagttccgcg   ttacataact   tacggtaaat   ggcccgcctg   gctgaccgcc    8220
caacgacccc   cgcccattga   cgtcaataat   gacgtatgtt   cccatagtaa   cgccaatagg    8280
gactttccat   tgacgtcaat   gggtggacta   tttacggtaa   actgcccact   ggcagtaca    8340 tcaagtgtat   catatgccaa   gtacgccccc   tattgacgtc   aatgacggta   aatggcccgc    8400
ctggcattat   gcccagtaca   tgaccttatg   ggactttcct   acttggcagt   acatctacgt    8460
attagtcatc   gctattacca   tggtgatgcg   gttttggcag   tacatcaatg   ggcgtggata    8520
gcggtttgac   tcacggggat   ttccaagtct   ccaccccatt   gacgtcaatg   ggagtttgtt    8580
ttggcaccaa   aatcaacggg   actttccaaa   atgtcgtaac   aactccgccc   cattgacgca    8640
aatgggcggt   aggcgtgtac   ggtgggaggt   ctatataagc   agagctctct   ggctaactag    8700
agaacccact   gcttactggc   ttatcgaaat   taatacgact   cactatagca   attgcacgtg    8760
tggccacagg   taagtttaaa   gctcaggtcg   agaccgggcc   tttgtccggc   gctcccttgg    8820
agcctaccta   gactcagccg   gctctccacg   ctttgcctga   ccctgcttgc   tcaactctac    8880
gtctttgttt   cgttttctgt   tcctttctct   ccacaggctt   aagcttggta   ccagaaagtt    8940
aacatggctg   tcttggggct   gctcttctgc   ctggtgacat   cccaagctg   tgtcctatcc    9000 caggtgcagc   tggtggagtc   tgggggaggc   gtggtccagc   ctgggaggtc   cctgagactc    9060
tcctgtgcag   cctctggatt   cactttcagt   gactatcata   tggcctgggt   ccgccaggct    9120
ccaggcaagg   ggctggagtg   ggtggcaagc   attacttg   atgctaccta   cacttactat    9180
cgcgactccg   tgcgcggccg   cttcaccatc   tccagagaca   attccaagaa   cacgctgtat    9240
ctgcaaatga   acagcctgag   agctgaggac   acggctgtgt   attactgtgc   gagacatcga    9300
ggctttagcg   tctggcttga   ttactggggc   caaggcaccc   tggtcaccgt   ctcgtcggct    9360
agcaccaagg   gcccatcggt   cttccccctg   gcaccctcct   ccaagagcac   ctctgggggc    9420
acagcggccc   tgggctgcct   ggtcaaggac   tacttccccg   aaccggtgac   ggtgtcgtgg    9480
aactcaggcg   ccctgaccag   cggcgtgcac   accttcccgg   ctgtcctaca   gtcctcagga    9540
ctctactccc   tcagcagcgt   ggtgaccgtg   ccctccagca   gcttgggcac   ccagacctac    9600
```

```
atctgcaacg tgaatcacaa gcccagcaac accaaggtgg acaagaaagt tgagcccaaa    9660
tcttgtgaca aaactcacac atgcccaccg tgcccagcac ctgaactcct gggggggaccg   9720 tcagtcttcc tcttcccccc aaaacccaag acacccctca tgatctcccg gacccctgag   9780
gtcacatgcg tggtggtgga cgtgagccac gaagaccctg aggtcaagtt caactggtac   9840
gtggacggcg tggaggtgca taatgccaag acaaagccgc gggaggagca gtacaacagc   9900
acgtaccgtg tggtcagcgt cctcaccgtc ctgcaccagg actggctgaa tggcaaggag   9960
tacaagtgca aggtctccaa caaagccctc ccagccccca tcgagaaaac catctccaaa  10020
gccaaagggc agccccgaga accacaggtg tacaccctgc ccccatcccg ggatgagctg  10080
accaagaacc aggtcagcct gacctgcctg gtcaaaggct tctatcccag cgacatcgcc  10140
gtggagtggg agagcaatgg gcagccggag aacaactaca agaccacgcc tcccgtgctg  10200
gactccgacg gctccttctt cctctacagc aagctcaccg tggacaagag caggtggcag  10260
caggggaacg tcttctcatg ctccgtgatg catgaggctc tgcacaacca ctacacgcag  10320
aagagcctct ccctgtctcc gggtaaatga atcgatgatt ctagatacgg gtccggagga  10380
tccagatccc cctcgctttc ttgctgtcca atttctatta aaggttcctt tgttccctaa  10440
gtccaactac taaactgggg gatattatga agggccttga gcatctggat tctgcctaat  10500
aaaaaacatt tattttcatt gcaatgatgt atttaaatta tttctgaata ttttactaaa  10560
aagggaatgt gggaggtcag tgcatttaaa acataaagaa atgaagaggg ggatctgtcg  10620
acaagctcta gagagctcac gcgttgatca tgtacaggcc ggccaagctt tcgactagct  10680
tggcacgcca gaaatccgcg cggtggtttt tgggggtcgg gggtgtttgg cagccacaga  10740
cgcccggtgt tcgtgtcgcg ccagtacatg cggtccatgc ccaggccatc caaaaaccat  10800
gggtctgtct gctcagtcca gtcgtggacc tgaccccacg caacgcccaa aataataacc  10860
cccacgaacc ataaaccatt ccccatgggg gaccccgtcc ctaacccacg ggccagtgg   10920 ctatggcagg gcctgccgcc ccgacgttgg ctgcagcccc tgggccttca cccgaacttg  10980
gggggtgggg tggggaaaag gaagaaacgc gggcgtattg gccccaatgg ggtctcggtg  11040
gggtatcgac agagtgccag ccctgggacc gaaccccgcg tttatgaaca aacgacccaa  11100
cacccgtgcg ttttattctg tcttttttatt gccgtcatag cgcgggttcc ttccggtatt  11160
gtctccttcc gtgtttcagt tagcctcccc catctcccga tccggacgag tgctggggcg  11220
tcggtttcca ctatcggcga gtacttctac acagccatcg gtccagacgg ccgcgcttct  11280
gcgggcgatt tgtgtacgcc cgacagtccc ggctccggat cggacgattg cgtcgcatcg  11340
accctgcgcc caagctgcat catcgaaatt gccgtcaacc aagctctgat agagttggtc  11400
aagaccaatg cggagcatat acgcccggag ccgcggcgat cctgcaagct ccggatgcct  11460
ccgctcgaag tagcgcgtct gctgctccat acaagccaac cacggcctcc agaagaagat  11520
gttggcgacc tcgtattggg aatccccgaa catcgcctcg ctccagtcaa tgaccgctgt  11580
tatgcggcca ttgtccgtca ggacattgtt ggagccgaaa tccgcgtgca cgaggtgccg  11640
gacttcgggg cagtcctcgg cccaaagcat cagctcatcg agagcctgcg cgacggacgc  11700
actgacggtg tcgtccatca cagtttgcca gtgatacaca tggggatcag caatcgcgca  11760
tatgaaatca cgccatgtag tgtattgacc gattccttgc ggtccgaatg ggccgaaccc  11820
gctcgtctgg ctaagatcgg ccgcagcgat cgcatccatg gcctccgcga ccggctgcag  11880
aacagcgggc agttcggttt caggcaggtc ttgcaacgtg acaccctgtg cacggcggga  11940
gatgcaatag gtcaggctct cgctgaattc cccaatgtca agcacttccg gaatcgggag  12000
```

```
cgcggccgat gcaaagtgcc gataaacata acgatctttg tagaaaccat cggcgcagct    12060 atttaccocgc aggacatatc cacgccctcc tacatcgaag ctgaaagcac gagattcttc    12120
gccctccgag agctgcatca ggtcggagac gctgtcgaac ttttcgatca gaaacttctc    12180
gacagacgtc gcggtgagtt caggctttt catatctcat gcccccggg gatctgcggc    12240 acgctgttga cgctgttaag cgggtcgctg cagggtcgct cggtgttcga ggccacacgc    12300
gtcaccttaa tatgcgaagt ggacctcgga ccgcgccgcc ccgactgcat ctgcgtgttc    12360
gaattcgcca atgacaagac gctgggcggg gtttgtgtca tcatagaact aaagacatgc    12420
aaatatattt cttccgggga caccgccagc aaacgcgagc aacgggccac ggggatgaag    12480
cagggcggca cctcgctaac ggattcacca ctccaagaat tggagccaat caattcttgc    12540
ggagaactgt gaatgcgcaa accaacccctt ggcagaacat atccatcgcg tccgccatct    12600
ccagcagccg cacgcggcgc atctcggggc cgacgcgctg gctacgtct tgctggcgtt    12660 cgcacaggcc ggccagcgcg cggccggccg gtaccacgcg ttggccacat atggcggccg    12720
ctcgcgatta attaatcgcg atggccacat atggagctct ctagagcttg tcgacagatc    12780
cccctcttca tttctttatg ttttaaatgc actgacctcc cacattccct ttttagtaaa    12840
atattcagaa ataatttaaa tacatcattg caatgaaaat aaatgttttt tattaggcag    12900
aatccagatg ctcaaggccc ttcataatat cccccagttt agtagttgga cttagggaac    12960
aaaggaacct ttaatagaaa ttggacagca agaaagcgag ggggatctgg atcctccgga    13020
gggccctgga tcctcctacg tatctagaat catcgattaa cactctcccc tgttgaagct    13080
ctttgtgacg ggcgagctca ggccctgatg ggtgacttcg caggcgtaga ctttgtgttt    13140
ctcgtagtct gctttgctca gcgtcagggt gctgctgagg ctgtaggtgc tgtccttgct    13200
gtcctgctct gtgacactct cctggagtt acccgattgg agggcgttat ccaccttcca    13260
ctgtactttg gcctctctgg gatagaagtt attcagcagg cacacaacag aggcagttcc    13320
agatttcaac tgctcatcag atggcgggaa gatgaagaca gatggtgcag ccaccgtacg    13380
tttcagttcc agcttggtcc caggtccaaa cgtgtacccg ctataatact ggtgacagta    13440
gtaagttgca aaatcttcag gttgcagact gctgatggtg agagtgaaat ctgtcccaga    13500
tccactgcca ctgaaccttg atgggacccc cgcttgcaaa gggcttgcat tatagatcag    13560
gagcttaggg gctttccctg gtttctgctg ataccaggcc aagttctcaa aaatgttctg    13620
acttgtcttg caagtgatgg tgactctgtc tcctacagat gcagacaggg aggatggaga    13680
ctgggtcatc tggatgtcac atctcatggc tgggaggaag agcaccaaaa gccctaaaag    13740
ttgaactgga gccatctcga gaattcttaa gcctgtggag agaaaggaac agaaaacgaa    13800
acaaagacgt agagttgagc aagcagggtc aggcaaagcg tggagagccg gctgagtcta    13860
ggtaggctcc aagggagcgc cggacaaagg cccggtctcg acctgagctt taaacttacc    13920 tgtgccaca cgtgcaattg ctatagtgag tcgtattaat ttcgataagc cagtaagcag    13980
tgggttctct agttagccag agagctctgc ttatatagac ctcccaccgt acacgcctac    14040
cgcccatttg cgtcaatggg gcggagttgt tacgacattt tggaaagtcc cgttgatttt    14100
ggtgccaaaa caaactccca ttgacgtcaa tggggtggag acttggaaat ccccgtgagt    14160
caaaccgcta tccacgccca ttgatgtact gccaaaaccg catcaccatg gtaatagcga    14220
tgactaatac gtagatgtac tgccaagtag gaaagtccca taaggtcatg tactgggcat    14280
aatgccaggc gggccattta ccgtcattga cgtcaatagg gggcgtactt ggcatatgat    14340
acacttgatg tactgccaag tgggcagttt accgtaaata gtccacccat tgacgtcaat    14400
```

-continued

```
ggaaagtccc tattggcgtt actatgggaa catacgtcat tattgacgtc aatgggcggg    14460
ggtcgttggg cggtcagcca ggcgggccat ttaccgtaag ttatgtaacg cggaactcca    14520
tatatgggct atgaactaat gaccccgtaa ttgattacta ttaataacta gtcaataatc    14580
aatgtcaacg cgtatatctg gcccgtacat cggtaactag tcggaccggc ccgggccacc    14640
ggtgctcgaa gcttggatcg atccagacat gataagatac attgatgagt ttggacaaac    14700
cacaactaga atgcagtgaa aaaaatgctt tatttgtgaa atttgtgatg ctattgcttt    14760
atttgtaacc attataagct gcaataaaca agttaacaac aacaattgca ttcattttat    14820
gtttcaggtt caggggggagg tgtgggaggt tttttaaagc aagtaaaacc tctacaaatg    14880
tggtatggct gattatgatc tctagtcaag                                     14910
```

<210> SEQ ID NO 25
<211> LENGTH: 15083
<212> TYPE: DNA
<213> ORGANISM: Artificial Sequence
<220> FEATURE:
<223> OTHER INFORMATION: Nucleotide sequence of pAIL10V1/puro/MAR(-)

<400> SEQUENCE: 25

```
gcactataca tcaaatattc cttattaacc cctttacaaa ttaaaaagct aaaggtacac      60 aattttttgag catagttatt aatagcagac actctatgcc tgtgtggagt aagaaaaaac    120
agtatgttat gattataact gttatgccta cttataaagg ttacagaata ttttttccata    180 atttctcttgt atagcagtgc agcttttttcc tttgtggtgt aaatagcaaa gcaagcaaga    240
gttctattac taaacacagc atgactcaaa aaacttagca attctgaagg aaagtccttg     300
gggtcttcta cctttctctt ctttttttgga ggagtagaat gttgagagtc agcagtagcc     360
tcatcatcac tagatggcat ttcttctgag caaaacaggt tttcctcatt aaaggcattc     420
caccactgct cccattcatc agttccatag gttggaatct aaaatacaca acaattaga      480 atcagtagtt taacacatta tacacttaaa aattttatat ttaccttaga gctttaaatc     540
tctgtaggta gtttgtccaa ttatgtcaca ccacagaagt aaggttcctt cacaaagatc     600
gatctaaagc cagcaaaagt cccatggtct tataaaaatg catagcttta ggaggggagc     660
agagaacttg aaagcatctt cctgttagtc tttcttctcg tagacttcaa acttatactt     720
gatgcctttt tcctcctgga cctcagagag gacgcctggg tattctggga gaagtttata     780
tttccccaaa tcaatttctg ggaaaaacgt gtcactttca aattcctgca tgatccttgt     840
cacaaagagt ctgaggtggc ctggttgatt catggcttcc tggtaaacag aactgcctcc     900
gactatccaa accatgtcta ctttacttgc caattccggt tgttcaataa gtcttaaggc     960
atcatccaaa cttttggcaa gaaaatgagc tcctcgtggt ggttctttga gttctctact    1020
gagaactata ttaattctgt cctttaaagg tcgattcttc tcaggaatgg agaaccaggt    1080
tttcctaccc ataatcacca gattctgttt accttccact gaagaggttg tggtcattct    1140
ttggaagtac ttgaactcgt tcctgagcgg aggccagggt aggtctccgt tcttgccaat    1200
ccccatattt tgggacacgg cgacgatgca gttcaatggt cgaaccatga tggcagcggg    1260
gataaaatcc taccagcctt cacgctagga ttgccgtcaa gtttggcgcg aaatcgcagc    1320
cctgagctgt cccccccccc aagctcagat ctgagcttgg tccctatggt gagtccgttc    1380
cgctcttgtg atgatagcca gacaagaaag agacaataca agacaaacac caaatagtag    1440
aaatagagac aagggtcact tatccgaggg tccctgttcg ggcgccagct gccgcagtcg    1500
gccgacctga gggtcgccgg ggtctgcggg gggaccctct ggaaagtgaa ggataagtga    1560
```

```
cgagcggaga cgggatggcg aacagacaca aacacacaag aggtgaatgt taggactgtt    1620
gcaagtttac tcaaaaaatc agcactcttt tatatcttgg tttacataag catttacata    1680
agatttggat aaattccaaa agaacatagg aaaatagaac actcagagct cagatcagaa    1740
cctttgatac caaaccaagt caggaaacca cttgtctcac atcctcgttt taagaacagt    1800
ttgtaaccaa aaacttactt aagccctggg aaccgcaagg ttgggccaat aaaggctatt    1860
cataataact catgccatga gttttttgcag aataatgttc tattagtcca gccactgtcc   1920
cctccttggt atggaaaatc tttccccaaa agtgcattcc tgttcctaga taaatataat    1980
catgtacctg ttgtttcatg tcgtcttttt cttcttgaga caacatacac caaggaggtc    2040
tagctctggc gagtctttca cgaaaaggga gggatctata taacacttta tagccattga    2100
ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actcttttttt ccctttttta cttctaggcc tgtggtcaat agtccttgca    2280
cctgttcttc aattgaggtt gagcgtctct ttctattttc tattcccatt tctaacttct    2340
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca agtttgcagc agagaatgaa tatgtctttg tctgatgggc    2700
tcatccgttt gtgcgcagac gggtcgtcct tggtgggaaa caaccccttg gctgcttctc    2760
ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag cataggcttc    2940
ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga aagaacatgt gagcaaaagg ccagcaaaag gccaggaacc    3180
gtaaaaaggc cgcgttgctg gcgttttttcc ataggctccg ccccccctgac gagcatcaca    3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc aacccggta agacacgact    3540 tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt tgtttgcaa gcagcagatt acgcgcagaa    3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
```

```
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta ccgcctcca     4200 tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca acacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
cgacacggaa atgttgaata ctcatactct tcctttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgct taattaatcg cgatggccac atatggagct ctctagaaaa caatatattt    5100
ccaaatgaaa aaaaaatctg ataaaaagtt gactttaaaa aagtatcaat aaatgtatgc    5160
atttctcact agccttaaac tctgcatgaa gtgtttgatg agcagatgaa gacaacatca    5220
tttctagttt cagaaataat aacagcatca aaaccgcagc tgtaactcca ctgagctcac    5280
gttaagtttt gatgtctgaa tatctgacag aactgacata atgagcactg caaggatatc    5340
agacaagtca aaatgaagac agacaaaagt attttttaat ataaaaatgg tcttatttc     5400 ttcaatacaa ggtaaactac tattgcagtt taagaccaac acaaaagttg dacagcaaat    5460
tgcttaacag tctcctaaag gctgaaaaaa aggaacccat gaaagctaaa agttatgcag    5520
tatttcaagt ataacatcta aaaatgatga aacgatccct aaaggtagag attaactaag    5580
tacttctgct gaaaatgtat taaaatccgc agttgctagg ataccatctt accttgttga    5640
gaaatacagg tctccggcaa cgcaacattc agcagactct ttggcctgct ggaatcagga    5700
aactgcttac tatatacaca tataaaatcc tttggagttg ggcattctga gagacatcca    5760
tttcctgaca ttttgcagtg caactctgca ttccaactca gacaagctcc catgctgtat    5820
ttcaaagcca tttcttgaat agtttaccca gacatccttg tgcaaattgg gaatgaggaa    5880
atgcaatggt acaggaagac aatacagcct tatgtttaga aagtcagcag cgctggtaat    5940
cttcataaaa atgtaactgt ttaccaaata ggaatgtatt tcacttgtaa aacacctggt    6000 ccttttata ttacttttt tttttttaa ggacacctgc actaatttgc aatcacttgt       6060
atttataaaa gcacacgcac tcctcatttt cttacatttg aagatcagca gaatgtctct    6120
ttcataatgt aataatcata tgcacagttt aaaatatttt ctattacaaa atacagtaca    6180
caagagggtg aggccaaagt ctattacttg aatatattcc aaagtgtcag cactggggt     6240 gtaaaattac attacatggt atgaataggc ggaattcttt tacaactgaa atgctcgatt    6300
tcattgggat caaaggtaag tactgtttac tatcttcaag agacttcaat caagtcagtg    6360
```

```
tatttccaaa gaagcttaaa agattgaagc acagacacag gccacaccag agcctacacc    6420
tgctgcaata agtggtgcta tagaaaggat tcaggaacta caagtgcat aatttacaaa    6480
tagagatgct ttatcatact ttgcccaaca tgggaaaaaa gacatcccat gagaatatcc    6540
aactgaggaa cttctctgtt tcatagtaac tcatctacta ctgctaagat ggtttgaaaa    6600
gtacccagca ggtgagatgt gttccgggag gtggctgtgt ggcagcgtgt gggaacacga    6660
cacaaagcac cccaccccta tctgcaaatc gctcactgca aggcagtgcc gtaaacagct    6720
gcaacaggca tcacttctgc ataaatgctg tgactcgtta gcatgctgca actgtgttta    6780
aaacctatgc actccgttac caaaataatt taagtcccaa acaaatccat gcagcttgct    6840
tcctatgcca aaatatttta gaaagtattc attcttcttt aagaatatgc acgtggatct    6900
acacttccct gggatctgaa gcgatttata cctcagtgca gaagcagttt agtgtcctgg    6960
atctcgggaa ggcagcagcc aaacgtgccc gttttacatt tgaacccatg tgacaacccg    7020
ccttactgag catcgctcta ggaaatttaa ggctgtatcc ttacaacaca agaaccaacg    7080
acagactgca tataaaattc tataaataaa aataggagtg aagtctgttt gacctgtaca    7140
cacagagcat agagataaaa aaaaaaggaa atcaggaatt acgtatttct ataaatgcca    7200
tatattttta ctagaaacac agatgacaag tatatacaac atgtaaatcc gaagttatca    7260
acatgttaac taggaaaaca tttacaagca tttgggtatg caactagatc atcaggtaaa    7320
aaatcccatt agaaaaatct aagcctcgcc agtttcaaag gaaaaaacc agagaacgct    7380
cactacttca aagggaaaaa aataaagcat caagctggcc taaacttaat aaggtatctc    7440
atgtaacaac agctatccaa gctttcaagc cacactataa ataaaaacct caagttccga    7500
tcaacgtttt ccataatgca aatcagaacc aaaggcattg gcacagaaag caaaaaggga    7560
atgaaagaaa agggctgtac agtttccaaa aggttcttct tttgaagaaa tgtttctgac    7620
ctgtcaaaac atacagtcca gtagaaattt tactaagaaa aaagaacacc ttacttaaaa    7680
aaaaaaaaca acaaaaaaaa caggcaaaaa aacctctcct gtcactgagc tgccaccacc    7740
ccaaccacca cctgctgtgg gctttgtctc ccaagacaaa ggacacacag ccttatccaa    7800
tattcaacat tacttataaa aacgctgatc agaagaaata ccaagtattt cctcacagac    7860
tgttatatcc tttcatcggc aagaagagat gaaatacaac agagtgaata tcaaagaagg    7920
cggcaggagc caccgtggca ccatcaccgg gcagtgcagt gcccaactgc cgtttcctga    7980
gcacgcacag gaagccgtca gtcacatgta ataaaccaaa acctggtaca attgtattac    8040
ggatcccggt ggcgcgccgt ttaaaccctc agctaccgat gtacgggcca gatatacgcg    8100
ttgacattga ttattgacta gttattaata gtaatcaatt acggggtcat tagttcatag    8160
cccatatatg gagttccgcg ttacataact tacggtaaat ggcccgcctg gctgaccgcc    8220
caacgacccc cgcccattga cgtcaataat gacgtatgtt cccatagtaa cgccaatagg    8280
gactttccat tgacgtcaat gggtggacta tttacggtaa actgcccact ggcagtacat    8340
caagtgtat catatgccaa gtacgccccc tattgacgtc aatgacggta aatggcccgc    8400
ctggcattat gcccagtaca tgaccttatg ggactttcct acttggcagt acatctacgt    8460
attagtcatc gctattacca tggtgatgcg gttttggcag tacatcaatg ggcgtggata    8520
gcggtttgac tcacggggat ttccaagtct ccaccccatt gacgtcaatg ggagtttgtt    8580
ttggcaccaa aatcaacggg actttccaaa atgtcgtaac aactccgccc cattgacgca    8640
aatgggcggt aggcgtgtac ggtgggaggt ctatataagc agagctctct ggctaactag    8700
agaacccact gcttactggc ttatcgaaat taatacgact cactataggca attgcacgtg    8760
```

```
tggccacagg taagtttaaa gctcaggtcg agaccgggcc tttgtccggc gctcccttgg    8820
agcctaccta gactcagccg gctctccacg ctttgcctga ccctgcttgc tcaactctac    8880
gtctttgttt cgttttctgt tcctttctct ccacaggctt aagcttggta ccagaaagtt    8940
aacatggctg tcttggggct gctcttctgc ctggtgacat tcccaagctg tgtcctatcc    9000
caggtgcagc tggtggagtc tgggggaggc gtggtccagc ctgggaggtc cctgagactc    9060
tcctgtgcag cctctggatt cactttcagt gactatcata tggcctgggt ccgccaggct    9120
ccaggcaagg ggctggagtg ggtggcaagc attactcttg atgctaccta cacttactat    9180
cgcgactccg tgcgcggccg cttccaccatc tccagagaca attccaagaa cacgctgtat    9240
ctgcaaatga acagcctgag agctgaggac acggctgtgt attactgtgc gagacatcga    9300
ggctttagcg tctggcttga ttactggggc caaggcaccc tggtcaccgt ctcgtcggct    9360
agcaccaagg gcccatcggt cttccccctg gcaccctcct ccaagagcac ctctgggggc    9420
acagcggccc tgggctgcct ggtcaaggac tacttccccg aaccggtgac ggtgtcgtgg    9480
aactcaggcg ccctgaccag cggcgtgcac accttcccgg ctgtcctaca gtcctcagga    9540
ctctactccc tcagcagcgt ggtgaccgtg ccctccagca gcttgggcac ccagacctac    9600
atctgcaacg tgaatcacaa gcccagcaac accaaggtgg acaagaaagt tgagcccaaa    9660
tcttgtgaca aaactcacac atgcccaccg tgcccagcac ctgaactcct ggggggaccg    9720
tcagtcttcc tcttccccc aaaacccaag gacaccctca tgatctcccg gacccctgag    9780
gtcacatgcg tggtggtgga cgtgagccac gaagaccctg aggtcaagtt caactggtac    9840
gtggacggcg tggaggtgca taatgccaag acaaagccgc gggaggagca gtacaacagc    9900
acgtaccgtg tggtcagcgt cctcaccgtc ctgcaccagg actggctgaa tggcaaggag    9960
tacaagtgca aggtctccaa caaagccctc ccagccccca tcgagaaaac catctccaaa    10020 gccaagggc agccccgaga accacaggtg tacaccctgc ccccatcccg ggatgagctg    10080
accaagaacc aggtcagcct gacctgcctg gtcaaaggct tctatcccag cgacatcgcc    10140
gtggagtggg agagcaatgg gcagccggag aacaactaca agaccacgcc tcccgtgctg    10200
gactccgacg gctccttctt cctctacagc aagctcaccg tggacaagag caggtggcag    10260
caggggaacg tcttctcatg ctccgtgatg catgaggctc tgcacaacca ctacacgcag    10320
aagagcctct ccctgtctcc gggtaaatga atcgatgatt ctagatacgg gtccggagga    10380
tccagatccc cctcgctttc ttgctgtcca atttctatta aggttccttt gttccctaa     10440 gtccaactac taaactgggg gatattatga agggccttga gcatctggat tctgcctaat    10500
aaaaaacatt tattttcatt gcaatgatgt atttaaatta tttctgaata ttttactaaa    10560
aagggaatgt gggaggtcag tgcatttaaa acataaagaa atgaagaggg gatctgtcg    10620 acaagctcta gagagctcac gcgttgatca ttaatcagcc ataccacatt tgtagaggtt    10680
ttacttgctt taaaaaacct cccacacctc cccctgaacc tgaaacataa atgaatgca     10740 attgttgttg ttaacttgtt tattgcagct tataatggtt acaaataaag caatagcatc    10800
acaaatttca caaataaagc attttttca ctgcattcta gttgtggttt gtccaaactc    10860
atcaatgtat cttatcatgt ctggatcgcg gccgctctag aactagttat taatagtaat    10920
caattacggg gtcattagtt catagcccat atatggagtt ccgcgttaca taacttacgg    10980
taaatggccc gcctggctga ccgcccaacg acccccgccc attgacgtca ataatgacgt    11040
atgttcccat agtaacgcca atagggactt tccattgacg tcaatgggtg gagtatttac    11100
ggtaaactgc ccacttggca gtacatcaag tgtatcatat gccaagtacg ccccctattg    11160
```

```
acgtcaatga cggtaaatgg cccgcctggc attatgccca gtacatgacc ttatgggact   11220
ttcctacttg gcagtacatc tacgtattag tcatcgctat taccatggtg atgcggtttt   11280
ggcagtacat caatgggcgt ggatagcggt ttgactcacg gggatttcca agtctccacc   11340
ccattgacgt caatgggagt ttgttttggc accaaaatca acgggacttt ccaaaatgtc   11400
gtaacaactc cgccccattg acgcaaatgg gcggtaggcg tgtacggtgg gaggtctata   11460
taagcagagc tcgtttagtg aaccgtctag acgatgaga cgccatccac gctgttttga   11520
cctccataga agacaccggg accgatccag cctccgcggc cgggaacggt gcattggaac   11580
gcggattccc cgtgccaaga gtgacgtaag taccgcctat agagtctata ggcccacccc   11640
cttggcttct tatgcatgct cccctgctcc gacccgggct cctcgcccgc ccggacccac   11700
aggccaccct caaccgtcct ggccccggac ccaaacccca cccctcactc tgcttctccc   11760
cgcaggagaa ttcgagatcc cggtgccgcc accatcccct gacccacgcc cctgacccct   11820
cacaaggaga cgaccttcca tgaccgagta caagcccacg gtgcgcctcg ccacccgcga   11880
cgacgtcccc cgggccgtac gcaccctcgc cgccgcgttc gccgactacc cgccacgcg   11940 ccacaccgtc gacccggacc gccacatcga gcgggtcacc gagctgcaag aactcttcct   12000
cacgcgcgtc gggctcgaca tcggcaaggt gtgggtcgcg gacgacggcg ccgcggtggc   12060
ggtctggacc acgccggaga gcgtcgaagc ggggcggtg ttcgccgaga tcggcccgcg   12120
catggccgag ttgagcggtt cccggctggc cgcgcagcaa cagatggaag gcctcctggc   12180
gccgcaccgg cccaaggagc ccgcgtggtt cctggccacc gtcggcgtct cgcccgacca   12240
ccagggcaag ggtctgggca gcgccgtcgt gctccccgga gtggaggcgg ccgagcgcgc   12300
cggggtgccc gccttcctgg agacctccgc gccccgcaac ctccccttct acgagcggct   12360
cggcttcacc gtcaccgccg acgtcgagtg cccgaaggac cgcgcgacct ggtgcatgac   12420
ccgcaagccc ggtgcctgac gcccgcccca cgacccgcag cgcccgaccg aaaggagcgc   12480 acgacccat ggctccgacc gaagccgacc cgggcggccc cgccgacccc gcacccgccc   12540
ccgaggccca ccgactctag aggatcataa tcagccatac cacatttgta gaggttttac   12600
ttgctttaaa aaacctccca cacctccccc tgaacctgaa acataaaatg aatgcaattg   12660
ttgttgttaa cttgtttatt gcagcttata atggttacaa ataaagcaat agcatcacaa   12720
atttcacaaa taaagcattt ttttcactgc attctagttg tggtttgtcc aaactcatca   12780
atgtatctta tcatgtctgg ctctagctat cccgccccta actccgccca gttccgccca   12840
ttctccgccc catggctgac taatttttt tatttatgca gaggccgagg ccgcctggag   12900
ttaattaatc gcgatggcca catatggagc tctctagagc ttgtcgacag atccccctct   12960
tcatttcttt atgttttaaa tgcactgacc tcccacattc cctttttagt aaaatattca   13020
gaaataattt aaatacatca ttgcaatgaa aataaatgtt tttattagg cagaatccag   13080 atgctcaagg cccttcataa tatccccag tttagtagtt ggacttaggg aacaaaggaa   13140 ccttaatag aaattggaca gcaagaaagc gaggggatc tggatcctcc ggagggccct   13200
ggatcctcct acgtatctag aatcatcgat taacactctc ccctgttgaa gctctttgtg   13260
acgggcgagc tcaggccctg atgggtgact tcgcaggcgt agactttgtg tttctcgtag   13320
tctgctttgc tcagcgtcag ggtgctgctg aggctgtagg tgctgtcctt gctgtcctgc   13380
tctgtgacac tctcctggga gttacccgat tggagggcgt tatccacctt ccactgtact   13440
ttggcctctc tgggatagaa gttattcagc aggcacacaa cagaggcagt tccagatttc   13500
aactgctcat cagatggcgg gaagatgaag acagatggtg cagccaccgt acgtttcagt   13560
```

-continued

```
tccagcttgg tcccaggtcc aaacgtgtac ccgctataat actggtgaca gtagtaagtt     13620
gcaaaatctt caggttgcag actgctgatg gtgagagtga atctgtccc agatccactg      13680 ccactgaacc ttgatgggac ccccgcttgc aaagggcttg cattatagat caggagctta    13740
ggggctttcc ctggtttctg ctgataccag gccaagttct caaaaatgtt ctgacttgtc    13800
ttgcaagtga tggtgactct gtctcctaca gatgcagaca gggaggatgg agactgggtc    13860
atctggatgt cacatctcat ggctgggagg aagagcacca aaagccctaa aagttgaact    13920
ggagccatct cgagaattct taagcctgtg gagagaaagg aacagaaaac gaaacaaaga    13980
cgtagagttg agcaagcagg gtcaggcaaa gcgtggagag ccggctgagt ctaggtaggc    14040
tccaagggag cgccggacaa aggcccggtc tcgacctgag ctttaaactt acctgtggcc    14100
acacgtgcaa ttgctatagt gagtcgtatt aatttcgata agccagtaag cagtgggttc    14160
tctagttagc cagagagctc tgcttatata gacctcccac cgtacacgcc taccgcccat    14220
ttgcgtcaat ggggcggagt tgttacgaca ttttggaaag tcccgttgat tttggtgcca    14280
aaacaaactc ccattgacgt caatggggtg gagacttgga atccccgtg agtcaaaccg     14340 ctatccacgc ccattgatgt actgccaaaa ccgcatcacc atggtaatag cgatgactaa    14400
tacgtagatg tactgccaag taggaaagtc ccataaggtc atgtactggg cataatgcca    14460
ggcgggccat ttaccgtcat tgacgtcaat agggggcgta cttggcatat gatacacttg    14520
atgtactgcc aagtgggcag tttaccgtaa atagtccacc cattgacgtc aatggaaagt    14580
ccctattggc gttactatgg gaacatacgt cattattgac gtcaatgggc ggggtcgtt     14640 gggcggtcag ccaggcgggc catttaccgt aagttatgta acgcggaact ccatatatgg    14700
gctatgaact aatgacccc taattgatta ctattaataa ctagtcaata atcaatgtca     14760
acgcgtatat ctggcccgta catcggtaac tagtcggacc ggcccgggcc accggtgctc    14820
gaagcttgga tcgatccaga catgataaga tacattgatg agtttggaca aaccacaact    14880
agaatgcagt gaaaaaaatg ctttatttgt gaaatttgtg atgctattgc ttatttgta    14940 accattataa gctgcaataa acaagttaac aacaacaatt gcattcattt tatgtttcag    15000 gttcagggg aggtgtggga ggttttttaa agcaagtaaa acctctacaa atgtggtatg     15060
gctgattatg atctctagtc aag                                             15083
```

<210> SEQ ID NO 26
<211> LENGTH: 14937
<212> TYPE: DNA
<213> ORGANISM: Artificial Sequence
<220> FEATURE:
<223> OTHER INFORMATION: Nucleotide sequence of pAIGFRLCb2/MAR(-)

<400> SEQUENCE: 26

```
gcactataca tcaaatattc cttattaacc cctttacaaa ttaaaaagct aaaggtacac         60 aattttttgag catagttatt aatagcagac actctatgcc tgtgtggagt aagaaaaaac       120
agtatgttat gattataact gttatgccta cttataaagg ttacagaata ttttttccata      180 atttttcttgt atagcagtgc agcttttttcc tttgtggtgt aaatagcaaa gcaagcaaga      240
gttctattac taaacacagc atgactcaaa aaacttagca attctgaagg aaagtccttg       300
gggtcttcta cctttctctt ctttttttgga ggagtagaat gttgagagtc agcagtagcc       360
tcatcatcac tagatggcat tcttctgag caaaacaggt tttcctcatt aaaggcattc         420
caccactgct cccattcatc agttccatag gttggaatct aaaatacaca acaattaga         480 atcagtagtt taacacatta tacacttaaa aattttatat ttaccttaga gctttaaatc        540
```

-continued

```
tctgtaggta gtttgtccaa ttatgtcaca ccacagaagt aaggttcctt cacaaagatc      600
gatctaaagc cagcaaaagt cccatggtct tataaaaatg catagcttta ggaggggagc      660
agagaacttg aaagcatctt cctgttagtc tttcttctcg tagacttcaa acttatactt      720
gatgcctttt tcctcctgga cctcagagag gacgcctggg tattctggga gaagtttata      780
tttccccaaa tcaatttctg ggaaaaacgt gtcactttca aattcctgca tgatccttgt      840
cacaaagagt ctgaggtggc ctggttgatt catggcttcc tggtaaacag aactgcctcc      900
gactatccaa accatgtcta ctttacttgc caattccggt tgttcaataa gtcttaaggc      960
atcatccaaa cttttggcaa gaaaatgagc tcctcgtggt ggttctttga gttctctact     1020
gagaactata ttaattctgt cctttaaagg tcgattcttc tcaggaatgg agaaccaggt     1080
tttcctaccc ataatcacca gattctgttt accttccact gaagaggttg tggtcattct     1140
ttggaagtac ttgaactcgt tcctgagcgg aggccagggt aggtctccgt tcttgccaat     1200
ccccatattt tgggacacgg cgacgatgca gttcaatggt cgaaccatga tggcagcggg     1260
gataaaatcc taccagcctt cacgctagga ttgccgtcaa gtttggcgcg aaatcgcagc     1320
cctgagctgt ccccccccc aagctcagat ctgagcttgg tccctatggt gagtccgttc     1380
cgctcttgtg atgatagcca gacaagaaag agacaataca agacaaacac caaatagtag     1440
aaatagagac aagggtcact tatccgaggg tccctgttcg ggcgccagct gccgcagtcg     1500
gccgacctga gggtcgccgg ggtctgcggg gggaccctct ggaaagtgaa ggataagtga     1560
cgagcggaga cgggatggcg aacagacaca aacacacaag aggtgaatgt taggactgtt     1620
gcaagtttac tcaaaaaatc agcactcttt tatatcttgg tttacataag catttacata     1680
agatttggat aaattccaaa agaacatagg aaaatagaac actcagagct cagatcagaa     1740
cctttgatac caaaccaagt caggaaacca cttgtctcac atcctcgttt taagaacagt     1800
ttgtaaccaa aaacttactt aagccctggg aaccgcaagg ttgggccaat aaaggctatt     1860
cataataact catgccatga gtttttgcag aataatgttc tattagtcca gccactgtcc     1920
cctccttggt atggaaaatc tttccccaaa agtgcattcc tgttcctaga taaatataat     1980
catgtacctg ttgtttcatg tcgtcttttt cttcttgaga caacatacac caaggaggtc     2040
tagctctggc gagtctttca cgaaagggga gggatctata taacacttta tagccattga     2100
ctgtaaccca cctatcccaa tttaagtcat atcttcctgt atatggtaag ggggcatctg     2160
ttggtctgta gatgtaaggt cccctataag tccctggttg ccaccacctg tctcctatt     2220 tgacaaaaac actctttttt ccctttttta cttctaggcc tgtggtcaat agtccttgca     2280
cctgttcttc aattgaggtt gagcgtctct ttctatttc tattcccatt ctaacttct     2340 gaatttgagt aaaaatagta ctaaaagata atgattcatt tcttaacata gtaactaata     2400
atctacctat tggattggtc ttattggtaa aaatataatt tttagcaagc attcttattt     2460
ctatttctga aggacaaaat cgatgcggct tgtaagagga agttggctgt ggtccttgcc     2520
tcaggaggaa ggtcgagttc tccgaattgt ttagattgta atcttgcaca gaagagctat     2580
taaaagagtc aagggtgaga gccctgcgag cacgaaccgc aacttccccc aatagcccca     2640
ggcaaagcag agctatgcca agtttgcagc agagaatgaa tatgtctttg tctgatgggc     2700
tcatccgttt gtgcgcagac gggtcgtcct tggtgggaaa caaccccttg gctgcttctc     2760
ccctaggtgt aggacactct cgggagttca accatttctg cccaagctca gatctgagct     2820
ttaatgcggt agtttatcac agttaaattg ctaacgcagt caggcaccgt gtatgaaatc     2880
taacaatgcg ctcatcgtca tcctcggcac cgtcaccctg gatgctgtag gcataggctt     2940
```

```
ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga agaacatgt gagcaaaagg ccagcaaaag gccaggaacc    3180
gtaaaaaggc cgcgttgctg gcgttttcc ataggctccg cccccctgac gagcatcaca    3240
aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc caacccggta agacacgact    3540
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt ttgtttgcaa gcagcagatt acgcgcagaa    3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca acacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
cgacacggaa atgttgaata ctcatactct tcctttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgct taattaatcg cgatggccac atatggagct ctctagaaaa caatatattt    5100
ccaaatgaaa aaaaaatctg ataaaaagtt gactttaaaa aagtatcaat aaatgtatgc    5160
atttctcact agccttaaac tctgcatgaa gtgtttgatg agcagatgaa gacaacatca    5220
tttctagttt cagaaataat aacagcatca aaaccgcagc tgtaactcca ctgagctcac    5280
gttaagtttt gatgtctgaa tatctgacag aactgacata atgagcactg caaggatatc    5340
```

```
agacaagtca aaatgaagac agacaaaagt attttttaat ataaaatgg tctttatttc    5400 ttcaatacaa ggtaaactac tattgcagtt taagaccaac acaaaagttg gacagcaaat    5460
tgcttaacag tctcctaaag gctgaaaaaa aggaacccat gaaagctaaa agttatgcag    5520
tatttcaagt ataacatcta aaaatgatga aacgatccct aaaggtagag attaactaag    5580
tacttctgct gaaaatgtat taaaatccgc agttgctagg ataccatctt accttgttga    5640
gaaatacagg tctccggcaa cgcaacattc agcagactct ttggcctgct ggaatcagga    5700
aactgcttac tatatacaca tataaaatcc tttggagttg gcattctga gagacatcca    5760 tttcctgaca ttttgcagtg caactctgca ttccaactca gacaagctcc catgctgtat    5820
ttcaaagcca tttcttgaat agtttaccca gacatccttg tgcaaattgg gaatgaggaa    5880
atgcaatggt acaggaagac aatacagcct tatgtttaga aagtcagcag cgctggtaat    5940
cttcataaaa atgtaactgt ttaccaaata ggaatgtatt tcacttgtaa acacctggt    6000 cctttttata ttactttttt tttttttaa ggacacctgc actaatttgc aatcacttgt    6060
atttataaaa gcacacgcac tcctcatttt cttacatttg aagatcagca gaatgtctct    6120
ttcataatgt aataatcata tgcacagttt aaaatatttt ctattacaaa atacagtaca    6180
caagagggtg aggccaaagt ctattacttg aatatattcc aaagtgtcag cactgggggt    6240
gtaaaattac attcatggt atgaataggc ggaattcttt tacaactgaa atgctcgatt    6300
tcattgggat caaggtaag tactgtttac tatcttcaag agacttcaat caagtcagtg    6360
tatttccaaa gaagcttaaa agattgaagc acagacacag gccacaccag agcctacacc    6420
tgctgcaata agtggtgcta tagaaaggat tcaggaacta acaagtgcat aatttacaaa    6480
tagagatgct ttatcatact ttgcccaaca tgggaaaaaa gacatcccat gagaatatcc    6540
aactgaggaa cttctctgtt tcatagtaac tcatctacta ctgctaagat ggtttgaaaa    6600
gtacccagca ggtgagatgt gttccggag gtggctgtgt ggcagcgtgt gggaacacga    6660
cacaaagcac cccaccccta tctgcaaatc gctcactgca aggcagtgcc gtaaacagct    6720
gcaacaggca tcacttctgc ataaatgctg tgactcgtta gcatgctgca actgtgttta    6780
aaacctatgc actccgttac caaaataatt taagtcccaa acaaatccat gcagcttgct    6840
tcctatgcca aaatattta gaagtattc attcttcttt aagaatatgc acgtggatct    6900
acacttccct gggatctgaa gcgatttata cctcagtgca gaagcagttt agtgtcctgg    6960
atctcgggaa ggcagcagcc aaacgtgccc gttttacatt tgaacccatg tgacaacccg    7020
ccttactgag catcgctcta ggaaattaa ggctgtatcc ttcaacaca gaaccaacg    7080 acagactgca tataaaattc tataaataaa aataggagtg aagtctgttt gacctgtaca    7140
cacagagcat agagataaaa aaaaaggaa atcaggaatt acgtatttct ataaatgcca    7200 tatatttta ctagaaacac agatgacaag tatatacaac atgtaaatcc gaagttatca    7260
acatgttaac taggaaaaca tttacaagca tttgggtatg caactagatc atcaggtaaa    7320
aaatcccatt agaaaaatct aagcctcgcc agtttcaaag gaaaaaaacc agagaacgct    7380
cactacttca aagggaaaaa aataaagcat caagctggcc taaacttaat aaggtatctc    7440
atgtaacaac agctatccaa gctttcaagc cacactataa ataaaaacct caagttccga    7500
tcaacgtttt ccataatgca aatcagaacc aaaggcattg gcacagaaag caaaagggga    7560
atgaaagaaa agggctgtac agtttccaaa aggttcttct tttgaagaaa tgtttctgac    7620
ctgtcaaaac atacagtcca gtagaaattt tactaagaaa aaagaacacc ttacttaaaa    7680
aaaaaaaaca acaaaaaaaa caggcaaaaa aacctctcct gtcactgagc tgccaccacc    7740
```

```
ccaaccacca cctgctgtgg gctttgtctc caagacaaa ggacacacag ccttatccaa    7800
tattcaacat tacttataaa aacgctgatc agaagaaata ccaagtattt cctcacagac    7860
tgttatatcc tttcatcggc aagaagagat gaaatacaac agagtgaata tcaaagaagg    7920
cggcaggagc caccgtggca ccatcaccgg gcagtgcagt gcccaactgc cgtttcctga    7980
gcacgcacag gaagccgtca gtcacatgta ataaaccaaa acctggtaca attgtattac    8040
ggatcccggt ggcgcgccgt ttaaaccctc agctaccgat gtacgggcca gatatacgcg    8100
ttgacattga ttattgacta gttattaata gtaatcaatt acggggtcat tagttcatag    8160
cccatatatg gagttccgcg ttacataact tacggtaaat ggcccgcctg gctgaccgcc    8220
caacgacccc cgcccattga cgtcaataat gacgtatgtt cccatagtaa cgccaatagg    8280
gactttccat tgacgtcaat gggtggacta tttacggtaa actgcccact tggcagtaca    8340
tcaagtgtat catatgccaa gtacgccccc tattgacgtc aatgacggta atgggcccgc    8400
ctggcattat gcccagtaca tgaccttatg gactttcct acttggcagt acatctacgt     8460
attagtcatc gctattacca tggtgatgcg gttttggcag tacatcaatg ggcgtggata    8520
gcggtttgac tcacggggat ttccaagtct ccaccccatt gacgtcaatg ggagtttgtt    8580
ttggcaccaa aatcaacggg actttccaaa atgtcgtaac aactccgccc cattgacgca    8640
aatgggcggt aggcgtgtac ggtgggaggt ctatataagc agagctctct ggctaactag    8700
agaacccact gcttactggc ttatcgaaat taatacgact cactatagca attgcacgtg    8760
tggccacagg taagttttaaa gctcaggtcg agaccgggcc tttgtccggc gctcccttgg    8820
agcctaccta gactcagccg gctctccacg cttttgcctga ccctgcttgc tcaactctac    8880
gtctttgttt cgttttctgt tccttttctct ccacaggctt aagcttggta ccgagctcgg    8940
atccactagt ccagtgtggt ggaattcgcc cttatggagt ttgggctgag ctgggttttc    9000
cttgttgcta tattaaaagg tgtccagtgt gaggttcagc tggtgcagtc tggggaggc    9060
ttggtaaagc ctgggggtc cctgagactc tcctgtgcag cctctggatt caccttcagt    9120
agctttgcta tgcactgggt tcgccaggct ccaggaaaag gtctggagtg gatatcagtt    9180
attgatactg tggtgccac atactatgca gactccgtga agggccgatt caccatctcc    9240
agagacaatg ccaagaactc cttgtatctt caaatgaaca gcctgagagc cgaggacact    9300
gctgtgtatt actgtgcaag actggggaac ttctactacg gtatggacgt ctggggccaa    9360
gggaccacgg tcaccgtctc ctcagcttcc accaagggcc catcggtctt cccctggca    9420
ccctcctcca agagcacctc tgggggcaca gcggccctgg gctgcctggt caaggactac    9480
ttccccgaac cggtgacggt gtcgtggaac tcaggcgccc tgaccagcgg cgtgcacacc    9540
ttcccggctg tcctacagtc ctcaggactc tactccctca gcagcgtggt gaccgtgccc    9600
tccagcagct gggcaccca gacctacatc tgcaacgtga atcacaagcc cagcaacacc    9660
aaggtggaca gaaagttga gcccaaatct tgtgacaaaa ctcacacatg cccaccgtgc    9720
ccagcacctg aactcctggg gggaccgtca gtcttcctct tccccccaaa acccaaggac    9780
accctcatga tctcccggac ccctgaggtc acatgcgtgg tggtggacgt gagccacgaa    9840
gaccctgagg tcaagttcaa ctggtacgtg gacggcgtgg aggtgcataa tgccaagaca    9900
aagccgcggg aggagcagta caacagcacg taccgtgtgg tcagcgtcct caccgtcctg    9960
caccaggact ggctgaatgg caaggagtac aagtgcaagg tctccaacaa agccctccca   10020
gcccccatcg agaaaccat ctccaaagcc aagggcagc cccgagaacc acaggtgtac    10080
accctgcccc catcccggga tgagctgacc aagaaccagg tcagcctgac ctgcctggtc    10140
```

```
aaaggcttct atcccagcga catcgccgtg gagtgggaga gcaatgggca gccggagaac   10200
aactacaaga ccacgcctcc cgtgctggac tccgacggct ccttcttcct ctacagcaag   10260
ctcaccgtgg acaagagcag gtggcagcag gggaacgtct tctcatgctc cgtgatgcat   10320
gaggctctgc acaaccacta cacgcagaag agcctctccc tgtctccggg taaatgaatc   10380
gatgattcta gatacgggtc cggaggatcc agatccccct cgctttcttg ctgtccaatt   10440
tctattaaag gttcctttgt tccctaagtc caactactaa actgggggat attatgaagg   10500
gccttgagca tctggattct gcctaataaa aaacatttat tttcattgca atgatgtatt   10560
taaattattt ctgaatattt tactaaaaag gaatgtggg aggtcagtgc atttaaaaca    10620
taaagaaatg aagaggggga tctgtcgaca agctctagag agctcacgcg ttgatcatgt   10680
acaggccggc caagctttcg actagcttgg cacgccagaa atccgcgcgg tggttttgg    10740 gggtcggggg tgtttggcag ccacagacgc ccggtgttcg tgtcgcgcca gtacatgcgg   10800
tccatgccca ggccatccaa aaaccatggg tctgtctgct cagtccagtc gtggacctga   10860
ccccacgcaa cgcccaaaat aataacccccc acgaaccata aaccattccc catgggggac   10920
cccgtcccta acccacgggg ccagtggcta tggcagggcc tgccgccccg acgttggctg   10980
cgagccctgg gccttcaccc gaacttgggg ggtgggggtgg ggaaaaggaa gaaacgcggg  11040
cgtattggcc ccaatgggt  tcggtgggg  tatcgacaga gtgccagccc tgggaccgaa   11100
ccccgcgttt atgaacaaac gacccaacac ccgtgcgttt tattctgtct ttttattgcc   11160
gtcatagcgc gggttccttc cggtattgtc tccttccgtg tttcagttag cctccccccat 11220 ctcccgatcc ggacgagtgc tggggcgtcg gtttccacta tcggcgagta cttctacaca   11280
gccatcggtc cagacggccg cgcttctgcg ggcgatttgt gtacgcccga cagtcccggc   11340
tccggatcgg acgattgcgt cgcatcgacc ctgcgcccaa gctgcatcat cgaaattgcc   11400
gtcaaccaag ctctgataga gttggtcaag accaatgcgg agcatatacg cccggagccg   11460
cggcgatcct gcaagctccg gatgcctccg ctcgaagtag cgcgtctgct gctccataca   11520
agccaaccac ggcctccaga agaagatgtt ggcgacctcg tattgggaat ccccgaacat   11580
cgcctcgctc cagtcaatga ccgctgttat gcggccattg tccgtcagga cattgttgga   11640
gccgaaatcc gcgtgcacga ggtgccggac ttcggggcag tcctcggccc aaagcatcag   11700
ctcatcgaga gcctgcgcga cggacgcact gacggtgtcg tccatcacag tttgccagtg   11760
atacacatgg ggatcagcaa tcgcgcatat gaaatcacgc catgtagtgt attgaccgat   11820
tccttgcggt ccgaatgggc cgaacccgct cgtctggcta agatcggccg cagcgatcgc   11880
atccatggcc tccgcgaccg gctgcagaac agcgggcagt tcggtttcag gcaggtcttg   11940
caacgtgaca ccctgtgcac ggcgggagat gcaataggtc aggctctcgc tgaattcccc   12000
aatgtcaagc acttccggaa tcgggagcgc ggccgatgca aagtgccgat aaacataacg   12060
atctttgtag aaaccatcgg cgcagctatt tacccgcagg acatatccac gccctcctac   12120
atcgaagctg aaagcacgag attcttcgcc ctccgagagc tgcatcaggt cggagacgct   12180
gtcgaacttt tcgatcagaa acttctcgac agacgtcgcg gtgagttcag cttttttcat   12240
atctcattgc cccccgggat ctgcggcacg ctgttgacgc tgttaagcgg gtcgctgcag   12300
ggtcgctcgg tgttcgaggc cacacgcgtc accttaatat gcgaagtgga cctcggaccg   12360
cgccgccccg actgcatctg cgtgttcgaa ttcgccaatg acaagacgct gggcggggtt   12420
tgtgtcatca tagaactaaa gacatgcaaa tatatttctt ccggggacac cgccagcaaa   12480
cgcgagcaac gggccacggg gatgaagcag ggcggcacct cgctaacgga ttcaccactc   12540
```

```
caagaattgg agccaatcaa ttcttgcgga gaactgtgaa tgcgcaaacc aacccttggc   12600
agaacatatc catcgcgtcc gccatctcca gcagccgcac gcggcgcatc tcggggccga   12660
cgcgctgggc tacgtcttgc tggcgttcgc acaggccggc cagcgcgcgg ccggccggta   12720
ccacgcgttg gccacatatg gcggccgctc gcgattaatt aatcgcgatg ccacatatg    12780 gagctctcta gagcttgtcg acagatcccc ctcttcattt ctttatgttt taaatgcact   12840
gacctcccac attcccttt tagtaaaata ttcagaaata atttaaatac atcattgcaa    12900
tgaaaataaa tgttttttat taggcagaat ccagatgctc aaggcccttc ataatatccc   12960
ccagtttagt agttggactt agggaacaaa ggaaccttta atagaaattg acagcaaga    13020 aagcgagggg gatctggatc ctccggaggg cccccttctcc ctctaacact ctcccctgtt  13080
gaagctcttt gtgacgggcg agctcaggcc ctgatgggtg acttcgcagg cgtagacttt   13140
gtgtttctcg tagtctgctt tgctcagcgt cagggtgctg ctgaggctgt aggtgctgtc   13200
cttgctgtcc tgctctgtga cactctcctg ggagttaccc gattggaggg cgttatccac   13260
cttccactgt actttggcct ctctgggata gaagttattc agcaggcaca caacagaggc   13320
agttccagat ttcaactgct catcagatgg cgggaagatg aagacagatg gtgcagccac   13380
tgtacgtttg atctccacct tggtcccttg gccgaaagtg tgaggtaaac gactactctg   13440
atgacagtaa tacactgcga aatcttcagg ctccagtcta ctgatggtga gggtgaaatc   13500
tgtcccagat ccactgccac tgaacctatc ggggatccct gagagggact gggatgcata   13560
cttgatgaga agccttggag cctgacctgg tttctgctgg taccagtgta agctactacc   13620
aatgctctga ctggcccggc aggagagggt ggctctctcg cctggagaca cagacagggt   13680
acctgggctc tgagtcagca caatttcacc cctggaggct ggaacccaga gcagcagaaa   13740
cccaatgagt tgtgatggcg acatgttaaa cgctagaatt cttaagcctg tggagagaaa   13800
ggaacagaaa acgaaacaaa gacgtagagt tgagcaagca gggtcaggca aagcgtggag   13860
agccggctga gtctaggtag gctccaaggg agcgccggac aaaggcccgg tctcgacctg   13920
agctttaaac ttacctgtgg ccacacgtgc aattgctata gtgagtcgta ttaatttcga   13980
taagccagta agcagtgggt tctctagtta gccagagagc tctgcttata tagacctccc   14040
accgtacacg cctaccgccc atttgcgtca atggggcgga gttgttacga cattttggaa   14100
agtcccgttg attttggtgc caaaacaaac tcccattgac gtcaatgggg tggagacttg   14160
gaaatccccg tgagtcaaac cgctatccac gcccattgat gtactgccaa aaccgcatca   14220
ccatggtaat agcgatgact aatacgtaga tgtactgcca agtaggaaag tcccataagg   14280
tcatgtactg gcataatgc caggcgggcc atttaccgtc attgacgtca ataggggcg    14340 tacttggcat atgatacact tgatgtactg ccaagtgggc agtttaccgt aaatagtcca   14400
cccattgacg tcaatggaaa gtccctattg gcgttactat gggaacatac gtcattattg   14460
acgtcaatgg gcgggggtcg ttgggcggtc agccaggcgg gccatttacc gtaagttatg   14520
taacgcggaa ctccatatat gggctatgaa ctaatgaccc cgtaattgat tactattaat   14580
aactagtcaa taatcaatgt caacgcgtat atctggcccg tacatcggta actagtcgga   14640
ccgccgcgga ctagtgcccg ggccaccggt gctcgaagct tggatcgatc cagacatgat   14700
aagatacatt gatgagtttg gacaaaccac aactagaatg cagtgaaaaa aatgctttat   14760
ttgtgaaatt tgtgatgcta ttgctttatt tgtaaccatt ataagctgca ataaacaagt   14820
taacaacaac aattgcattc attttatgtt tcaggttcag ggggaggtgt gggaggtttt   14880
ttaaagcaag taaaacctct acaaatgtgg tatggctgat tatgatctct agtcaag      14937
```

<210> SEQ ID NO 27
<211> LENGTH: 15110
<212> TYPE: DNA
<213> ORGANISM: Artificial Sequence
<220> FEATURE:
<223> OTHER INFORMATION: Nucleotide sequence of pAIGFRLCb2/puro/MAR(-)

<400> SEQUENCE: 27

```
gcactataca tcaaatattc cttattaacc cctttacaaa ttaaaaagct aaaggtacac      60
aattttttgag catagttatt aatagcagac actctatgcc tgtgtggagt aagaaaaaac    120
agtatgttat gattataact gttatgccta cttataaagg ttacagaata tttttccata    180
attttcttgt atagcagtgc agcttttttcc tttgtggtgt aaatagcaaa gcaagcaaga    240
gttctattac taaacacagc atgactcaaa aaacttagca attctgaagg aaagtccttg    300
gggtcttcta cctttctctt cttttttgga ggagtagaat gttgagagtc agcagtagcc    360
tcatcatcac tagatggcat ttcttctgag caaaacaggt tttcctcatt aaaggcattc    420
caccactgct cccattcatc agttccatag gttggaatct aaaatacaca aacaattaga    480
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcacttttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt cccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg ggaccctct ggaaagtgaa ggataagtga   1560
cgagcggaga cgggatggcg aacagacaca acacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gttttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacactttta tagccattga   2100
```

```
ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actcttttt  ccctttttta cttctaggcc tgtggtcaat agtccttgca    2280
cctgttcttc aattgaggtt gagcgtctct ttctattttc tattcccatt tctaacttct    2340
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaagagtc  aagggtgaga gccctgcgag cacgaaccgc aacttccccc aatagcccca    2640
ggcaaagcag agctatgcca agtttgcagc agagaatgaa tatgtctttg tctgatgggc    2700
tcatccgttt gtgcgcagac gggtcgtcct tggtgggaaa caacccttg  gctgcttctc    2760
ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag cataggctt     2940
ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga aagaacatgt gagcaaaagg ccagcaaaag gccaggaacc    3180
gtaaaaaggc cgcgttgctg gcgttttcc  ataggctccg cccccctgac gagcatcaca    3240
aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc caacccggta agacacgact    3540
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt tgtttgcaa  gcagcagatt acgcgcagaa    3780
aaaaaggatc tcaagaagat cctttgatct ttttctacgg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atccccatg  ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
```

```
tttctgtgac tggtgagtac tcaaccaagt cattctgaga atagtgtatg cggcgaccga  4560
gttgctcttg cccggcgtca acacgggata ataccgcgcc acatagcaga actttaaaag  4620
tgctcatcat tggaaaacgt tcttcggggc gaaaactctc aaggatctta ccgctgttga  4680
gatccagttc gatgtaaccc actcgtgcac ccaactgatc ttcagcatct tttactttca  4740
ccagcgtttc tgggtgagca aaaacaggaa ggcaaaatgc cgcaaaaaag gaataagggc  4800
gacacggaa atgttgaata ctcatactct ccttttttca atattattga agcatttatc  4860
agggttattg tctcatgagc ggatacatat ttgaatgtat ttagaaaaat aaacaaatag  4920
gggttccgcg cacatttccc cgaaaagtgc cacctgacgt ctaagagacc attattatca  4980
tgacattaac ctataaaaat aggcgtatca cgaggccctt tcgtcttcaa gaattgtcta  5040
gaggcgcgct taattaatcg cgatggccac atatggagct ctctagaaaa caatatattt  5100
ccaaatgaaa aaaaaatctg ataaaagtt gactttaaaa aagtatcaat aaatgtatgc  5160
atttctcact agccttaaac tctgcatgaa gtgtttgatg agcagatgaa gacaacatca  5220
tttctagttt cagaaataat aacagcatca aaaccgcagc tgtaactcca ctgagctcac  5280
gttaagtttt gatgtctgaa tatctgacag aactgacata atgagcactg caaggatatc  5340
agacaagtca aaatgaagac agacaaaagt attttttaat ataaaaatgg tctttatttc  5400
ttcaatacaa ggtaaactac tattgcagtt taagaccaac acaaaagttg gacagcaaat  5460
tgcttaacag tctcctaaag gctgaaaaaa aggaacccat gaaagctaaa agttatgcag  5520
tatttcaagt ataacatcta aaaatgatga aacgatccct aaaggtagag attaactaag  5580
tacttctgct gaaaatgtat taaaatccgc agttgctagg ataccatctt accttgttga  5640
gaaatacagg tctccggcaa cgcaacattc agcagactct ttggcctgct ggaatcagga  5700
aactgcttac tatatacaca tataaaatcc tttggagttg ggcattctga gagacatcca  5760
tttcctgaca ttttgcagtg caactctgca ttccaactca gacaagctcc catgctgtat  5820
ttcaaagcca tttcttgaat agtttaccca gacatccttg tgcaaattgg gaatgaggaa  5880
atgcaatggt acaggaagac aatacagcct tatgtttaga aagtcagcag cgctggtaat  5940
cttcataaaa atgtaactgt ttaccaaata ggaatgtatt tcacttgtaa acacctggt  6000
ccttttata ttacttttt tttttttaa ggacacctgc actaatttgc aatcacttgt  6060
atttataaaa gcacacgcac tcctcatttt cttacatttg aagatcagca gaatgtctct  6120
ttcataatgt aataatcata tgcacagttt aaaatatttt ctattacaaa atacagtaca  6180
caagagggtg aggccaaagt ctattacttg aatatattcc aaagtgtcag cactgggggt  6240
gtaaaattac attacatggt atgaataggc ggaattcttt tacaactgaa atgctcgatt  6300
tcattgggat caaggtaag tactgtttac tatcttcaag agacttcaat caagtcagtg  6360
tatttccaaa gaagcttaaa agattgaagc acagacacag gccacaccag agcctacacc  6420
tgctgcaata agtggtgcta tagaaaggat tcaggaacta acaagtgcat aatttacaaa  6480
tagagatgct ttatcatact ttgcccaaca tgggaaaaaa gacatcccat gagaatatcc  6540
aactgaggaa cttctctgtt tcatagtaac tcatctacta ctgctaagat ggtttgaaaa  6600
gtacccagca ggtgagatgt gttccgggag gtggctgtgt ggcagcgtgt gggaacacga  6660
cacaaagcac cccaccccta tctgcaaatc gctcactgca aggcagtgcc gtaaacagct  6720
gcaacaggca tcacttctgc ataaatgctg tgactcgtta gcatgctgca actgtgttta  6780
aaacctatgc actccgttac caaaataatt aagtcccaa acaaatccat gcagcttgct  6840
tcctatgcca aaatatttta gaaagtattc attcttcttt aagaatatgc acgtggatct  6900
```

```
acacttccct gggatctgaa gcgatttata cctcagtgca gaagcagttt agtgtcctgg    6960
atctcgggaa ggcagcagcc aaacgtgccc gttttacatt tgaacccatg tgacaacccg    7020
ccttactgag catcgctcta ggaaatttaa ggctgtatcc ttacaacaca agaaccaacg    7080
acagactgca tataaaattc tataaataaa aataggagtg aagtctgttt gacctgtaca    7140
cacagagcat agagataaaa aaaaaaggaa atcaggaatt acgtatttct ataaatgcca    7200 tatatttta ctagaaacac agatgacaag tatatacaac atgtaaatcc gaagttatca    7260
acatgttaac taggaaaaca tttacaagca tttgggtatg caactagatc atcaggtaaa    7320
aaatcccatt agaaaatct aagcctcgcc agtttcaaag gaaaaaaacc agagaacgct    7380
cactacttca agggaaaaa aataaagcat caagctggcc taaacttaat aaggtatctc    7440
atgtaacaac agctatccaa gctttcaagc cacactataa ataaaaacct caagttccga    7500
tcaacgtttt ccataatgca aatcagaacc aaaggcattg gcacagaaag caaaagggga    7560
atgaaagaaa agggctgtac agtttccaaa aggttcttct tttgaagaaa tgtttctgac    7620
ctgtcaaaac atacagtcca gtagaaattt tactaagaaa aaagaacacc ttacttaaaa    7680
aaaaaaaaca acaaaaaaaa caggcaaaaa aacctctcct gtcactgagc tgccaccacc    7740
ccaaccacca cctgctgtgg gctttgtctc ccaagacaaa ggacacacag ccttatccaa    7800
tattcaacat tacttataaa aacgctgatc agaagaaata ccaagtattt cctcacagac    7860
tgttatatcc tttcatcggc aagaagagat gaaatacaac agagtgaata tcaaagaagg    7920
cggcaggagc caccgtggca ccatcaccgg gcagtgcagt gcccaactgc cgtttcctga    7980
gcacgcacag gaagccgtca gtcacatgta ataaccaaa acctggtaca attgtattac    8040
ggatcccggt ggcgcgccgt ttaaaccctc agctaccgat gtacgggcca gatatacgcg    8100
ttgacattga ttattgacta gttattaata gtaatcaatt acgggtcat tagttcatag    8160 cccatatatg gagttccgcg ttacataact tacggtaaat ggcccgcctg gctgaccgcc    8220
caacgacccc cgcccattga cgtcaataat gacgtatgtt cccatagtaa cgccaatagg    8280
gactttccat tgacgtcaat gggtggacta tttacggtaa actgcccact tggcagtaca    8340
tcaagtgtat catatgccaa gtacgccccc tattgacgtc aatgacggta atggcccgc    8400 ctggcattat gcccagtaca tgaccttatg gactttcct acttggcagt acatctacgt    8460
attagtcatc gctattacca tggtgatgcg gttttggcag tacatcaatg ggcgtggata    8520
gcggtttgac tcacggggat ttccaagtct ccaccccatt gacgtcaatg ggagtttgtt    8580
ttggcaccaa aatcaacggg actttccaaa atgtcgtaac aactccgccc cattgacgca    8640
aatgggcggt aggcgtgtac ggtgggaggt ctatataagc agagctctct ggctaactag    8700
agaacccact gcttactggc ttatcgaaat taatacgact cactatagca attgcacgtg    8760
tggccacagg taagtttaaa gctcaggtcg agaccgggcc tttgtccggc gctcccttgg    8820
agcctaccta gactcagccg gctctccacg ctttgcctga ccctgcttgc tcaactctac    8880
gtctttgttt cgttttctgt tccttctct ccacaggctt aagcttggta ccgagctcgg    8940
atccactagt ccagtgtggt ggaattcgcc cttatggagt ttgggctgag ctgggttttc    9000
cttgttgcta tattaaaagg tgtccagtgt gaggttcagc tggtgcagtc tggggagc    9060 ttggtaaagc ctgggggtc cctgagactc tcctgtgcag cctctggatt cacccttcagt    9120 agctttgcta tgcactgggt tcgccaggct ccaggaaaag gtctggagtg gatatcagtt    9180
attgatactc gtggtgccac atactatgca gactccgtga agggccgatt caccatctcc    9240
agagacaatg ccaagaactc cttgtatctt caaatgaaca gcctgagagc cgaggacact    9300
```

```
gctgtgtatt actgtgcaag actggggaac ttctactacg gtatggacgt ctggggccaa    9360
gggaccacgg tcaccgtctc ctcagcttcc accaagggcc catcggtctt ccccctggca    9420
ccctcctcca agagcacctc tgggggcaca gcggccctgg gctgcctggt caaggactac    9480
ttccccgaac cggtgacggt gtcgtggaac tcaggcgccc tgaccagcgg cgtgcacacc    9540
ttcccggctg tcctacagtc ctcaggactc tactccctca gcagcgtggt gaccgtgccc    9600
tccagcagct tgggcaccca gacctacatc tgcaacgtga atcacaagcc cagcaacacc    9660
aaggtggaca agaaagttga gcccaaatct tgtgacaaaa ctcacacatg cccaccgtgc    9720
ccagcacctg aactcctggg gggaccgtca gtcttcctct tccccccaaa acccaaggac    9780
accctcatga tctcccggac ccctgaggtc acatgcgtgg tggtggacgt gagccacgaa    9840
gaccctgagg tcaagttcaa ctggtacgtg gacggcgtgg aggtgcataa tgccaagaca    9900
aagccgcggg aggagcagta caacagcacg taccgtgtgg tcagcgtcct caccgtcctg    9960
caccaggact ggctgaatgg caaggagtac aagtgcaagg tctccaacaa agccctccca    10020
gcccccatcg agaaaaccat ctccaaagcc aaagggcagc cccgagaacc acaggtgtac    10080
accctgcccc catcccggga tgagctgacc aagaaccagg tcagcctgac ctgcctggtc    10140
aaaggcttct atcccagcga catcgccgtg gagtgggaga gcaatgggca gccggagaac    10200
aactacaaga ccacgcctcc cgtgctggac tccgacggct ccttcttcct ctacagcaag    10260
ctcaccgtgg acaagagcag gtggcagcag gggaacgtct tctcatgctc cgtgatgcat    10320
gaggctctgc acaaccacta cacgcagaag agcctctccc tgtctccggg taaatgaatc    10380
gatgattcta gatacgggtc cggaggatcc agatccccct cgctttcttg ctgtccaatt    10440
tctattaaag gttcctttgt tccctaagtc caactactaa actgggggat attatgaagg    10500
gccttgagca tctggattct gcctaataaa aaacatttat tttcattgca atgatgtatt    10560
taaattattt ctgaatattt tactaaaaag ggaatgtggg aggtcagtgc atttaaaaca    10620
taaagaaatg aagaggggga tctgtcgaca agctctagag agctcacgcg ttgatcatta    10680
atcagccata ccacatttgt agaggtttta cttgctttaa aaaacctccc acacctcccc    10740
ctgaacctga aacataaaat gaatgcaatt gttgttgtta acttgtttat tgcagcttat    10800
aatggttaca aataaagcaa tagcatcaca atttcacaa ataaagcatt ttttcactg    10860 cattctagtt gtggtttgtc caaactcatc aatgtatctt atcatgtctg gatcgcggcc    10920
gctctagaac tagttattaa tagtaatcaa ttacggggtc attagttcat agcccatata    10980
tggagttccg cgttacataa cttacggtaa atggcccgcc tggctgaccg cccaacgacc    11040
cccgcccatt gacgtcaata atgacgtatg ttcccatagt aacgccaata gggactttcc    11100
attgacgtca atgggtggag tatttacggt aaactgccca cttggcagta catcaagtgt    11160
atcatatgcc aagtacgccc cctattgacg tcaatgacgg taaatggccc gcctggcatt    11220
atgcccagta catgacctta tgggactttc ctacttggca gtacatctac gtattagtca    11280
tcgctattac catggtgatg cggttttggc agtacatcaa tgggcgtgga tagcggtttg    11340
actcacggga atttccaagt ctccaccccca ttgacgtcaa tgggagtttg ttttggcacc    11400
aaaatcaacg ggactttcca aaatgtcgta acaactccgc cccattgacg caaatgggcg    11460
gtaggcgtgt acggtgggag gtctatataa gcagagctcg tttagtgaac cgtctagacg    11520
atggagacgc catccacgct gttttgacct ccatagaaga caccgggacc gatccagcct    11580
ccgcggccgg gaacggtgca ttggaacgcg gattccccgt gccaagagtg acgtaagtac    11640
cgcctataga gtctataggc ccaccccctt ggcttcttat gcatgctccc ctgctccgac    11700
```

```
ccgggctcct cgcccgcccg gacccacagg ccaccctcaa ccgtcctggc cccggaccca   11760
aaccccaccc ctcactctgc ttctccccgc aggagaattc gagatcccgg tgccgccacc   11820
atcccctgac ccacgcccct gacccctcac aaggagacga ccttccatga ccgagtacaa   11880
gcccacggtg cgcctcgcca cccgcgacga cgtcccccgg gccgtacgca ccctcgccgc   11940
cgcgttcgcc gactaccccg ccacgcgcca caccgtcgac ccggaccgcc acatcgagcg   12000
ggtcaccgag ctgcaagaac tcttcctcac gcgcgtcggg ctcgacatcg gcaaggtgtg   12060
ggtcgcggac gacggcgccg cggtggcggt ctggaccacg ccggagagcg tcgaagcggg   12120
ggcggtgttc gccgagatcg gcccgcgcat ggccgagttg agcggttccc ggctggccgc   12180
gcagcaacag atggaaggcc tcctggcgcc gcaccggccc aaggagcccg cgtggttcct   12240
ggccaccgtc ggcgtctcgc ccgaccacca gggcaagggt ctgggcagcg ccgtcgtgct   12300
ccccggagtg gaggcggccg agcgcgccgg ggtgcccgcc ttcctggaga cctccgcgcc   12360
ccgcaacctc cccttctacg agcggctcgg cttcaccgtc accgccgacg tcgagtgccc   12420
gaaggaccgc gcgacctggt gcatgacccg caagcccggt gcctgacgcc cgccccacga   12480
cccgcagcgc ccgaccgaaa ggagcgcacg accccatggc tccgaccgaa gccgacccgg   12540
gcggccccgc cgaccccgca cccgcccccg aggcccaccg actctagagg atcataatca   12600
gccataccac atttgtagag gttttacttg ctttaaaaaa cctcccacac ctcccccctga   12660 acctgaaaca taaatgaat gcaattgttg ttgttaactt gtttattgca gcttataatg   12720 gttacaata aagcaatagc atcacaaatt tcacaaataa agcattttt tcactgcatt   12780 ctagttgtgg tttgtccaaa ctcatcaatg tatcttatca tgtctggctc tagctatccc   12840
gcccctaact ccgcccagtt ccgcccattc tccgcccat ggctgactaa tttttttttat   12900 ttatgcagag gccgaggccg cctggagtta attaatcgcg atggccacat atggagctct   12960
ctagagcttg tcgacagatc cccctcttca ttttctttatg ttttaaatgc actgacctcc   13020
cacattccct ttttagtaaa atattcagaa ataatttaaa tacatcattg caatgaaaat   13080
aaatgttttt tattaggcag aatccagatg ctcaaggccc ttcataatat ccccagttt   13140 agtagttgga cttaggggaac aaaggaacct ttaatagaaa ttggacagca agaaagcgag   13200
ggggatctgg atcctccgga gggcccttc tccctctaac actctcccct gttgaagctc   13260
tttgtgacgg gcgagctcag gccctgatgg gtgacttcgc aggcgtagac tttgtgtttc   13320
tcgtagtctg cttgctcag cgtcagggtg ctgctgaggc tgtaggtgct gtccttgctg   13380
tcctgctctg tgacactctc ctgggagtta cccgattgga gggcgttatc caccttccac   13440
tgtactttgg cctctctggg atagaagtta ttcagcaggc acacaacaga ggcagttcca   13500
gatttcaact gctcatcaga tggcgggaag atgaagacag atggtgcagc cactgtacgt   13560
ttgatctcca ccttggtccc ttggccgaaa gtgtgaggta aacgactact ctgatgacag   13620
taatacactg cgaaatcttc aggctccagt ctactgatgg tgagggtgaa atctgtccca   13680
gatccactgc cactgaacct atcggggatc cctgagaggg actgggatgc atacttgatg   13740
agaagccttg gagcctgacc tggtttctgc tggtaccagt gtaagctact accaatgctc   13800
tgactggccc ggcaggagag ggtggctctc tcgcctggag acacagacag ggtacctggg   13860
ctctgagtca gcacaatttc acccctggag gctggaaccc agagcagcag aaacccaatg   13920
agttgtgatg gcgacatgtt aaacgctaga attcttaagc ctgtggagag aaaggaacag   13980
aaaacgaaac aaagacgtag agttgagcaa gcagggtcag gcaaagcgtg gagagccggc   14040
tgagtctagg taggctccaa gggagcgccg gacaaaggcc cggtctcgac ctgagcttta   14100
```

```
aacttacctg tggccacacg tgcaattgct atagtgagtc gtattaattt cgataagcca    14160
gtaagcagtg ggttctctag ttagccagag agctctgctt atatagacct cccaccgtac    14220
acgcctaccg cccatttgcg tcaatggggc ggagttgtta cgacattttg gaaagtcccg    14280
ttgattttgg tgccaaaaca aactcccatt gacgtcaatg gggtggagac ttggaaatcc    14340
ccgtgagtca aaccgctatc cacgcccatt gatgtactgc caaaaccgca tcaccatggt    14400
aatagcgatg actaatacgt agatgtactg ccaagtagga aagtcccata aggtcatgta    14460
ctgggcataa tgccaggcgg gccatttacc gtcattgacg tcaataggggg cgtacttgg    14520 catatgatac acttgatgta ctgccaagtg ggcagtttac cgtaaatagt ccacccattg    14580
acgtcaatgg aaagtcccta ttggcgttac tatgggaaca tacgtcatta ttgacgtcaa    14640
tgggcggggg tcgttgggcg gtcagccagg cgggccattt accgtaagtt atgtaacgcg    14700
gaactccata tatgggctat gaactaatga ccccgtaatt gattactatt aataactagt    14760
caataatcaa tgtcaacgcg tatatctggc ccgtacatcg gtaactagtc ggaccgccgc    14820
ggactagtgc ccgggccacc ggtgctcgaa gcttggatcg atccagacat gataagatac    14880
attgatgagt ttggacaaac cacaactaga atgcagtgaa aaaaatgctt tatttgtgaa    14940
atttgtgatg ctattgcttt atttgtaacc attataagct gcaataaaca agttaacaac    15000
aacaattgca ttcattttat gtttcaggtt caggggagg tgtgggaggt tttttaaagc     15060
aagtaaaacc tctacaaatg tggtatggct gattatgatc tctagtcaag              15110
```